(12) United States Patent
Brown et al.

(10) Patent No.: US 11,319,312 B2
(45) Date of Patent: *May 3, 2022

(54) PHARMACEUTICAL COMPOUNDS

(71) Applicant: Heptares Therapeutics Limited, Cambridge (GB)

(72) Inventors: Giles Albert Brown, Cambridge (GB); Barry John Teobald, Cambridge (GB); Benjamin Gerald Tehan, Cambridge (GB)

(73) Assignee: Heptares Therapeutics Limited

( * ) Notice: Subject to any disclaimer, the term of this patent is extended or adjusted under 35 U.S.C. 154(b) by 0 days.

This patent is subject to a terminal disclaimer.

(21) Appl. No.: 17/069,070

(22) Filed: Oct. 13, 2020

(65) Prior Publication Data

US 2021/0101893 A1    Apr. 8, 2021

Related U.S. Application Data

(63) Continuation of application No. 16/450,279, filed on Jun. 24, 2019, now Pat. No. 10,858,352.

(30) Foreign Application Priority Data

Jun. 22, 2018    (GB) ..................................... 1810245

(51) Int. Cl.

| | | |
|---|---|---|
| *C07D 487/10* | (2006.01) | |
| *C07D 498/08* | (2006.01) | |
| *C07D 498/10* | (2006.01) | |
| *C07D 451/02* | (2006.01) | |
| *C07D 451/14* | (2006.01) | |
| *C07D 453/06* | (2006.01) | |
| *C07D 471/10* | (2006.01) | |
| *C07D 413/14* | (2006.01) | |
| *C07D 491/08* | (2006.01) | |

(52) U.S. Cl.
CPC ......... *C07D 413/14* (2013.01); *C07D 451/02* (2013.01); *C07D 451/14* (2013.01); *C07D 453/06* (2013.01); *C07D 471/10* (2013.01); *C07D 487/10* (2013.01); *C07D 491/08* (2013.01); *C07D 498/08* (2013.01); *C07D 498/10* (2013.01); *C07B 2200/07* (2013.01); *C07B 2200/09* (2013.01)

(58) Field of Classification Search
CPC .. C07D 487/10; C07D 498/08; C07D 498/10; C07D 451/02; C07D 451/14; C07D 453/06; C07D 471/10; C07D 413/14

See application file for complete search history.

(56) References Cited

U.S. PATENT DOCUMENTS

| | | |
|---|---|---|
| 10,858,352 B2 | 12/2020 | Brown et al. |
| 2007/0043023 A1 | 2/2007 | Makings et al. |

FOREIGN PATENT DOCUMENTS

| | | |
|---|---|---|
| WO | 1999/32486 A1 | 7/1999 |
| WO | 2007/076070 A2 | 7/2007 |
| WO | 2007/100670 A1 | 9/2007 |
| WO | 2008/021375 A2 | 2/2008 |
| WO | 2012/037393 A1 | 3/2012 |
| WO | 2014/045031 A1 | 3/2014 |
| WO | 2014/122474 A1 | 8/2014 |
| WO | 2015/118342 A1 | 8/2015 |
| WO | 2015/140559 A1 | 9/2015 |
| WO | 2017/021729 A1 | 2/2017 |
| WO | 2017/021730 A1 | 2/2017 |
| WO | 2018/069732 A1 | 4/2018 |

OTHER PUBLICATIONS

International Search Report and Written Opinion for Application No. PCT/GB2019/051778, dated Aug. 20, 2019, 17 pages.

*Primary Examiner* — Laura L Stockton
(74) *Attorney, Agent, or Firm* — Fish & Richardson P.C.

(57) ABSTRACT

This invention relates to compounds that are agonists of the muscarinic $M_1$ and/or $M_4$ receptor and which are useful in the treatment of diseases mediated by the muscarinic $M_1$ and $M_4$ receptors. Also provided are pharmaceutical compositions containing the compounds and the therapeutic uses of the compounds. Compounds provided are of formula where $X^1$; $X^2$; $X^3$; $X^4$; $R^1$ $R^2$ and $R^4$ are as defined herein.

20 Claims, No Drawings

PHARMACEUTICAL COMPOUNDS

RELATED APPLICATION INFORMATION

This application is a continuation of U.S. patent application Ser. No. 16/450,279, filed Jun. 24, 2019, which claims priority to GB Application Serial No. 1810245.9, filed Jun. 22, 2018. These applications are herein incorporated by reference.

This invention relates to a class of novel heterocyclic compounds, their salts, pharmaceutical compositions containing them and their use in therapy of the human body. In particular, the invention is directed to a class of compounds, which are agonists of the muscarinic $M_1$ receptor and/or $M_4$ receptor, and hence are useful in the treatment of Alzheimer's Disease, schizoprenia, cognitive disorders and other diseases mediated by the muscarinic $M_1/M_4$ receptors, as well as the treatment or alleviation of pain.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 *Science*). In schizophrenia, which is also characterised by cognitive impairments, mAChR density is reduced in the pre-frontal cortex, hippocampus and caudate putamen of schizophrenic subjects (Dean et al., 2002 *Mol Psychiatry*). Furthermore, in animal models, blockade or lesion of central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting side effects resulting from stimulation of peripheral $M_2$ and $M_3$ mAChRs including disturbed gastrointestinal motility, bradycardia, nausea and vomiting (www.drugs.com/pro/donepezil.html; www.drugs.com/pro/rivastigmine.html).

Further discovery efforts have targeted the identification of direct $M_1$ mAChR agonists to target increases in cognitive function. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain sequelae: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, non-amyloidgenic and amyloidgenic. Cleavage of APP by γ-secretase is common to both pathways, but in the former APP is cleaved by an α-secretase to yield soluble APPα. The cleavage site is within the Aβ sequence, thereby precluding its formation. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 *Neuron*). Finally, the mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Furthermore, preclinical studies have suggested that mAChR agonists display an atypical antipsychotic-like profile in a range of pre-clinical paradigms. The mAChR agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*). Muscarinic receptors have also been implicated in the neurobiology of addicition. The reinforcing effects of cocaine and other addictive substances are mediated by the mesolimbic dopamine system where behavioral and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al Psychopharmacology (2011) August; 216(3):367-78). Furthermore xanomeline has been dmoenstrated to block the effects of cocaine in these models.

Muscarinic receptors are also involved in the control of movement and potentially represent novel treatments for movement disorders such as Parkinson's disease, ADHD, Huntingdon's disease, tourette's syndrome and other syndromes associated with dopaminergic dysfunction as an underlying pathogenetic factor driving disease.

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 *Arch Neurol*). This compound was also assessed in a small Phase II study of schizophrenics and gave a significant reduction in positive and negative symptoms when compared to placebo control (Shekhar et al., 2008 *Am J Psych*). However, in all clinical studies xanomeline and other related mAChR agonists have displayed an unacceptable safety margin with respect to cholinergic side effects, including nausea, gastrointestinal pain, diarrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 *Bioorg Med Chem Lett*; Johnson et al., 2010 *Bioorg Med Chem Lett*; Budzik et al., 2010 *ACS Med Chem Lett*). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

The Invention

The present invention provides compounds having activity as muscarinic $M_1$ and/or $M_4$ receptor agonists. More particularly, the invention provides compounds that exhibit selectivity for the $M_1$ and/or $M_4$ receptor relative to the $M_2$ and $M_3$ receptor subtypes.

Accordingly, in a first embodiment (Embodiment 1.1), the invention provides a compound of the formula (1):

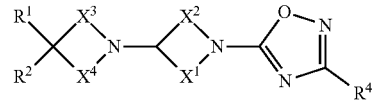
(1)

or a salt thereof, wherein:

$X^1$ and $X^2$ are saturated hydrocarbon groups which together contain a total of five to nine carbon atoms and zero or one oxygen atoms and which link together such that the moiety:

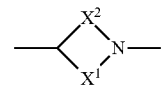

forms a monocyclic or bicyclic ring system;

$X^3$ and $X^4$ are saturated hydrocarbon groups which together contain a total of three to six carbon atoms and which link together such that the moiety:

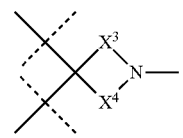

forms a monocyclic or bicyclic ring system;

$R^1$ is selected from $NR^5R^6$; $CONR^5R^6$; $COOR^7$; an optionally substituted 5- or 6-membered ring containing 0, 1, 2 or 3 heteroatoms selected from O, N and S and oxidized forms thereof; or $R^1$ is linked to $R^2$ to form an optionally substituted monocyclic or bicyclic ring containing 0, 1, 2 or 3 heteroatoms selected from O, N and S and oxidized forms thereof;

$R^2$ is selected from hydrogen; fluorine; cyano; hydroxy; amino; and a $C_{1-3}$ hydrocarbon group which is optionally substituted with one to six fluorine atoms and wherein one of the carbon atoms of the hydrocarbon group may optionally be replaced by a heteroatom selected from O, N and S and oxidized forms thereof, or $R^2$ is linked to $R^1$ to form an optionally substituted monocyclic or bicyclic ring containing 0, 1, 2 or 3 heteroatoms selected from O, N and S and oxidized forms thereof;

$R^4$ is H, halo, OH, CN, a $C_{1-6}$ alkyl group or a $C_{3-6}$ cycloalkyl group, wherein the alkyl and cycloalkyl groups are optionally substituted with one or more fluorine atoms, and wherein any one atom of the alkyl or cycloalkyl group may be optionally replaced by an O heteroatom;

$R^5$ is selected from hydrogen, $COCH_3$, a non-aromatic $C_{1-10}$ hydrocarbon group optionally substituted with one or more fluorine atoms wherein any one atom of the $C_{1-10}$ hydrocarbon group may be optionally replaced by a heteroatom selected from O, N and S, a group —$(CH_2)_n$-aryl, wherein n is 0-3, or $R^5$ can be joined together with $R^6$ to form an optionally substituted monocyclic or bicyclic ring containing 0, 1, 2 or 3 heteroatoms selected from O, N and S and oxidized forms thereof;

$R^6$ is selected from hydrogen, a non-aromatic $C_{1-10}$ hydrocarbon group optionally substituted with one or more fluorine atoms wherein any one atom of the $C_{1-10}$ hydrocarbon group may be optionally replaced by a heteroatom selected from O, N and S, a group —$(CH_2)_n$-aryl, wherein n is 0-3, or R⁶ can be joined together with R⁵ to form an optionally substituted monocyclic or bicyclic ring containing 0, 1, 2 or 3 heteroatoms selected from O, N and S and oxidized forms thereof; and R⁷ is a non-aromatic C₁₋₆ hydrocarbon group optionally substituted with one or more fluorine atoms.

In a further embodiment (Embodiment 1.2), the invention provides a compound of the formula (1a)

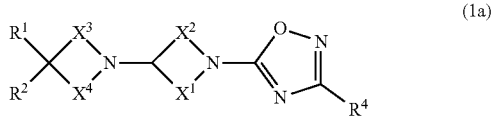
(1a)

or a salt thereof, wherein:

X¹ and X² are saturated hydrocarbon groups which together contain a total of five to nine carbon atoms and zero or one oxygen atoms and which link together such that the moiety:

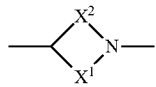

forms a monocyclic or bicyclic ring system;

X³ and X⁴ are saturated hydrocarbon groups which together contain a total of three to five carbon atoms and which link together such that the moiety:

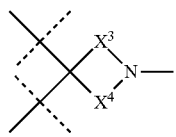

forms a monocyclic or bicyclic ring system;

R¹ is selected from NR⁵R⁶; CONR⁵R⁶; COOR⁷; an optionally substituted 5- or 6-membered ring containing 0, 1, 2 or 3 heteroatoms selected from O, N and S and oxidized forms thereof; or R¹ is linked to R² to form an optionally substituted monocyclic or bicyclic ring containing 0, 1, 2 or 3 heteroatoms selected from O, N and S and oxidized forms thereof;

R² is selected from hydrogen; fluorine; cyano; hydroxy; amino; and a C₁₋₃ hydrocarbon group which is optionally substituted with one to six fluorine atoms and wherein one of the carbon atoms of the hydrocarbon group may optionally be replaced by a heteroatom selected from O, N and S and oxidized forms thereof, or R² is linked to R¹ to form an optionally substituted monocyclic or bicyclic ring containing 0, 1, 2 or 3 heteroatoms selected from O, N and S and oxidized forms thereof;

R⁴ is H or a C₁₋₃ alkyl group;

R⁵ is selected from hydrogen, COCH₃, a non-aromatic C₁₋₆ hydrocarbon group optionally substituted with one or more fluorine atoms, or R⁵ can be joined together with R⁶ to form an optionally substituted monocyclic or bicyclic ring containing 0, 1, 2 or 3 heteroatoms selected from O, N and S and oxidized forms thereof;

R⁶ is selected from hydrogen, a non-aromatic C₁₋₆ hydrocarbon group optionally substituted with one or more fluorine atoms, or R⁶ can be joined together with R⁵ to form an optionally substituted monocyclic or bicyclic ring containing 0, 1, 2 or 3 heteroatoms selected from O, N and S and oxidized forms thereof; and R⁷ is a non-aromatic C₁₋₆ hydrocarbon group optionally substituted with one or more fluorine atoms.

Particular and preferred compounds of the formula (1) are as defined in the following Embodiments 1.3 to 1.42:

1.3 A compound according to Embodiment 1.1 or 1.2 wherein R¹ is an optionally substituted 5- or 6-membered ring containing 0, 1, 2 or 3 heteroatoms selected from O, N and S and oxidized forms thereof.

1.4 A compound according to Embodiment 1.3 wherein the optionally substituted ring is phenyl, pyrazolyl, pyrrolidinyl or pyrrolidinonyl.

1.5 A compound according to any of Embodiments 1.3 or 1.4 wherein the optional substituent of the 5- or 6-membered ring is selected from C₁-C₃ alkyl, C₁-C₃ alkoxy, CONR⁵R⁶, halogen, cyano, oxo, hydroxyl, amino or an optionally substituted heterocyclic ring containing 1 or 2 heteroatoms selected from O or N.

1.6 A compound according to any of Embodiments 1.3 or 1.4 wherein the optional substituent of the 5- or 6-membered ring is an optionally substituted pyrazole ring.

1.7 A compound according to Embodiment 1.6 wherein the optional substituent of the pyrazole ring is C₁-C₃ alkyl.

1.8 A compound according to Embodiment 1.1 or 1.2 wherein R¹ is selected from NR⁵R⁶; CONR⁵R⁶; COOR⁷.

1.9 A compound according to Embodiment 1.1 or 1.2 wherein R¹ is selected from:

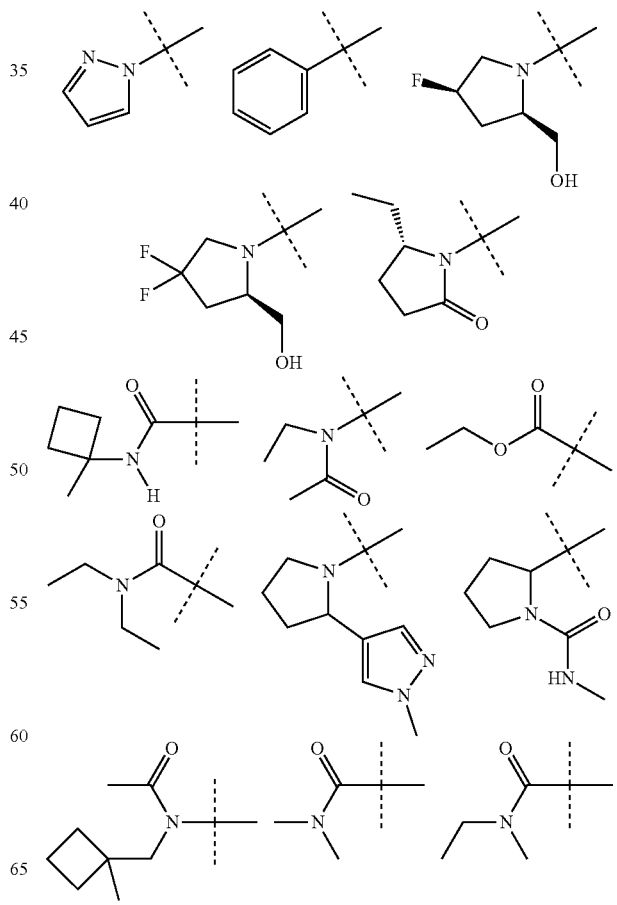

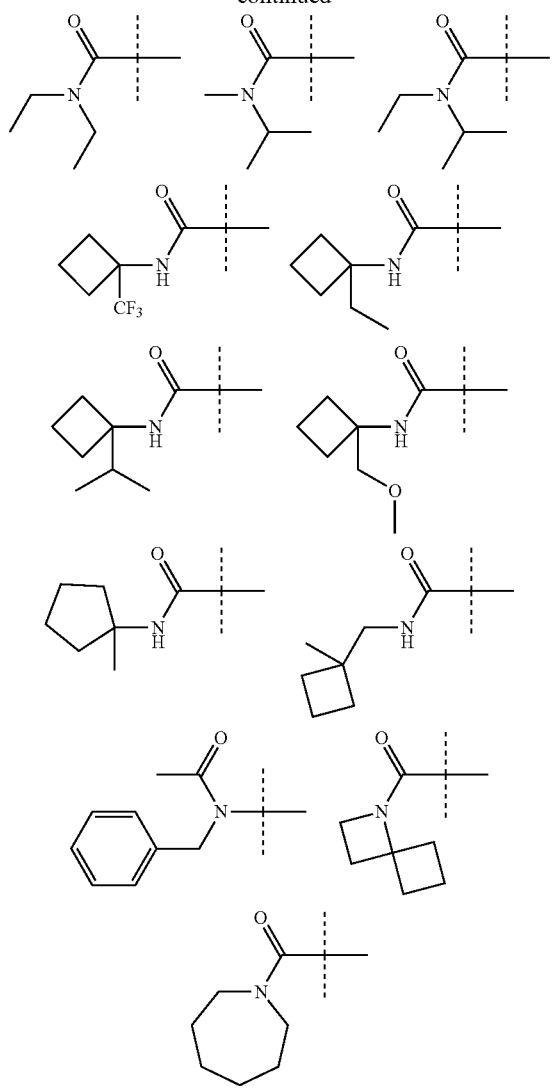

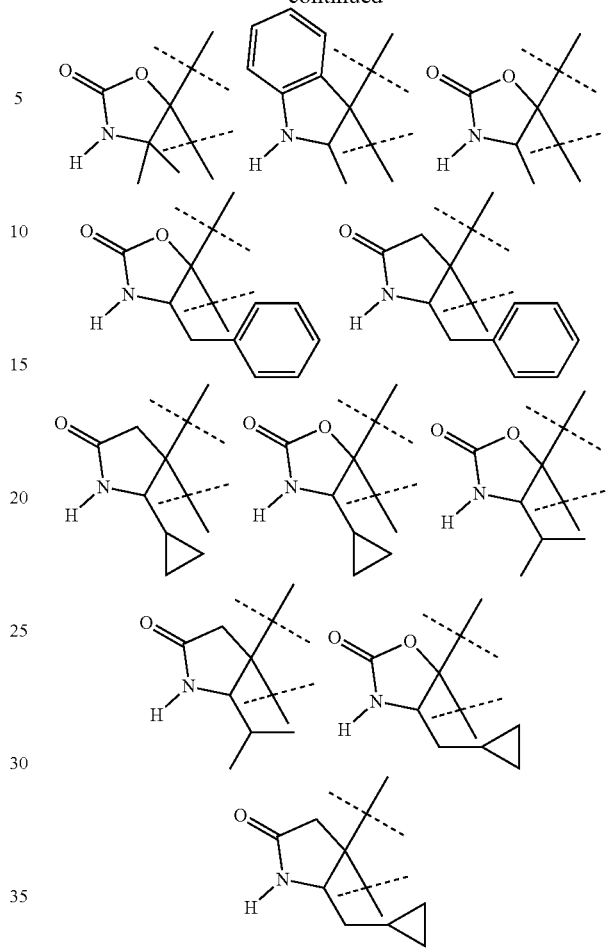

1.10 A compound according to Embodiment 1.1 or 1.2 wherein R¹ is linked to R² to form an optionally substituted monocyclic or bicyclic ring containing 0, 1, 2 or 3 heteroatoms selected from O, N and S and oxidized forms thereof.

1.11 A compound according to Embodiment 1.10 wherein R¹ and R² are linked to form an optionally substituted monocyclic ring selected from pyrrolidinonyl and oxazolidinonyl.

1.12 A compound according to Embodiment 1.10 wherein R¹ and R² are linked to form an optionally substituted indolinonyl ring.

1.13 A compound according to Embodiment 1.10 wherein the monocyclic or bicyclic ring is selected from:

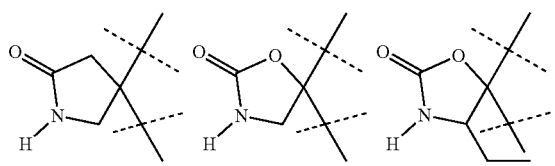

1.14 A compound according to any of Embodiments 1.10 to 1.13 wherein the optional substituents of the monocyclic or bicyclic ring are selected from $C_1$-$C_6$ alkyl, $C_1$-$C_3$ alkoxy, halogen, cyano, oxo, hydroxyl, amino or a group —$(CH_2)_n$-aryl wherein n is 0-3.

1.15 A compound according to any of Embodiments 1.10 to 1.14 wherein the optional substituents of the monocyclic or bicyclic ring are methyl or ethyl.

1.16 A compound according to any of Embodiments 1.5 or 1.8 wherein R⁵ is selected from hydrogen, $COCH_3$, a non-aromatic $C_{1-10}$ hydrocarbon group optionally substituted with one or more fluorine atoms, wherein any one atom of the $C_{1-10}$ hydrocarbon group may be optionally replaced by a heteroatom selected from O, N and S, a group —$(CH_2)_n$-aryl, wherein n is 0-3, or R⁵ can be joined together with R⁶ to form an optionally substituted monocyclic or bicyclic ring containing 0, 1, 2 or 3 heteroatoms selected from O, N and S and oxidized forms thereof, wherein the optional substituents are selected from $C_1$-$C_3$ alkyl, $C_1$-$C_3$ alkoxy, halogen, cyano, oxo, hydroxyl or amino, wherein the $C_1$-$C_3$ alkyl or $C_1$-$C_3$ alkoxy groups can have an optional substituent selected from halogen, cyano, oxo, hydroxyl or amino.

1.17 A compound according to any of Embodiments 1.5 or 1.8 wherein R⁶ is selected from hydrogen, a non-aromatic $C_{1-10}$ hydrocarbon group optionally substituted with one or more fluorine atoms, wherein any one atom of the $C_{1-10}$ hydrocarbon group may be optionally replaced by a heteroatom selected from O, N and S, a group —$(CH_2)_n$-aryl, wherein n is 0-3, or R⁶ can be joined together with R⁵ to form an optionally substituted monocyclic or bicyclic ring containing 0, 1, 2 or 3 heteroatoms selected from O, N and S and oxidized forms thereof, wherein the optional substituents are selected from $C_1$-$C_3$ alkyl, $C_1$-$C_3$ alkoxy, halogen, cyano, oxo, hydroxyl or amino, wherein the $C_1$-$C_3$ alkyl or $C_1$-$C_3$ alkoxy groups can have an optional substituent selected from halogen, cyano, oxo, hydroxyl or amino.

1.18 A compound according to any of Embodiments 1.1 to 1.17 wherein R⁵ and R⁶ are independently selected from hydrogen, $COCH_3$ and $C_{1-6}$ alkyl.

1.19 A compound according to Embodiment 1.18 wherein R⁵ and R⁶ are independently selected from methyl, ethyl or methylcyclobutyl.

1.20 A compound according to any of Embodiments 1.1 to 1.17 wherein R⁵ is $COCH_3$.

1.21 A compound according to Embodiment 1.1 wherein R⁷ is $C_1$-$C_3$ alkyl.

1.22 A compound according to Embodiment 1.1 wherein R⁷ is ethyl.

1.23 A compound according to any of Embodiments 1.1 to 1.22 wherein R² is selected from hydrogen; fluorine; cyano; hydroxy; amino; and a $C_{1-3}$ hydrocarbon group which is optionally substituted with one to six fluorine atoms and wherein one of the carbon atoms of the hydrocarbon group may optionally be replaced by a heteroatom selected from O, N and S and oxidized forms thereof, or R² is linked to R¹ to form an optionally substituted monocyclic or bicyclic ring containing 0, 1, 2 or 3 heteroatoms selected from O, N and S and oxidized forms thereof.

1.24 A compound according to any of Embodiments 1.1 to 1.23 wherein R² is hydrogen or cyano.

1.25 A compound according to any of Embodiments 1.1 to 1.24 wherein R² is hydrogen.

1.26 A compound according to any of Embodiments 1.1 to 1.24 wherein R² is cyano.

1.27 A compound according to any of Embodiments 1.1 to 1.23 wherein R² is linked to R¹ to form an optionally substituted spirocyclic group.

1.28 A compound according to Embodiment 1.1 wherein R⁴ is hydrogen or a $C_{1-6}$ alkyl group or a $C_{3-6}$ cycloalkyl group, wherein the alkyl and cycloalkyl groups are optionally substituted with one or more fluorine atoms, and wherein any one atom of the alkyl or cycloalkyl group may be optionally replaced by an O heteroatom.

1.29 A compound according to Embodiment 1.1 wherein R⁴ is hydrogen.

1.30 A compound according to Embodiment 1.1 wherein R⁴ is methyl.

1.31 A compound according to Embodiment 1.1 wherein R⁴ is ethyl.

1.32 A compound according to Embodiment 1.1 wherein R⁴ is halo, OH or CN.

1.33 A compound according to Embodiment 1.1 wherein R⁴ is methyl, trifluoromethyl, ethyl, isopropyl or cyclopropyl.

1.34 A compound according to any one of Embodiments 1.1 to 1.33 wherein the ring system formed by X¹ and X² is selected from 8-azabicyclo[3.2.1]octane, 9-azabicyclo[3.3.1]nonane, 6-azabicyclo[3.2.1]octane, 7-azaspiro[3.4]octane, 2-azaspiro[3.4]octane, 6-azaspiro[3.3]heptane, 3-azabicyclo[3.1.1]heptane, 3-oxa-9-azabicyclo[3.3.1]nonane, 2-azabicyclo[2.2.2]octane, piperidine and azepane.

1.35 A compound according to any one of Embodiments 1.1 to 1.33 wherein the ring system formed by X¹ and X² is selected from:

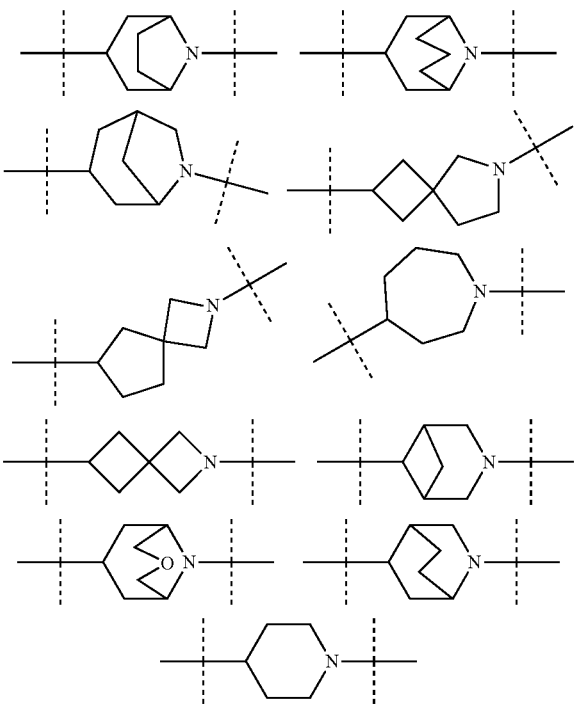

1.36 A compound according to Embodiment 1.1 wherein the ring system formed by X³ and X⁴ is selected from piperidine, azepane and 3-azabicyclo[3.1.0]hexane.

1.37 A compound according to Embodiment 1.1 wherein the ring system formed by X³ and X⁴ is selected from:

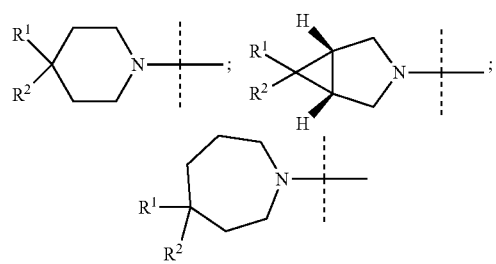

1.38 A compound according to Embodiment 1.36 wherein the ring system formed by X³ and X⁴ is piperidine.

1.39 A compound according to any of Embodiments 1.1 to 1.38 of the formula (2):

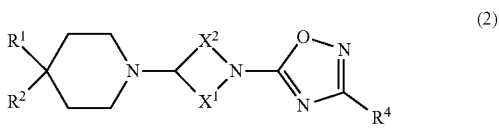

or a salt thereof wherein:

X¹, X², R¹ R² and R⁴ are as defined in any one of Embodiments 1.1 to 1.38.

1.40 A compound according to any of Embodiments 1.1 to 1.38 of the formula (3):

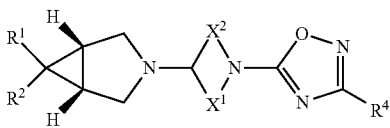

(3)

or a salt thereof wherein:

$X^1$, $X^2$, $R^1$ $R^2$ and $R^4$ are as defined in any one of Embodiments 1.1 to 1.38.

1.41 A compound according to any of Embodiments 1.1 to 1.38 of the formula (4):

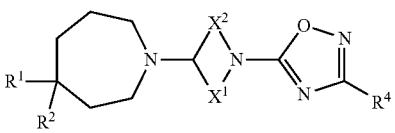

(4)

or a salt thereof wherein:

$X^1$, $X^2$, $R^1$ $R^2$ and $R^4$ are as defined in any one of Embodiments 1.1 to 1.38.

1.42 A compound according to any of Embodiments 1.1 to 1.41 selected from;

2-(3-Methyl-1,2,4-oxadiazol-5-yl)-6-[4-(1H-pyrazol-1-yl)piperidin-1-yl]-2-azaspiro[3.3]heptane;

6-(3-Methyl-1,2,4-oxadiazol-5-yl)-2-[4-(1H-pyrazol-1-yl)piperidin-1-yl]-6-azaspiro[3.4]octane;

1-[6-(3-Methyl-1,2,4-oxadiazol-5-yl)-6-azaspiro[3.4]oct-2-yl]-4-phenylpiperidine-4-carbonitrile;

Ethyl(1R,5S,6r)-3-[6-(3-methyl-1,2,4-oxadiazol-5-yl)-6-azaspiro[3.4]oct-2-yl]-3-azabicyclo[3.1.0]hexane-6-carboxylate;

2-(3-Methyl-1,2,4-oxadiazol-5-yl)-6-[4-(1H-pyrazol-1-yl)piperidin-1-yl]-2-azaspiro[3.4]octane;

1'-(3-Methyl-1,2,4-oxadiazol-5-yl)-4-(1H-pyrazol-1-yl)-1,4'-bipiperidine;

3-(3-Methyl-1,2,4-oxadiazol-5-yl)-6-[4-(1H-pyrazol-1-yl)piperidin-1-yl]-3-azabicyclo[3.1.1]heptane;

8-(3-Methyl-1,2,4-oxadiazol-5-yl)-3-[4-(1H-pyrazol-1-yl)piperidin-1-yl]-8-azabicyclo[3.2.1]octane;

8-[8-(3-Methyl-1,2,4-oxadiazol-5-yl)-8-azabicyclo[3.2.1]oct-3-yl]-2,8-diazaspiro[4.5]decan-3-one;

8-[8-(3-Ethyl-1,2,4-oxadiazol-5-yl)-8-azabicyclo[3.2.1]oct-3-yl]-2,8-diazaspiro[4.5]decan-3-one;

8-[8-(3-Methyl-1,2,4-oxadiazol-5-yl)-8-azabicyclo[3.2.1]octan-3-yl]-1-oxa-3,8-diazaspiro[4.5]decan-2-one;

N-(1-Methylcyclobutyl)-1-[8-(3-methyl-1,2,4-oxadiazol-5-yl)-8-azabicyclo[3.2.1]oct-3-yl]piperidine-4-carboxamide;

2-(3-Methyl-1,2,4-oxadiazol-5-yl)-5-[4-(1H-pyrazol-1-yl)piperidin-1-yl]-2-azabicyclo[2.2.2]octane;

9-(3-Methyl-1,2,4-oxadiazol-5-yl)-3-[4-(1H-pyrazol-1-yl)piperidin-1-yl]-9-azabicyclo[3.3.1]nonane;

8-[9-(3-Methyl-1,2,4-oxadiazol-5-yl)-9-azabicyclo[3.3.1]non-3-yl]-2,8-diazaspiro[4.5]decan-3-one;

8-[9-(3-Methyl-1,2,4-oxadiazol-5-yl)-9-azabicyclo[3.3.1]non-3-yl]-1-oxa-3,8-diazaspiro[4.5]decan-2-one;

N-(1-Methylcyclobutyl)-1-[9-(3-methyl-1,2,4-oxadiazol-5-yl)-9-azabicyclo[3.3.1]non-3-yl]piperidine-4-carboxamide;

9-(3-Methyl-1,2,4-oxadiazol-5-yl)-7-[4-(1H-pyrazol-1-yl)piperidin-1-yl]-3-oxa-9-azabicyclo[3.3.1]nonane;

(1R,5S,6r)-N,N-Diethyl-3-[9-(3-methyl-1,2,4-oxadiazol-5-yl)-3-oxa-9-azabicyclo[3.3.1]non-7-yl]-3-azabicyclo[3.1.0]hexane-6-carboxamide;

1-(3-Methyl-1,2,4-oxadiazol-5-yl)-4-[4-(1H-pyrazol-1-yl)piperidin-1-yl]azepane;

8-[1-(3-Methyl-1,2,4-oxadiazol-5-yl)azepan-4-yl]-2,8-diazaspiro[4.5]decan-3-one;

8-[1-(3-Methyl-1,2,4-oxadiazol-5-yl)azepan-4-yl]-1-oxa-3,8-diazaspiro[4.5]decan-2-one;

4-Ethyl-8-[1-(3-methyl-1,2,4-oxadiazol-5-yl)azepan-4-yl]-1-oxa-3,8-diazaspiro[4.5]decan-2-one;

4,4-Dimethyl-8-[1-(3-methyl-1,2,4-oxadiazol-5-yl)azepan-4-yl]-1-oxa-3,8-diazaspiro[4.5]decan-2-one;

1'-[1-(3-Methyl-1,2,4-oxadiazol-5-yl)azepan-4-yl]spiro[indole-3,4'-piperidin]-2(1H)-one;

[(2R,4R)-4-Fluoro-1-{1-[1-(3-methyl-1,2,4-oxadiazol-5-yl)azepan-4-yl]piperidin-4-yl}pyrrolidin-2-yl]methanol;

[(2R)-4,4-Difluoro-1-{1-[1-(3-methyl-1,2,4-oxadiazol-5-yl)azepan-4-yl]piperidin-4-yl}pyrrolidin-2-yl]methanol;

(5S)-5-Ethyl-1-{1-[1-(3-methyl-1,2,4-oxadiazol-5-yl)azepan-4-yl]piperidin-4-yl}pyrrolidin-2-one;

1-(3-Methyl-1,2,4-oxadiazol-5-yl)-4-{4-[2-(1-methyl-1H-pyrazol-4-yl)pyrrolidin-1-yl]piperidin-1-yl}azepane;

N-Ethyl-N-{1-[1-(3-methyl-1,2,4-oxadiazol-5-yl)azepan-4-yl]piperidin-4-yl}acetamide;

(2S)-N-Methyl-2-{1-[1-(3-methyl-1,2,4-oxadiazol-5-yl)azepan-4-yl]piperidin-4-yl}pyrrolidine-1-carboxamide;

6-(3-Methyl-1,2,4-oxadiazol-5-yl)-3-[4-(1H-pyrazol-1-yl)piperidin-1-yl]-6-azabicyclo[3.2.1]octane;

8-[6-(3-Methyl-1,2,4-oxadiazol-5-yl)-6-azabicyclo[3.2.1]oct-3-yl]-2,8-diazaspiro[4.5]decan-3-one;

8-[6-(3-Methyl-1,2,4-oxadiazol-5-yl)-6-azabicyclo[3.2.1]oct-3-yl]-1-oxa-3,8-diazaspiro[4.5]decan-2-one;

8-(2-(3-methyl-1,2,4-oxadiazol-5-yl)-2-azabicyclo[2.2.2]octan-5-yl)-2,8-diazaspiro[4.5]decan-3-one;

8-(2-(3-methyl-1,2,4-oxadiazol-5-yl)-2-azabicyclo[2.2.2]octan-5-yl)-1-oxa-3,8-diazaspiro[4.5]decan-2-one;

8-(8-(3-(trifluoromethyl)-1,2,4-oxadiazol-5-yl)-8-azabicyclo[3.2.1]octan-3-yl)-2,8-diazaspiro[4.5]decan-3-one;

8-(8-(3-(trifluoromethyl)-1,2,4-oxadiazol-5-yl)-8-azabicyclo[3.2.1]octan-3-yl)-1-oxa-3,8-diazaspiro[4.5]decan-2-one;

(1R,5S,6r)-3-(2-(3-methyl-1,2,4-oxadiazol-5-yl)-2-azaspiro[3.4]octan-6-yl)-N-(1-methylcyclobutyl)-3-azabicyclo[3.1.0]hexane-6-carboxamide;

1-(8-(3-methyl-1,2,4-oxadiazol-5-yl)-8-azabicyclo[3.2.1]octan-3-yl)-N-(1-(trifluoromethyl)cyclobutyl)piperidine-4-carboxamide;

N-(1-ethylcyclobutyl)-1-(8-(3-methyl-1,2,4-oxadiazol-5-yl)-8-azabicyclo[3.2.1]octan-3-yl)piperidine-4-carboxamide;

N-(1-isopropylcyclobutyl)-1-(8-(3-methyl-1,2,4-oxadiazol-5-yl)-8-azabicyclo[3.2.1]octan-3-yl)piperidine-4-carboxamide;

1-(8-(3-methyl-1,2,4-oxadiazol-5-yl)-8-azabicyclo[3.2.1]octan-3-yl)-N-(1-methylcyclopentyl)piperidine-4-carboxamide;

1-(8-(3-methyl-1,2,4-oxadiazol-5-yl)-8-azabicyclo[3.2.1]octan-3-yl)-N-((1-methylcyclobutyl)methyl)piperidine-4-carboxamide;

(1R,5S,6r)-3-(8-(3-methyl-1,2,4-oxadiazol-5-yl)-8-azabicyclo[3.2.1]octan-3-yl)-N-(1-methylcyclobutyl)-3-azabicyclo[3.1.0]hexane-6-carboxamide;

N-(1-methylcyclobutyl)-1-(8-(3-(trifluoromethyl)-1,2,4-oxadiazol-5-yl)-8-azabicyclo[3.2.1]octan-3-yl)piperidine-4-carboxamide;

1-(2-(3-methyl-1,2,4-oxadiazol-5-yl)-2-azabicyclo[2.2.2]octan-5-yl)-N-(1-methylcyclobutyl)piperidine-4-carboxamide;

1-(2-(3-methyl-1,2,4-oxadiazol-5-yl)-2-azabicyclo[2.2.2]octan-5-yl)-N-((1-methylcyclobutyl)methyl)piperidine-4-carboxamide;

N-(1-(9-(3-methyl-1,2,4-oxadiazol-5-yl)-3-oxa-9-azabicyclo[3.3.1]nonan-7-yl)piperidin-4-yl)-N-((1-methylcyclobutyl)methyl)acetamide;

N-(1-(8-(3-methyl-1,2,4-oxadiazol-5-yl)-8-azabicyclo[3.2.1]octan-3-yl)piperidin-4-yl)-N-((1-methylcyclobutyl)methyl)acetamide;

N-(1-(2-(3-methyl-1,2,4-oxadiazol-5-yl)-2-azabicyclo[2.2.2]octan-5-yl)piperidin-4-yl)-N-((1-methylcyclobutyl)methyl)acetamide;

N-benzyl-N-(1-(9-(3-methyl-1,2,4-oxadiazol-5-yl)-3-oxa-9-azabicyclo[3.3.1]nonan-7-yl)piperidin-4-yl)acetamide;

((1R,5S,6r)-3-(9-(3-methyl-1,2,4-oxadiazol-5-yl)-3-oxa-9-azabicyclo[3.3.1]nonan-7-yl)-3-azabicyclo[3.1.0]hexan-6-yl)(1-azaspiro[3.3]heptan-1-yl)methanone;

(1R,5S,6r)-N-isopropyl-N-methyl-3-(9-(3-methyl-1,2,4-oxadiazol-5-yl)-3-oxa-9-azabicyclo[3.3.1]nonan-7-yl)-3-azabicyclo[3.1.0]hexane-6-carboxamide;

(1R,5S,6r)-N,N-diethyl-3-(9-(3-(trifluoromethyl)-1,2,4-oxadiazol-5-yl)-3-oxa-9-azabicyclo[3.3.1]nonan-7-yl)-3-azabicyclo[3.1.0]hexane-6-carboxamide;

(1R,5S,6r)-N-ethyl-N-methyl-3-(8-(3-methyl-1,2,4-oxadiazol-5-yl)-8-azabicyclo[3.2.1]octan-3-yl)-3-azabicyclo[3.1.0]hexane-6-carboxamide;

(1R,5S,6r)-N,N-diethyl-3-(8-(3-methyl-1,2,4-oxadiazol-5-yl)-8-azabicyclo[3.2.1]octan-3-yl)-3-azabicyclo[3.1.0]hexane-6-carboxamide;

(1R,5S,6r)-N,N-diethyl-3-(2-(3-methyl-1,2,4-oxadiazol-5-yl)-2-azaspiro[3.4]octan-6-yl)-3-azabicyclo[3.1.0]hexane-6-carboxamide;

(1R,5S,6r)-N-ethyl-N-methyl-3-(2-(3-methyl-1,2,4-oxadiazol-5-yl)-2-azaspiro[3.4]octan-6-yl)-3-azabicyclo[3.1.0]hexane-6-carboxamide;

N,N-diethyl-1-(2-(3-methyl-1,2,4-oxadiazol-5-yl)-2-azaspiro[3.4]octan-6-yl)piperidine-4-carboxamide;

8-(8-(3-methyl-1,2,4-oxadiazol-5-yl)-8-azabicyclo[3.2.1]octan-3-yl)-2,8-diazaspiro[4.6]undecan-3-one;

8-(8-(3-methyl-1,2,4-oxadiazol-5-yl)-8-azabicyclo[3.2.1]octan-3-yl)-1-oxa-3,8-diazaspiro[4.6]undecan-2-one;

8-(2-(3-methyl-1,2,4-oxadiazol-5-yl)-2-azabicyclo[2.2.2]octan-5-yl)-2,8-diazaspiro[4.6]undecan-3-one;

8-(2-(3-methyl-1,2,4-oxadiazol-5-yl)-2-azabicyclo[2.2.2]octan-5-yl)-1-oxa-3,8-diazaspiro[4.6]undecan-2-one;

8-(6-(3-methyl-1,2,4-oxadiazol-5-yl)-6-azabicyclo[3.2.1]octan-3-yl)-2,8-diazaspiro[4.6]undecan-3-one;

8-(6-(3-methyl-1,2,4-oxadiazol-5-yl)-6-azabicyclo[3.2.1]octan-3-yl)-1-oxa-3,8-diazaspiro[4.6]undecan-2-one;

((1R,5S,6r)-3-(6-(3-methyl-1,2,4-oxadiazol-5-yl)-6-azabicyclo[3.2.1]octan-3-yl)-3-azabicyclo[3.1.0]hexan-6-yl)(1-azaspiro[3.3]heptan-1-yl)methanone;

(1R,5S,6r)-N,N-diethyl-3-(6-(3-methyl-1,2,4-oxadiazol-5-yl)-6-azabicyclo[3.2.1]octan-3-yl)-3-azabicyclo[3.1.0]hexane-6-carboxamide;

(1R,5S,6r)-N-ethyl-N-isopropyl-3-(6-(3-methyl-1,2,4-oxadiazol-5-yl)-6-azabicyclo[3.2.1]octan-3-yl)-3-azabicyclo[3.1.0]hexane-6-carboxamide;

(1R,5S,6r)-N-isopropyl-N-methyl-3-(6-(3-methyl-1,2,4-oxadiazol-5-yl)-6-azabicyclo[3.2.1]octan-3-yl)-3-azabicyclo[3.1.0]hexane-6-carboxamide;

(1R,5S,6r)-N-ethyl-N-methyl-3-(9-(3-methyl-1,2,4-oxadiazol-5-yl)-9-azabicyclo[3.3.1]nonan-3-yl)-3-azabicyclo[3.1.0]hexane-6-carboxamide;

(1R,5S,6r)-N,N-diethyl-3-(9-(3-methyl-1,2,4-oxadiazol-5-yl)-9-azabicyclo[3.3.1]nonan-3-yl)-3-azabicyclo[3.1.0]hexane-6-carboxamide;

8-(1-(3-(trifluoromethyl)-1,2,4-oxadiazol-5-yl)azepan-4-yl)-2,8-diazaspiro[4.5]decan-3-one;

8-(1-(3-(trifluoromethyl)-1,2,4-oxadiazol-5-yl)azepan-4-yl)-2,8-diazaspiro[4.6]undecan-3-one;

8-(1-(3-methyl-1,2,4-oxadiazol-5-yl)azepan-4-yl)-2,8-diazaspiro[4.6]undecan-3-one;

8-(1-(3-(trifluoromethyl)-1,2,4-oxadiazol-5-yl)azepan-4-yl)-1-oxa-3,8-diazaspiro[4.5]decan-2-one;

8-(1-(3-(trifluoromethyl)-1,2,4-oxadiazol-5-yl)azepan-4-yl)-1-oxa-3,8-diazaspiro[4.6]undecan-2-one;

8-(1-(3-methyl-1,2,4-oxadiazol-5-yl)azepan-4-yl)-1-oxa-3,8-diazaspiro[4.6]undecan-2-one;

8-(8-(3-ethyl-1,2,4-oxadiazol-5-yl)-8-azabicyclo[3.2.1]octan-3-yl)-1-oxa-3,8-diazaspiro[4.5]decan-2-one;

8-(6-(3-(trifluoromethyl)-1,2,4-oxadiazol-5-yl)-6-azabicyclo[3.2.1]octan-3-yl)-1-oxa-3,8-diazaspiro[4.5]decan-2-one;

4-methyl-8-(8-(3-methyl-1,2,4-oxadiazol-5-yl)-8-azabicyclo[3.2.1]octan-3-yl)-1-oxa-3,8-diazaspiro[4.5]decan-2-one;

(1R,5S,6r)-3-(6-(3-methyl-1,2,4-oxadiazol-5-yl)-6-azaspiro[3.4]octan-2-yl)-N-(1-methylcyclobutyl)-3-azabicyclo[3.1.0]hexane-6-carboxamide;

N-(1-(6-(3-methyl-1,2,4-oxadiazol-5-yl)-6-azaspiro[3.4]octan-2-yl)piperidin-4-yl)-N-((1-methylcyclobutyl)methyl)acetamide;

(1R,5S,6r)-N,N-dimethyl-3-(9-(3-(trifluoromethyl)-1,2,4-oxadiazol-5-yl)-3-oxa-9-azabicyclo[3.3.1]nonan-7-yl)-3-azabicyclo[3.1.0]hexane-6-carboxamide;

(1R,5S,6r)-N-ethyl-N-methyl-3-(6-(3-methyl-1,2,4-oxadiazol-5-yl)-6-azabicyclo[3.2.1]octan-3-yl)-3-azabicyclo[3.1.0]hexane-6-carboxamide;

(1R,5S,6r)-N-isopropyl-N-methyl-3-(8-(3-methyl-1,2,4-oxadiazol-5-yl)-8-azabicyclo[3.2.1]octan-3-yl)-3-azabicyclo[3.1.0]hexane-6-carboxamide;

(1R,5S,6r)-N-ethyl-N-methyl-3-(2-(3-methyl-1,2,4-oxadiazol-5-yl)-2-azabicyclo[2.2.2]octan-5-yl)-3-azabicyclo[3.1.0]hexane-6-carboxamide;

8-(1-(3-methyl-1,2,4-oxadiazol-5-yl)azepan-4-yl)-1-oxa-3,8-diazaspiro[4.5]decan-2-one;

8-(8-(3-cyclopropyl-1,2,4-oxadiazol-5-yl)-8-azabicyclo[3.2.1]octan-3-yl)-2,8-diazaspiro[4.5]decan-3-one;

8-(8-(3-isopropyl-1,2,4-oxadiazol-5-yl)-8-azabicyclo[3.2.1]octan-3-yl)-2,8-diazaspiro[4.5]decan-3-one;

4-benzyl-8-(8-(3-methyl-1,2,4-oxadiazol-5-yl)-8-azabicyclo[3.2.1]octan-3-yl)-1-oxa-3,8-diazaspiro[4.5]decan-2-one;

1-isopropyl-8-(8-(3-methyl-1,2,4-oxadiazol-5-yl)-8-azabicyclo[3.2.1]octan-3-yl)-2,8-diazaspiro[4.5]decan-3-one;

4-isopropyl-8-(8-(3-methyl-1,2,4-oxadiazol-5-yl)-8-azabicyclo[3.2.1]octan-3-yl)-1-oxa-3,8-diazaspiro[4.5]decan-2-one;

1-cyclopropyl-8-(8-(3-methyl-1,2,4-oxadiazol-5-yl)-8-azabicyclo[3.2.1]octan-3-yl)-2,8-diazaspiro[4.5]decan-3-one;

8-(8-(3-cyclopropyl-1,2,4-oxadiazol-5-yl)-8-azabicyclo[3.2.1]octan-3-yl)-1-oxa-3,8-diazaspiro[4.5]decan-2-one;

8-(8-(3-isopropyl-1,2,4-oxadiazol-5-yl)-8-azabicyclo[3.2.1]octan-3-yl)-1-oxa-3,8-diazaspiro[4.5]decan-2-one;

N-benzyl-N-(1-(8-(3-methyl-1,2,4-oxadiazol-5-yl)-8-azabicyclo[3.2.1]octan-3-yl)piperidin-4-yl)acetamide;

(1R,5S,6r)-N,N-diethyl-3-(2-(3-methyl-1,2,4-oxadiazol-5-yl)-2-azaspiro[3.3]heptan-6-yl)-3-azabicyclo[3.1.0]hexane-6-carboxamide;

((1R,5S,6r)-3-(6-(3-methyl-1,2,4-oxadiazol-5-yl)-6-azaspiro[3.4]octan-2-yl)-3-azabicyclo[3.1.0]hexan-6-yl)(1-azaspiro[3.3]heptan-1-yl)methanone;

azepan-1-yl(1-(8-(3-methyl-1,2,4-oxadiazol-5-yl)-8-azabicyclo[3.2.1]octan-3-yl)piperidin-4-yl)methanone;

1-(cyclopropylmethyl)-8-(8-(3-methyl-1,2,4-oxadiazol-5-yl)-8-azabicyclo[3.2.1]octan-3-yl)-2,8-diazaspiro[4.5]decan-3-one;

4-(cyclopropylmethyl)-8-(8-(3-methyl-1,2,4-oxadiazol-5-yl)-8-azabicyclo[3.2.1]octan-3-yl)-1-oxa-3,8-diazaspiro[4.5]decan-2-one;

4-cyclopropyl-8-(8-(3-methyl-1,2,4-oxadiazol-5-yl)-8-azabicyclo[3.2.1]octan-3-yl)-1-oxa-3,8-diazaspiro[4.5]decan-2-one;

1-benzyl-8-(6-(3-methyl-1,2,4-oxadiazol-5-yl)-6-azaspiro[3.4]octan-2-yl)-2,8-diazaspiro[4.5]decan-3-one;

4-benzyl-8-(2-(3-methyl-1,2,4-oxadiazol-5-yl)-2-azaspiro[3.3]heptan-6-yl)-1-oxa-3,8-diazaspiro[4.5]decan-2-one;

1-benzyl-8-(1-(3-methyl-1,2,4-oxadiazol-5-yl)azepan-4-yl)-2,8-diazaspiro[4.5]decan-3-one;

1-benzyl-8-(8-(3-methyl-1,2,4-oxadiazol-5-yl)-8-azabicyclo[3.2.1]octan-3-yl)-2,8-diazaspiro[4.5]decan-3-one;

(1R,5S,6r)-3-(8-(3-methyl-1,2,4-oxadiazol-5-yl)-8-azabicyclo[3.2.1]octan-3-yl)-N-(1-(trifluoromethyl)cyclobutyl)-3-azabicyclo[3.1.0]hexane-6-carboxamide;

(1R,5S,6r)-3-(2-(3-methyl-1,2,4-oxadiazol-5-yl)-2-azabicyclo[2.2.2]octan-5-yl)-N-(1-(trifluoromethyl)cyclobutyl)-3-azabicyclo[3.1.0]hexane-6-carboxamide;

or a salt thereof.

1.43 A compound according to Embodiment 1.1 which is as defined in any one of Examples 1-1 to 18-2.

1.44 A compound according to any one of Embodiments 1.1 to 1.43 having a molecular weight of less than 550, for example less than 500, or less than 450.

1.45 A compound according to any one of Embodiments 1.1 to 1.44 which is in the form of a salt.

1.46 A compound according to Embodiment 1.45 wherein the salt is an acid addition salt.

1.47 A compound according to Embodiment 1.45 or Embodiment 1.46 wherein the salt is a pharmaceutically acceptable salt.

Definitions

In this application, the following definitions apply, unless indicated otherwise.

The term "treatment", in relation to the uses of the compounds of the formula (1), formula (1a), formula (2), formula (3) or formula (4), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "alkyl", "heterocyclic" and "ether" are used in their conventional sense (e.g. as defined in the IUPAC Gold Book) unless indicated otherwise.

The term "monocyclic" as used herein refers to an arrangement of atoms arranged in such a way as to form a single ring structure. The term "bicyclic" as used herein refers to an arrangement of atoms arranged in such a way as to form two joined rings. A bicyclic compound can be carbocyclic, or heterocyclic. Moreover, the two rings can both be aliphatic, or can be aromatic, or a combination of aliphatic and aromatic.

In the definitions of $X^1$, $X^2$, $X^3$, $X^4$, $R^1$, $R^2$, $R^4$, $R^5$, $R^6$ or $R^7$ above, where stated, one or two but not all, carbon atoms of the non-aromatic hydrocarbon groups or alkyl or cycloalkyl groups may optionally be replaced by a heteroatom selected from O and N. Where the group is a single carbon ($C_1$) group, the carbon can not be replaced. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—$S(O)_2$—$CH_2$—, replacement of a carbon atom in a —$CH_2$—$CH_2$—$CH_2$— chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formula (1), formula (1a), formula (2), formula (3) or formula (4), can exist in the form of salts, for example acid addition salts or, in certain cases salts of organic and inorganic bases such as carboxylate, sulfonate and phosphate salts. All such salts are within the scope of this invention, and references to compounds of the formula (1), formula (1a), formula (2), formula (3) or formula (4), include the salt forms of the compounds as defined in Embodiments 1.40 to 1.47.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.46) may be formed with a wide variety of acids, both inorganic and organic. Examples of acid addition salts falling within Embodiment 1.46 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1), formula (1a), formula (2), formula (3) or formula (4), contain an amine function, these may form quaternary ammonium salts, for example by reaction with an alkylating agent according to methods well known to the skilled person. Such quaternary ammonium compounds are within the scope of formula (1), formula (1a), formula (2), formula (3) or formula (4).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.48), the invention provides a geometric isomer of a compound according to any one of Embodiments 1.1 to 1.47.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.49) the invention provides a compound according to any one of Embodiments 1.1 to 1.48 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphor-sulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.50), the invention provides compositions containing a compound according to Embodiment 1.49 having one or more chiral centres, wherein at least 55% (e.g. at least 60%, 65%, 70%, 75%, 80%, 85%, 90% or 95%) of the compound of Embodiment 1.44 is present as a single optical isomer (e.g. enantiomer or diastereoisomer).

In one general embodiment (Embodiment 1.51), 99% or more (e.g. substantially all) of the total amount of the compound (or compound for use) of Embodiment 1.49 is present as a single optical isomer.

For example, in one embodiment (Embodiment 1.52) the compound is present as a single enantiomer.

In another embodiment (Embodiment 1.53), the compound is present as a single diastereoisomer.

The invention also provides mixtures of optical isomers, which may be racemic or non-racemic. Thus, the invention provides:

1.54 A compound according to Embodiment 1.49 which is in the form of a racemic mixture of optical isomers.

1.55 A compound according to Embodiment 1.49 which is in the form of a non-racemic mixture of optical isomers.

Isotopes

The compounds of the invention as defined in any one of Embodiments 1.1 to 1.55 may contain one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.56), the compound of any one of Embodiments 1.1 to 1.53 contains no radioactive isotopes. Such compounds are preferred for therapeutic use. In another embodiment (Embodiment 1.57), however, the compound of any one of Embodiments 1.1 to 1.55 may contain one or more radioisotopes. Compounds containing such radioisotopes may be useful in a diagnostic context.

Solvates

Compounds of the formula (1), formula (1a), formula (2), formula (3) or formula (4), as defined in any one of Embodiments 1.1 to 1.57 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.58 and 1.59, the invention provides:

1.58 A compound according to any one of Embodiments 1.1 to 1.57 in the form of a solvate.

1.59 A compound according to Embodiment 1.58 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.60), the invention provides a compound as defined in any one of Embodiments 1.1 to 1.58 in an anhydrous form (e.g. anhydrous crystalline form).

Crystalline and Amorphous Forms

The compounds of any one of Embodiments 1.1 to 1.60 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.61 A compound according to any one of Embodiments 1.1 to 1.60 in a crystalline form.

1.62 A compound according to any one of Embodiments 1.1 to 1.61 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.63 A compound according to any one of Embodiments 1.1 to 1.62 which is in an amorphous form.

Prodrugs

The compounds of the formula (1), formula (1a), formula (2), formula (3) or formula (4), as defined in any one of Embodiments 1.1 to 1.60 may be presented in the form of a pro-drug. By "prodrugs" is meant for example any compound that is converted in vivo into a biologically active compound of the formula (1), formula (1a), formula (2), formula (3) or formula (4), as defined in any one of Embodiments 1.1 to 1.60.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.64), the invention provides a pro-drug of a compound as defined in any one of Embodiments 1.1 to 1.60 wherein the compound contains a functional group which is convertible under physiological conditions to form a hydroxyl group or amino group.

Complexes and Clathrates

Also encompassed by formula (1), formula (1a), formula (2), formula (3) or formula (4), in Embodiments 1.1 to 1.64 are complexes (e.g. inclusion complexes or clathrates with compounds such as cyclodextrins, or complexes with metals) of the compounds of Embodiments 1.1 to 1.64.

Accordingly, in another embodiment (Embodiment 1.65), the invention provides a compound according to any one of Embodiments 1.1 to 1.64 in the form of a complex or clathrate.

Biological Activity and Therapeutic Uses

The compounds of the present invention have activity as muscarinic $M_1$ and/or $M_4$ receptor agonists. The muscarinic activity of the compounds can be determined using the Phospho-ERK1/2 assay described in Example A below.

A significant advantage of compounds of the invention is that they are highly selective for the $M_1$ and/or $M_4$ receptor relative to the $M_2$ and $M_3$ receptor subtypes. Compounds of the invention are neither agonists nor antagonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 95) against the $M_1$ receptor in the functional assay described in Example A, they may have $pEC_{50}$ values of less than 5 and $E_{max}$ values of less than 20% when tested against the $M_2$ and $M_3$ subtypes in the functional assay of Example A.

Some compounds of the invention have activity at both the $M_1$ and $M_4$ receptors.

Accordingly, in Embodiments 2.1 to 2.17, the invention provides:

2.1 A compound according to any one of Embodiments 1.1 to 1.65 for use in medicine.

2.2 A compound according to any one of Embodiments 1.1 to 1.65 for use as a muscarinic $M_1$ and/or $M_4$ receptor agonist.

2.3 A compound according to any one of Embodiments 1.1 to 1.65 which is a muscarinic $M_1$ receptor agonist having a $pEC_{50}$ greater than 6.9 and an $E_{max}$ of at least 80 against the $M_1$ receptor in the assay of Example A herein or an assay substantially similar thereto.

2.4 A compound according to Embodiment 2.3 which is a muscarinic $M_1$ receptor agonist having a $pEC_{50}$ greater than 7.0.

2.5 A compound according to Embodiment 2.3 or Embodiment 2.4 having an $E_{max}$ of at least 90 against the $M_1$ receptor.

2.6 A compound according to any one of Embodiments 1.1 to 1.65 which is a muscarinic $M_1$ and/or $M_4$ receptor agonist having a $pEC_{50}$ in the range from 6.0 to 8.7 and an $E_{max}$ of at least 60 against the $M_4$ receptor in the assay of Example A herein or an assay substantially similar thereto.

2.7 A compound according to any one of Embodiments 1.1 to 1.65 which is a muscarinic $M_1$ and/or $M_4$ receptor agonist having a $pEC_{50}$ in the range from 6.0 to 8.1 and an $E_{max}$ of at least 90 against the $M_4$ receptor in the assay of Example A herein or an assay substantially similar thereto.

2.8 A compound according to Embodiment 2.6 which is a muscarinic $M_4$ receptor agonist having a $pEC_{50}$ in the range from 7.5 to 8.7.

2.9 A compound according to Embodiment 2.7 which is a muscarinic $M_4$ receptor agonist having a $pEC_{50}$ in the range from 6.5 to 7.5.

2.10 A compound according to Embodiment 2.6 or Embodiment 2.8 having an $E_{max}$ of at least 75 against the $M_4$ receptor.

2.11 A compound according to Embodiment 2.7 or Embodiment 2.9 having an $E_{max}$ of at least 95 against the $M_4$ receptor.

2.12 A compound according to any one of Embodiments 2.3 to 2.11 which is selective for the $M_1$ and $M_4$ receptor compared to the muscarinic $M_2$ and $M_3$ receptors.

2.13 A compound according to Embodiment 2.12 which is selective for the $M_1$ receptor compared to the muscarinic $M_2$ and $M_3$ receptors.

2.14 A compound according to any one of Embodiments 2.3 to 2.5 which is selective for the $M_1$ receptor compared to the muscarinic $M_2$, $M_3$ and $M_4$ receptors.

2.15 A compound according to any one of Embodiments 2.3 to 2.14 which has a $pEC_{50}$ of less than 5 and an $E_{max}$ of less than 50 against the muscarinic $M_2$ and $M_3$ receptor subtypes.

2.16 A compound according to Embodiment 2.15 which has a $pEC_{50}$ of less than 4.5 and/or an $E_{max}$ of less than 30 against the muscarinic $M_2$ and $M_3$ receptor subtypes.

2.17 A compound according to any one of Embodiments 1.1 to 1.65 and Embodiments 2.3 to 2.16 for use in the treatment of a disease or condition mediated by the muscarinic $M_1$ receptor.

By virtue of their muscarinic $M_1$ and/or $M_4$ receptor agonist activity, compounds of the invention can be used in the treatment of Alzheimer's disease, schizophrenia and other psychotic disorders, cognitive disorders and other diseases mediated by the muscarinic $M_1$ and/or $M_4$ receptor, and can also be used in the treatment of various types of pain.

Accordingly, in Embodiments 2.18 to 2.39, the invention provides:

2.18 A compound according to any one of Embodiments 1.1 to 1.65 for use in the treatment of a cognitive disorder or psychotic disorder.

2.19 A compound for use according to Embodiment 2.18 wherein the cognitive disorder or psychotic disorder comprises, arises from or is associated with a condition selected from cognitive impairment, Mild Cognitive Impairment (including mild cognitive impairment due to Alzheimer's disease and/or prodromal Alzheimer's disease), frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease (including prodromal Alzheimer's disease and stages 1, 2, and 3 early Alzheimer's disease as defined by the US Food and Drug Admistration's "Early Alzheimer's disease: Developing Drugs for Treatment" available at fda.gov/downloads/Drugs/GuidanceComplianceRegulatoryInformation/Guidances/UCM596728.pdf), progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, AIDS-related dementia or other dementia states such as multi-infarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders and and schizo-affective disorder.

2.20 A compound according to any one of Embodiments 1.1 to 1.65 for use in the treatment of Alzheimer's disease.

2.21 A compound according to any one of Embodiments 1.1 to 1.65 for use in the treatment of Schizophrenia.

2.22 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.65.

2.23 A method according to Embodiment 2.22 wherein the cognitive disorder comprises, arises from or is associated with a condition as defined in Embodiment 2.17.

2.24 A method according to Embodiment 2.23 wherein the cognitive disorder arises from or is associated with Alzheimer's disease.

2.25 A method according to Embodiment 2.23 wherein the cognitive disorder is Schizophrenia.

2.26 The use of a compound according to any one of Embodiments 1.1 to 1.65 for the manufacture of a medicament for the treatment of a cognitive disorder.

2.27 The use according to Embodiment 2.26 wherein the cognitive disorder comprises, arises from or is associated with a condition as defined in Embodiment 2.19.

2.28 The use according to Embodiment 2.27 wherein the cognitive disorder arises from or is associated with Alzheimer's disease.

2.29 The use according to Embodiment 2.28 wherein the cognitive disorder is Schizophrenia.

2.30 A compound according to any one of Embodiments 1.1 to 1.65 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.31 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.65.

2.32 A compound according to any one of Embodiments 1.1 to 1.65 for the treatment of peripheral disorders such as reduction of intra ocular pressure in Glaucoma and treatment of dry eyes and dry mouth including Sjogren's Syndrome.

2.33 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.65.

2.34 The use of a compound according to any one of Embodiments 1.1 to 1.65 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.35 The use of a compound according to any one of Embodiments 1.1 to 1.65 for the use in the treatment of skin lesions for example due to pemphigus vulgaris, dermatitis herpetiformis, pemphigoid and other blistering skin conditions.

2.36 The use of a compound according to any one of Embodiments 1.1 to 1.65 for the use in treating, preventing, ameliorating or reversing conditions associated with altered gastro-intestinal function and motility such as functional dyspepsia, irritable bowel syndrome, gastroesophageal acid reflux (GER) and esophageal dysmotility, symptoms of gastroparesis and chronic diarrhea.

2.37 The use of a compound according to any one of Embodiments 1.1 to 1.65 for the use in in the treatment of olfactory dysfunction such as Bosma-Henkin-Christiansen syndrome, chemical poisoning (e.g. selenium and silver), hypopituitarism, Kallmann Syndrome, skull fractures, tumour therapy and underactive thyroid gland.

2.38 The use of a compound according to any one of Embodiments 1.1 to 1.65 for the treatment of addiction.

2.39 The use of a compound according to any one of Embodiments 1.1 to 1.65 for the treatment of movement disorders such as Parkinson's disease, ADHD, Huntingdon's disease, tourette's syndrome and other syndromes associated with dopaminergic dysfunction as an underlying pathogenetic factor driving disease.

2.40 The use of a compound according to any one of Embodiments 1.1 to 1.65 for the treatment of behavioural and psychological symptoms of dementia (BPSD; including agitation, verbal aggressiveness, physical aggressiveness, depression, anxiety, abnormal motor behaviour, elated mood, irritablility, apathy, disinhibition, impulsivity, delusions, hallucinations, sleep changes, and apetite changes).

Methods for the Preparation of Compounds of the Formula (1) or Formula (2)

Compounds of the formula (1), formula (1a), formula (2), formula (3) or formula (4), can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.65, which process comprises:

(A) the reaction of a compound of the formula (10):

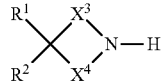
(10)

with a compound of the formula (11):

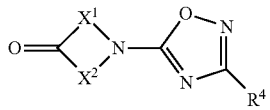
(11)

under reductive amination conditions; wherein $R^1$, $R^2$, $R^4$, $X^1$, $X^2$, $X^3$ and $X^4$ are as defined in any one of Embodiments 1.1 to 1.65; or (B) when it is required to prepare a compound of formula (1) wherein $R^1$ comprises $CONR^5R^6$:

the reaction of a compound of the formula (12):

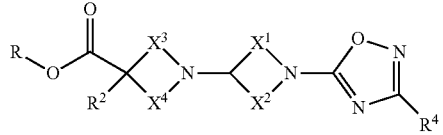
(12)

with an amine of the formula $R^5R^6NH$; wherein R represents a suitable group such as methyl- or ethyl- and $R^2$, $R^4$, $R^5$, $R^6$, $X^1$, $X^2$, $X^3$ and $X^4$ are as defined in any one of Embodiments 1.1 to 1.65; or (C) when it is required to prepare a compound of formula (1) wherein $R^1$ comprises $CONR^5R^6$:

the reaction of a compound of the formula (13):

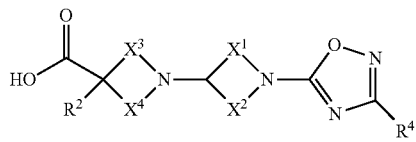
(13)

with an amine of the formula $R^5R^6NH$; wherein R represents a suitable group such as methyl- or ethyl- and $R^2$, $R^4$, $R^5$, $R^6$, $X^1$, $X^2$, $X^3$ and $X^4$ are as defined in any one of Embodiments 1.1 to 1.65; or (D) when it is required to prepare a compound of formula (1) wherein $R^1$ comprises a 5- or 6-membered ring containing a N(C=O)OR or N(C=O)$NR_2$ group:

the reaction of an amine of the formula (14):

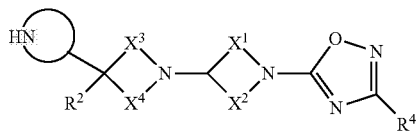
(14)

with a compound of the formula (15) or (16):

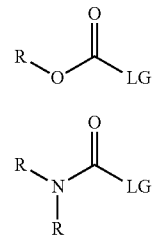
(15)

(16)

wherein $R^2$, $R^4$, $X^1$, $X^2$, $X^3$ and $X^4$ are as defined in any one of Embodiments 1.1 to 1.65 and LG represents a suitable leaving group such as Cl, 1-imidazole or 4-nitrophenol; or
and optionally:

(E) converting one compound of the formula (1) to another compound of the formula (1).

In process variant (A), the ketone (11) is reacted with the amine (10) under reductive amination conditions. The reductive amination reaction is typically carried out at ambient temperature to mild heating (e.g. at a temperature of about 20° C. to about 70° C.) using a borohydride reducing agent such as sodium triacetoxy-borohydride (STAB) in a solvent such as dichloromethane (DCM), dichloroethane (DCE), N,N-dimethylformamide (DMF) or methanol (MeOH) containing an acid such as acetic acid (AcOH) or trifluoroacetic acid (TFA), or sodium cyanoborohydride (NaCNBH$_3$) in combination with zinc chloride (ZnCl$_2$) in a solvent such as MeOH, or STAB in a solvent such as DCM or DCE containing an acid such as AcOH or TFA in combination with titanium tetraisopropoxide (Ti(O$^i$Pr)$_4$). Optionally, the amine (10) may be present in the reaction as an acid salt such as a hydrogen chloride (HCl), hydrogen bromide (HBr) or a TFA salt, optionally in the presence of a tertiary base such as triethylamine (TEA) or N,N-diisopropylamine (DIPEA).

Amines of the formula (10) may be sourced commercially or may be prepared by a variety of different methods that exist in the art and that are well known to the skilled person.

Ketones of the formula (11) can be prepared by the sequence of reactions shown in Scheme 1 below. Thus, an N-protected amino ketone (17), wherein the protecting group PG represents a suitable protecting group such as BOC or CBZ, can be reacted under reducing conditions suitable to effect formation of N-protected amino alcohol (18). Typically, such conditions might be reaction with a borohydride reducing agent such as sodium borohydride (NaBH$_4$) in a solvent such as MeOH, or lithium borohydide (LiBH$_4$) in a solvent such as Et$_2$O or THF, or an aluminium hydride reagent such as lithium aluminium hydride (LAH) in a solvent such as Et$_2$O or THF, at a temperature of about −20° C. to about 50° C. Once formed, N-protected amino alcohol (18) can be deprotected to give amino alcohol (19). For example, when the protecting group PG is BOC, then suitable conditions to effect its removal might be reaction with an acid such as HCl in a solvent such as 1,4-dioxane or Et$_2$O, or TFA in a solvent such as DCM. Alternatively, when the protecting group PG is CBZ then suitable conditions to effect its removal might be reaction with H$_2$ in the presence of a palladium on carbon (Pd/C) catalyst in a solvent such as EtOH at a temperature of about 20° C. to about 80° C. Once formed, amino alcohol (19) can be reacted with cyanogen bromide in a suitable solvent such as DCM, MeCN, Et$_2$O or EtOH in the presence of a suitable base such as Et$_3$N, NaHCO$_3$, Na$_2$CO$_3$, or K$_2$CO$_3$, optionally in the presence of water, at a temperature of about 0° C. to about 50° C., to form cyanamide (20). Once formed, cyanamide (20) can be reacted with a suitable N-hydroxy reagent such as N-hydroxyamide (22) or the corresponding N-hydroxyamidine (23), wherein R$^4$ is as defined in any one of Embodiments 1.1 to 1.65, in a suitable solvent such as EtOAc, Et$_2$O, THF, 1,4-dioxane or EtOH, or a mixture of the aforementioned solvents, in the presence of a lewis acid such as zinc chloride or zinc bromide, at a temperature of about 0° C. to about 25° C., and then later heated at a temperature of about 50° C. to about 100° C. in a suitable solvent such as EtOH in the presence aqueous acid e.g. aqueous HCl to form alcohol (21). Alternatively, amino alcohol (19) can be reacted directly with an oxadiazole (24), wherein R$^4$ is as defined in any one of Embodiments 1.1 to 1.65 and LG represents a suitable leaving group such as halogen (e.g. fluoride, chloride or bromide) or a sulphonic acid ester (e.g. a tosylate, mesylate or triflate), optionally in the presence of a suitable solvent such as THF, 1,4-dioxane, MeCN, EtOH, DMSO, DMF or NMP, optionally in the presence of a suitable base such as Et$_3$N, DIPEA, K$_2$CO$_3$ or DBU, at a temperature suitable to promote reaction, e.g. at a temperature of about 20° C. to about 200° C., optionally using a sealed vessel under a reaction pressure greater than atmospheric pressure, optionally using conventionally heating or microwave heating. Once formed, alcohol (21) can be oxidized to ketone (11) using a wide variety of reagents and conditions that exist in the art and that are well known to the skilled person, e.g. by using a chromium reagent such as pyridinium chlorochromate in a suitable solvent such a DCM at a temperature of about 0° C. to about 25° C.

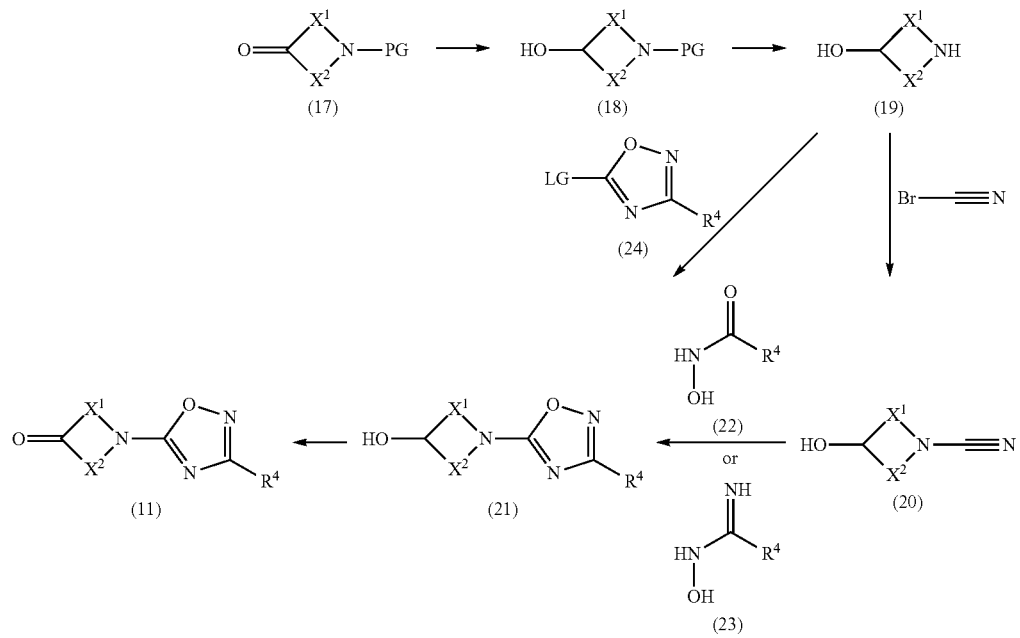

Scheme 1

In process variant (B), the ester (12) is reacted with the amine R$^5$R$^6$NH under conditions suitable to effect formation of an amide. Typically, such conditions are reaction at a temperature between about 0° C. to about 110° C. in a solvent such as toluene in combination with a reagent such as trimethylaluminium (Me$_3$Al), optionally in the presence of a tertiary base such as TEA or DIPEA. It will be well known to the skilled person that other suitable conditions exist to effect formation of an amide from ester (12) and amine R$^5$R$^6$NH, such as reaction in the presence of isopropylmagnesium chloride ($^i$PrMgCl) in a suitable solvent, or by direct heating of ester (12) and amine R$^5$R$^6$NH together, optionally in the presence of a suitable solvent, optionally in the presence of a suitable base such as TEA or DIPEA.

In process variant (C), the carboxylic acid (13) is reacted with the amine R$^5$R$^6$NH under conditions suitable to effect formation of an amide. It will be well known to the skilled person that many suitable conditions exist in the art to effect formation of an amide from carboxylic acid (13) and amine R$^5$R$^6$NH, for example reaction with an amide coupling reagent such as diisopropylcarbodiimide (DIC), ethyl-(N', N'-dimethylamino)propylcarbodiimide hydrochloride (EDC), (benzotriazol-1-yloxy)tripyrrolidinophosphonium hexafluorophosphate (PyBOP), O-(7-azabenzotriazol-1-yl)-N,N,N',N'-tetramethyluronium hexafluorophosphate (HATU), (1-cyano-2-ethoxy-2-oxoethylidenaminooxy)dimethylamino-morpholino-carbenium hexafluorophosphate (COMU) or 2,4,6-tripropyl-1,3,5,2,4,6-trioxatriphosphorinane-2,4,6-trioxide (T3P), optionally in the presence of a tertiary base such as TEA or DIPEA, optionally in the presence of 1-hydroxybenzotriazole (HOBt), in a solvent such as DCM, THF or DMF, at a temperature between about 0° C. to about 100° C.

Alternatively, a compound of formula (1) wherein $R^1$ comprises $CONR^5R^6$ can be prepared from carboxylic acid (13) and an amine $R^5R^6NH$ by the sequence of reactions shown in Scheme 2 below:

Scheme 2

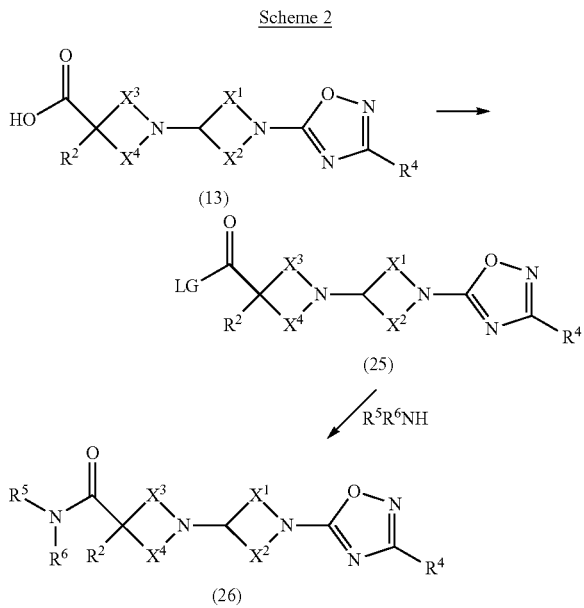

Thus carboxylic acid (13) can be reacted under conditions suitable to effect formation of intermediate (25), wherein $R^2$, $R^4$, $X^1$, $X^2$, $X^3$ and $X^4$ are as defined in any one of Embodiments 1.1 to 1.65 and LG represents a suitable leaving group such as chloride (Cl), 1-imidazole, or RO(C=O)O (wherein R represents a group such as ethyl- or isobutyl-). Typically, such conditions are reaction with a reagent such as oxalyl chloride or thionyl chloride (LG=Cl), 1,1'-carbonyldiimidazole (CDI) (LG=1-imidazole) or ethyl- or isobutyl-chloroformate (LG=RO(C=O)O), optionally in the presence of a tertiary base such as TEA or DIPEA, optionally in the presence of a catalyst such as DMF, in a suitable solvent such as DCM, THF or DMF. Once formed, intermediate (25) is reacted with an amine $R^5R^6NH$ under conditions suitable to effect formation of amide (26), wherein $R^2$, $R^4$, $R^5$, $R^6$, $X^1$, $X^2$, $X^3$ and $X^4$ are as defined in any one of Embodiments 1.1 to 1.65. Typically, such conditions are reaction at a temperature between about 0° C. to about 100° C. in a solvent such as DCM, THF or DMF, optionally in the presence of a tertiary base such as TEA or DIPEA.

In process variant (D), an amine of formula (14) is reacted with a compound of formula (15) or a compound of formula (16) under suitable conditions to form a compound of formula (1) wherein $R^1$ comprises a 5- or 6-membered ring containing a N(C=O)OR or N(C=O)$NR_2$ group. Typically, such conditions are reaction at a temperature between about 0° C. to about 100° C. in a solvent such as DCM, THF or DMF, optionally in the presence of a suitable base such as TEA, DIPEA or $K_2CO_3$.

In process variant (E), one compound of the formula (1) can be converted into another compound of the formula (1) by methods well known to the skilled person. Examples of synthetic procedures for converting one functional group into another functional group are set out in standard texts such as *March's Advanced Organic Chemistry: Reactions,* *Mechanisms, and Structure,* 7th Edition, Michael B. Smith, John Wiley, 2013, (ISBN: 978-0-470-46259-1), *Organic Syntheses,* Online Edition, www.orgsyn.org, (ISSN 2333-3553) and *Fiesers' Reagents for Organic Synthesis,* Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Greene's Protective Groups in Organic Synthesis,* Fifth Edition, Editor: Peter G. M. Wuts, John Wiley, 2014, (ISBN: 9781118057483).

Compounds made by the foregoing methods may be isolated and purified by any of a variety of methods well known to those skilled in the art and examples of such methods include recrystallisation and chromatographic techniques such as column chromatography (e.g. flash chromatography), HPLC and SFC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1), formula (1a), formula (2), formula (3) or formula (4), as defined in any one of Embodiments 1.1 to 1.65 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1), formula (1a), formula (2), formula (3) or formula (4) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragees, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1), formula (1a), formula (2), formula (3) or formula (4) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 18-2

The compounds of Examples 1-1 to 18-2 shown in Table 1 below have been prepared. Some of their NMR and LCMS properties and the methods used to prepare them are set out in Table 3. The starting materials and intermediates for some of the Examples are listed in Table 2.

TABLE 1

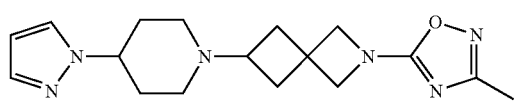 [SMILES: Cc1noc(N2CC3(CC(N4CCC(n5cccn5)CC4)C3)C2)n1]

Example 1-1

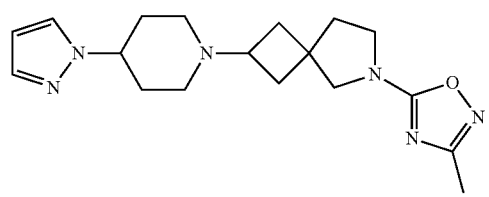 [SMILES: Cc1noc(N2CCC3(CC(N4CCC(n5cccn5)CC4)C3)C2)n1]

Example 2-1

TABLE 1-continued
| | |
|---|---|
| 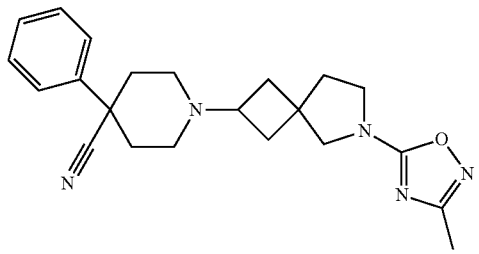 [SMILES: Cc1noc(N2CCC3(CC(N4CCC(C#N)(c5ccccc5)CC4)C3)C2)n1] | Example 2-2 |
| 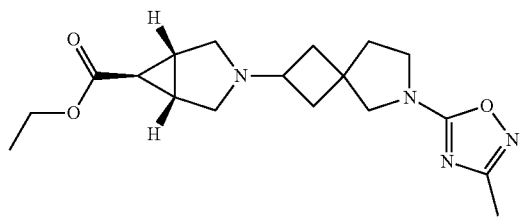 [SMILES: CCOC(=O)[C@H]1[C@@H]2CN(C3CC4(CCN(c5nc(C)no5)C4)C3)C[C@@H]21] | Example 2-3 |
| 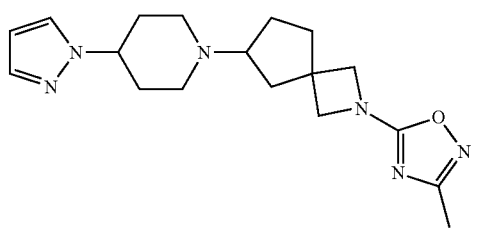 [SMILES: Cc1noc(N2CC3(CCC(N4CCC(n5cccn5)CC4)C3)C2)n1] | Example 3-1 |
| 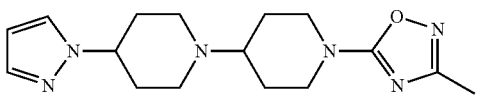 [SMILES: Cc1noc(N2CCC(N3CCC(n4cccn4)CC3)CC2)n1] | Example 4-1 |
| 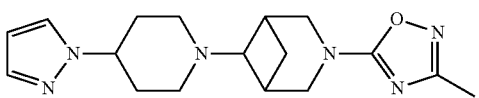 | Example 5-1 |
| 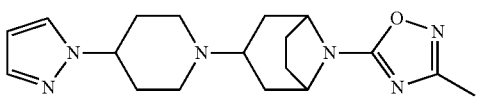 [SMILES: Cc1noc(N2C3CCC2CC(N2CCC(n4cccn4)CC2)C3)n1] | Example 6-1 |
| 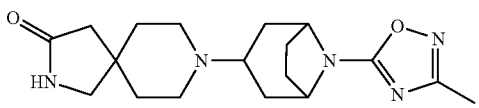 | Example 6-2 |
| 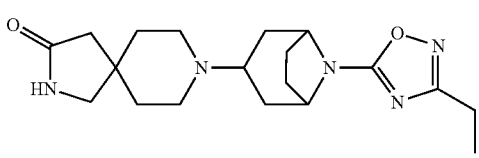 | Example 6-3 |
| 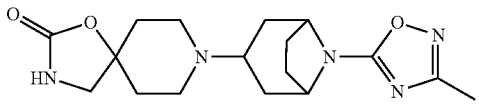 [SMILES: Cc1noc(N2C3CCC2CC(N2CCC4(CC2)CNC(=O)O4)C3)n1] | Example 6-4 |
| 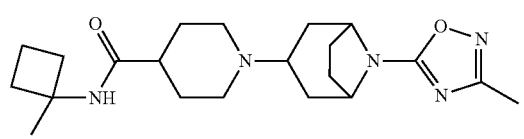 | Example 6-5 |

TABLE 1-continued
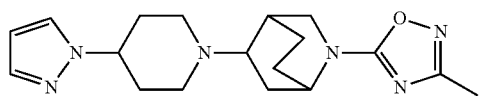 Example 7-1
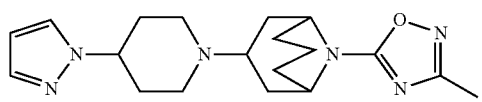 Example 8-1
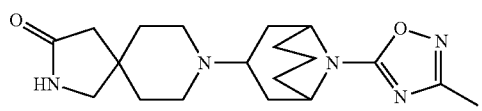 [SMILES: Cc1noc(N2C3CCCC2CC(N2CCC4(CC2)CNC(=O)C4)C3)n1] Example 8-2
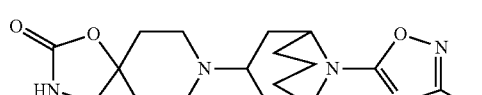 Example 8-3
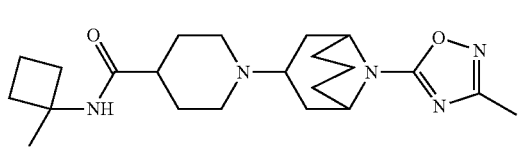 [SMILES: Cc1noc(N2C3CCCC2CC(N2CCC(C(=O)NC4(C)CCC4)CC2)C3)n1] Example 8-4
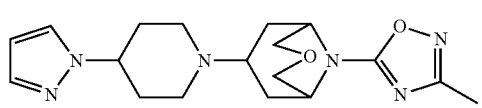 Example 9-1
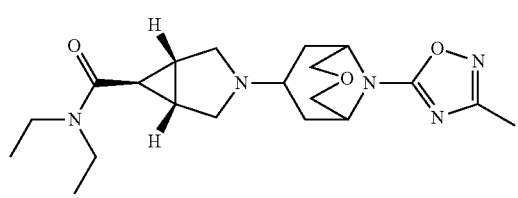 [SMILES: CCN(CC)C(=O)[C@H]1[C@@H]2CN(C3CC4COCC(C3)N4c3nc(C)no3)C[C@@H]21] Example 9-2
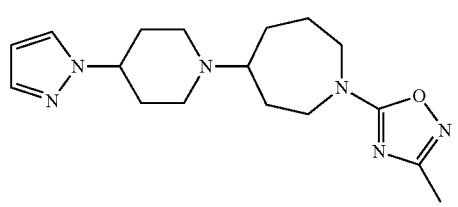 [SMILES: Cc1noc(N2CCCC(N3CCC(n4cccn4)CC3)CC2)n1] Example 10-1
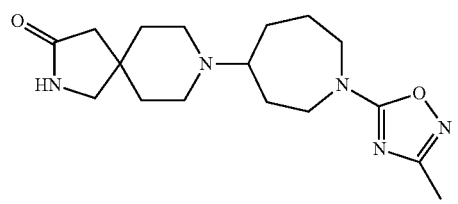 [SMILES: Cc1noc(N2CCCC(N3CCC4(CC3)CNC(=O)C4)CC2)n1] Example 10-2
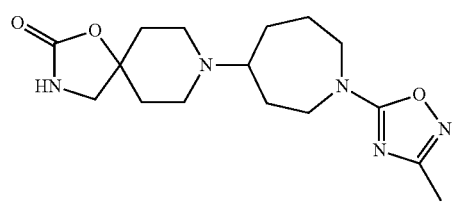 [SMILES: Cc1noc(N2CCCC(N3CCC4(CC3)CNC(=O)O4)CC2)n1] Example 10-3

TABLE 1-continued
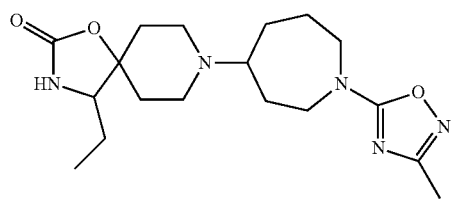 [SMILES: CCC1NC(=O)OC12CCN(C1CCCN(c3nc(C)no3)CC1)CC2]
Example 10-4
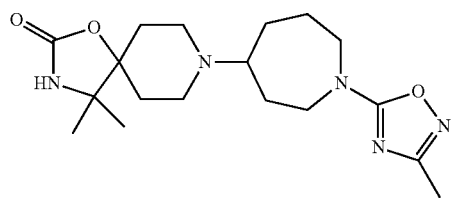 [SMILES: Cc1noc(N2CCCC(N3CCC4(CC3)OC(=O)NC4(C)C)CC2)n1]
Example 10-5
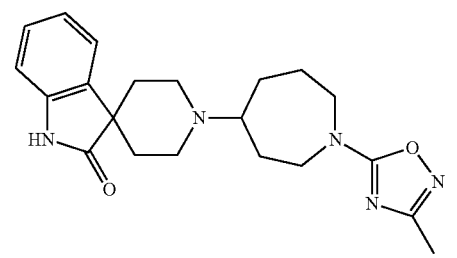 [SMILES: Cc1noc(N2CCCC(N3CCC4(CC3)C(=O)Nc3ccccc34)CC2)n1]
Example 10-6
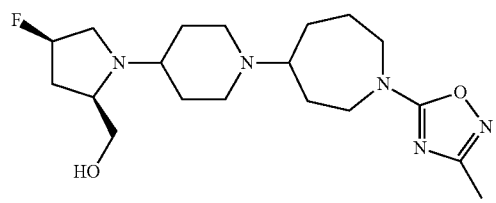 [SMILES: Cc1noc(N2CCCC(N3CCC(N4C[C@H](F)C[C@@H]4CO)CC3)CC2)n1]
Example 10-7
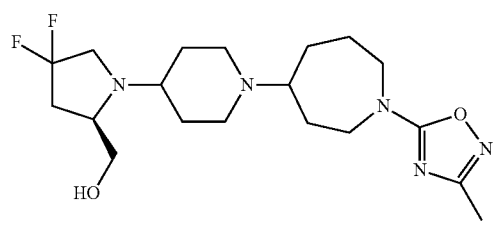 [SMILES: Cc1noc(N2CCCC(N3CCC(N4CC(F)(F)C[C@@H]4CO)CC3)CC2)n1]
Example 10-8
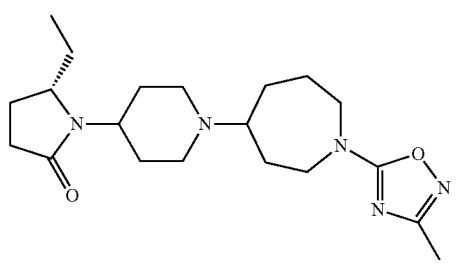 [SMILES: CC[C@H]1CCC(=O)N1C1CCN(C2CCCN(c3nc(C)no3)CC2)CC1]
Example 10-9
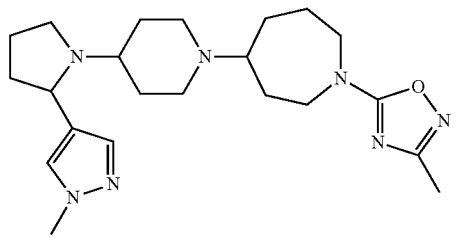 [SMILES: Cc1noc(N2CCCC(N3CCC(N4CCCC4c4cnn(C)c4)CC3)CC2)n1]
Example 10-10

TABLE 1-continued
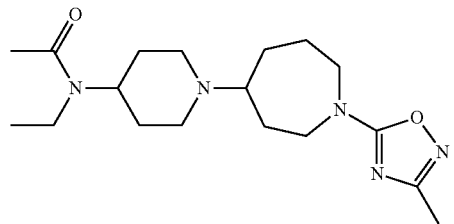 [SMILES: CCN(C(C)=O)C1CCN(C2CCCN(c3nc(C)no3)CC2)CC1]
Example 10-11
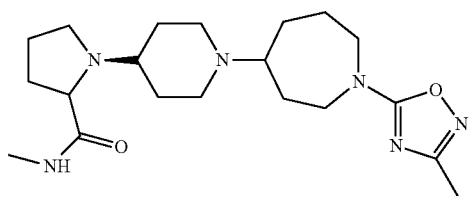
Example 10-12
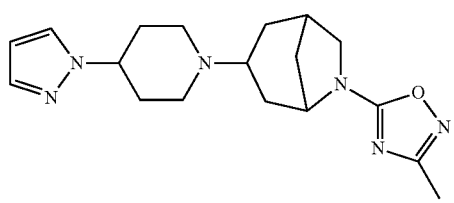 [SMILES: Cc1noc(N2CC3CC(N4CCC(n5cccn5)CC4)CC2C3)n1]
Example 11-1
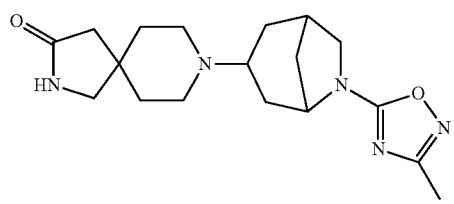 [SMILES: Cc1noc(N2CC3CC(N4CCC5(CC4)CNC(=O)C5)CC2C3)n1]
Example 11-2
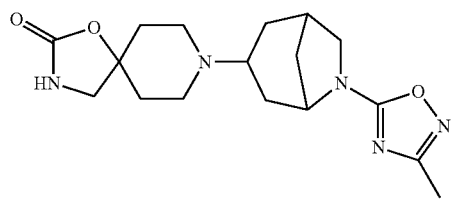 [SMILES: Cc1noc(N2CC3CC(N4CCC5(CC4)CNC(=O)O5)CC2C3)n1]
Example 11-3
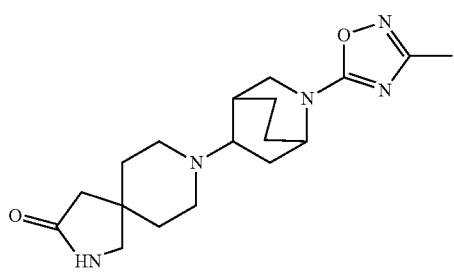 [SMILES: Cc1noc(N2CC3CCC2CC3N2CCC3(CC2)CNC(=O)C3)n1]
Example 12-1
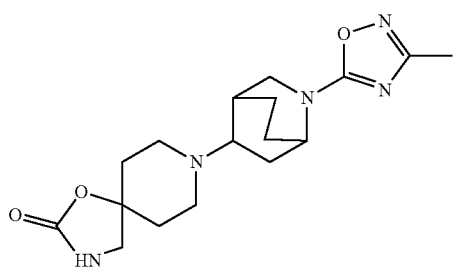 [SMILES: Cc1noc(N2CC3CCC2CC3N2CCC3(CC2)CNC(=O)O3)n1]
Example 12-2

TABLE 1-continued
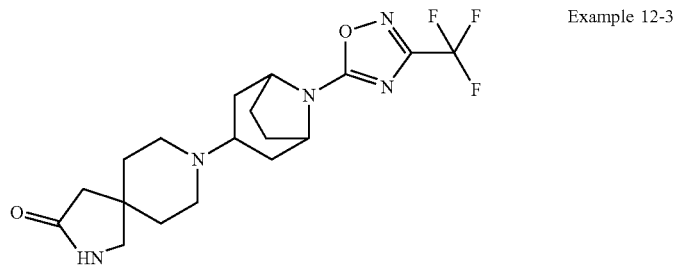
Example 12-3
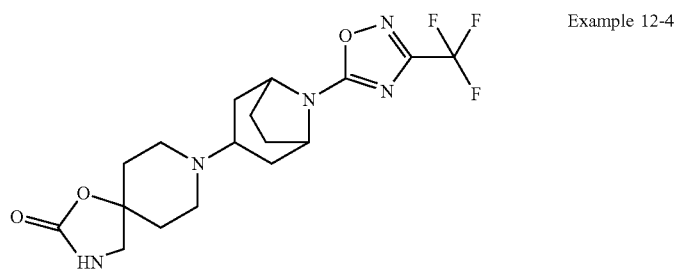
Example 12-4
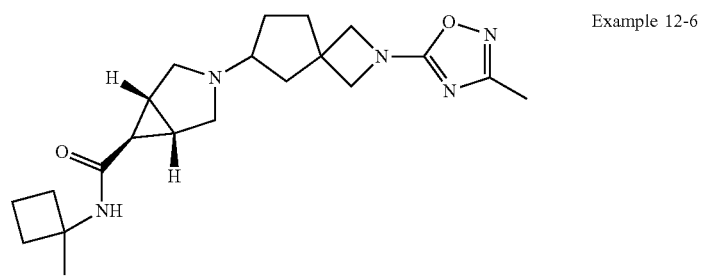
Example 12-6
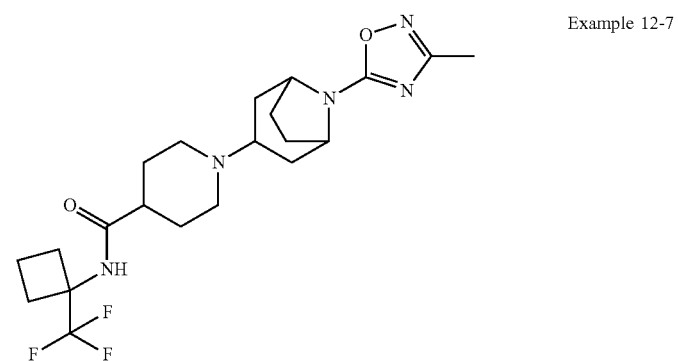
Example 12-7
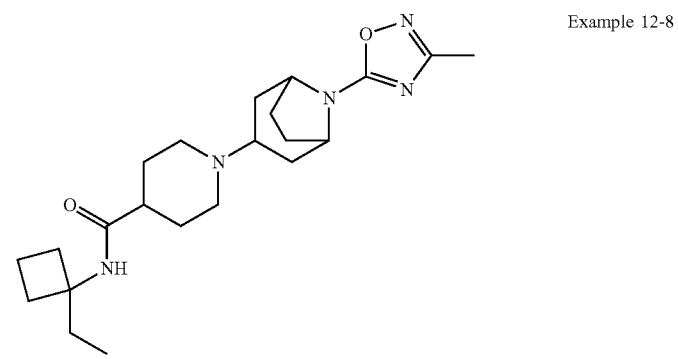
Example 12-8

TABLE 1-continued
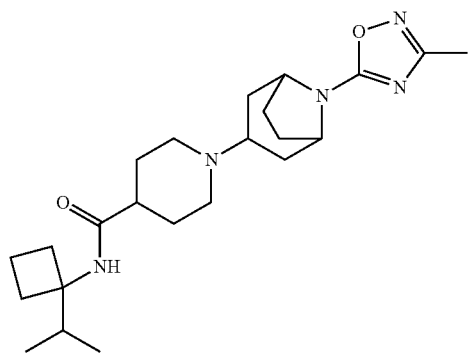 [SMILES: Cc1noc(N2C3CCC2CC(N2CCC(C(=O)NC4(C(C)C)CCC4)CC2)C3)n1]
Example 12-9
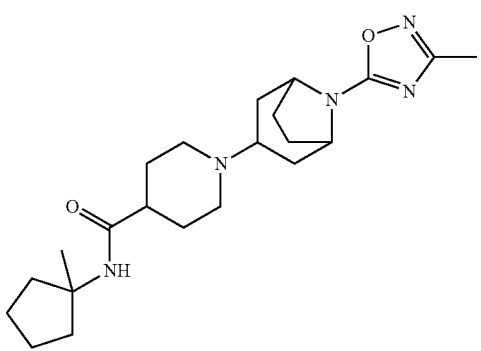 [SMILES: Cc1noc(N2C3CCC2CC(N2CCC(C(=O)NC4(C)CCCC4)CC2)C3)n1]
Example 12-11
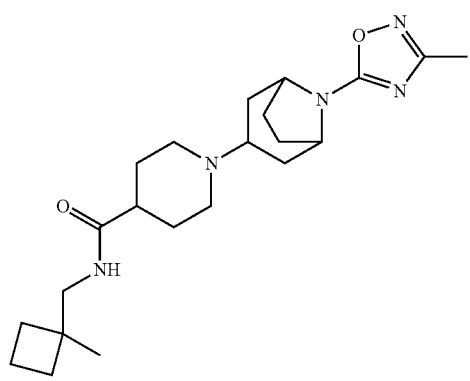 [SMILES: Cc1noc(N2C3CCC2CC(N2CCC(C(=O)NCC4(C)CCC4)CC2)C3)n1]
Example 12-12
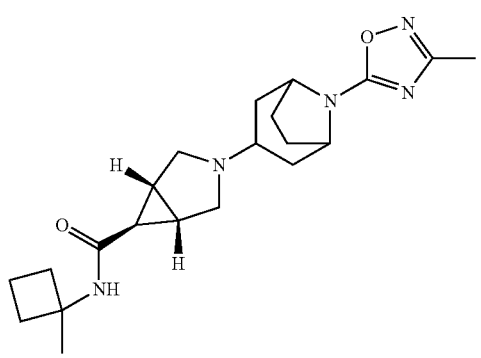 [SMILES: Cc1noc(N2C3CCC2CC(N2C[C@@H]4[C@H](C2)[C@H]4C(=O)NC2(C)CCC2)C3)n1]
Example 12-13

TABLE 1-continued
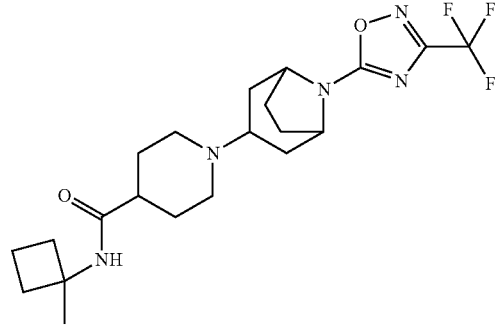 [SMILES: CC1(NC(=O)C2CCN(C3CC4CCC(C3)N4c3nc(C(F)(F)F)no3)CC2)CCC1]
Example 12-14
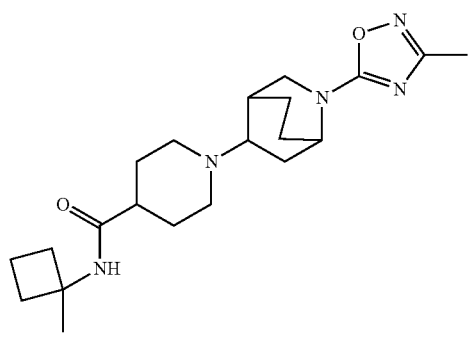 [SMILES: Cc1noc(N2CC3CCC2CC3N2CCC(C(=O)NC3(C)CCC3)CC2)n1]
Example 12-15
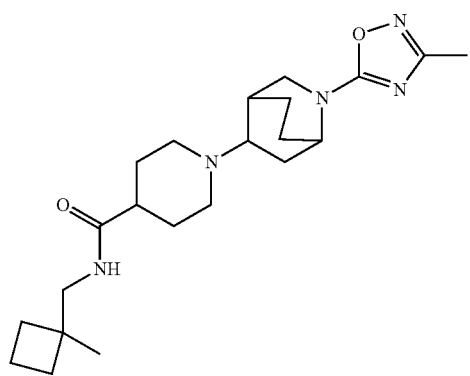 [SMILES: Cc1noc(N2CC3CCC2CC3N2CCC(C(=O)NCC3(C)CCC3)CC2)n1]
Example 12-16
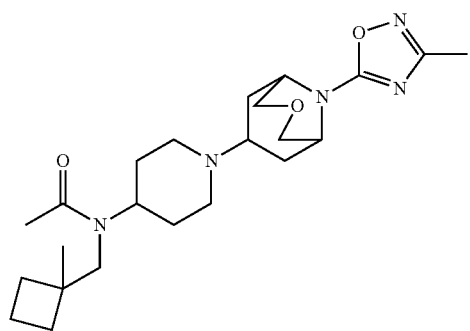 [SMILES: CC(=O)N(CC1(C)CCC1)C1CCN(C2CC3COCC(C2)N3c2nc(C)no2)CC1]
Example 12-17

TABLE 1-continued
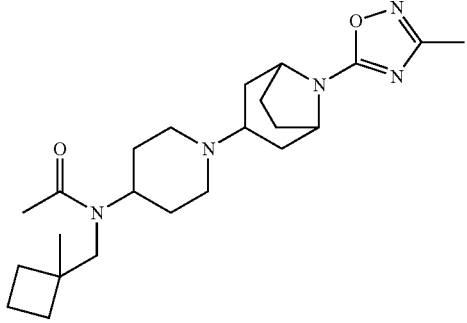 [SMILES: CC(=O)N(CC1(C)CCC1)C1CCN(C2CC3CCC(C2)N3c2nc(C)no2)CC1]
Example 12-18
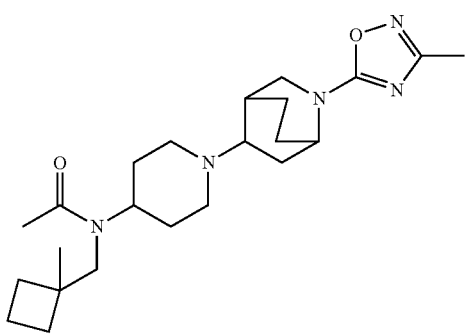 [SMILES: CC(=O)N(CC1(C)CCC1)C1CCN(C2CC3CCC2CN3c2nc(C)no2)CC1]
Example 12-19
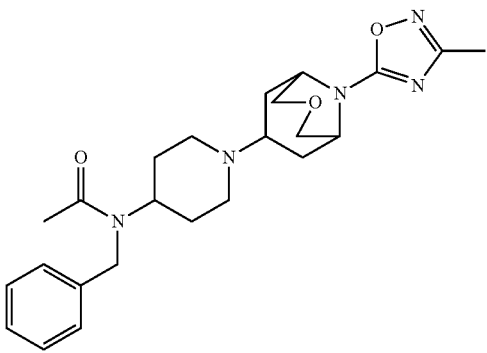 [SMILES: CC(=O)N(Cc1ccccc1)C1CCN(C2CC3COCC(C2)N3c2nc(C)no2)CC1]
Example 12-20
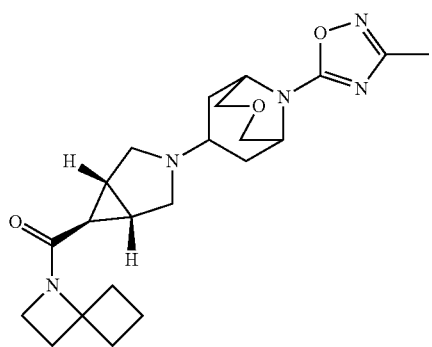 [SMILES: Cc1noc(N2C3COCC2CC(N2C[C@@H]4[C@H](C2)[C@H]4C(=O)N2CCC24CCC4)C3)n1]
Example 12-21

TABLE 1-continued
| | |
|---|---|
| 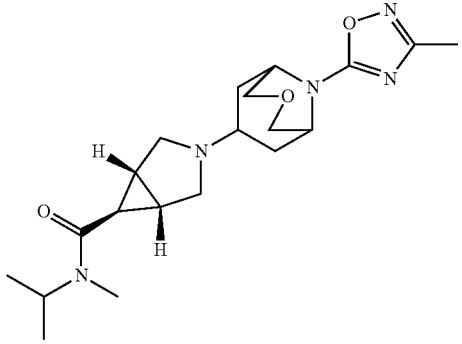 [SMILES: Cc1noc(N2C3COCC2CC(N2C[C@@H]4[C@H](C2)[C@H]4C(=O)N(C)C(C)C)C3)n1] | Example 12-22 |
| 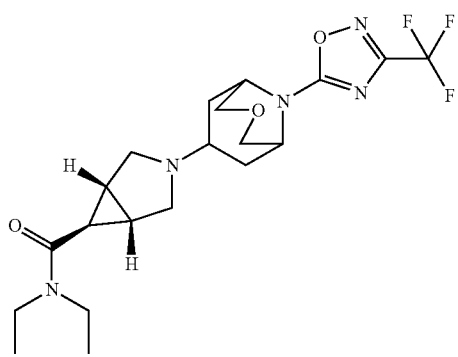 [SMILES: CCN(CC)C(=O)[C@H]1[C@@H]2CN(C3CC4COCC(C3)N4c3nc(C(F)(F)F)no3)C[C@@H]21] | Example 12-23 |
| 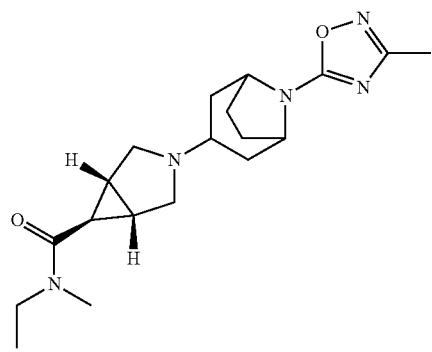 [SMILES: CCN(C)C(=O)[C@H]1[C@@H]2CN(C3CC4CCC(C3)N4c3nc(C)no3)C[C@@H]21] | Example 12-24 |
| 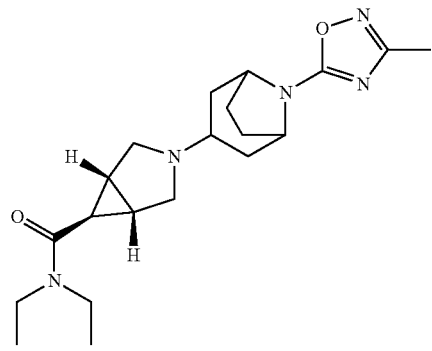 [SMILES: CCN(CC)C(=O)[C@H]1[C@@H]2CN(C3CC4CCC(C3)N4c3nc(C)no3)C[C@@H]21] | Example 12-25 |

TABLE 1-continued
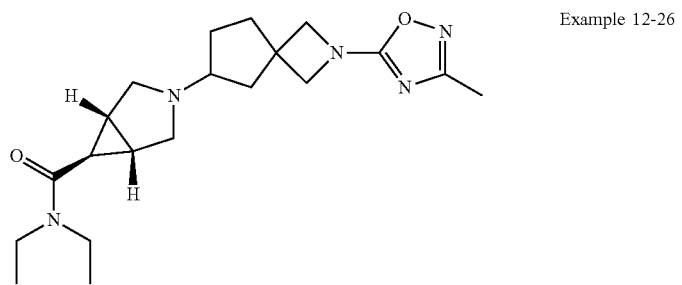
Example 12-26
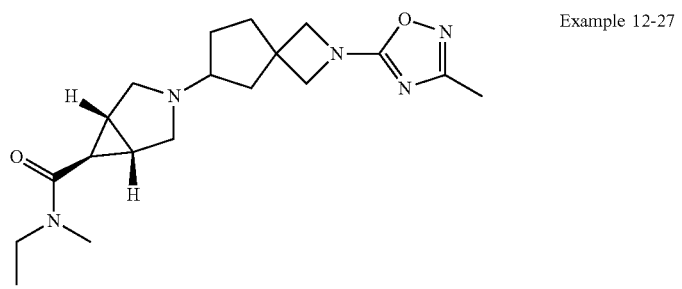
Example 12-27
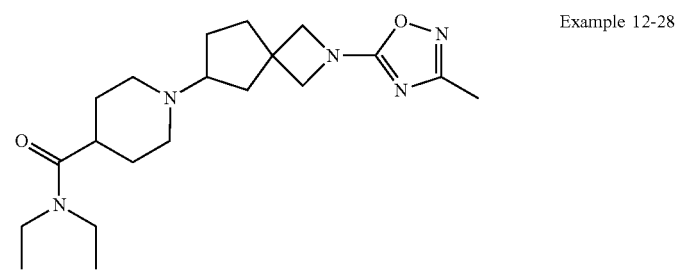
Example 12-28
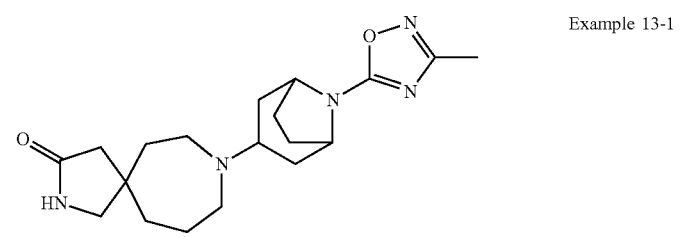
Example 13-1
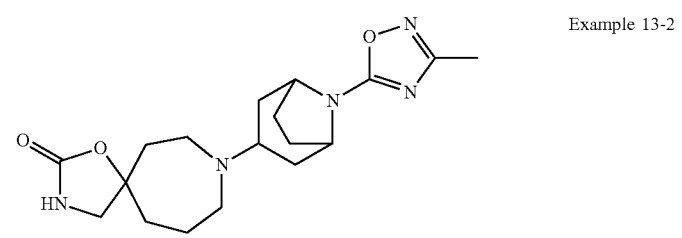
Example 13-2
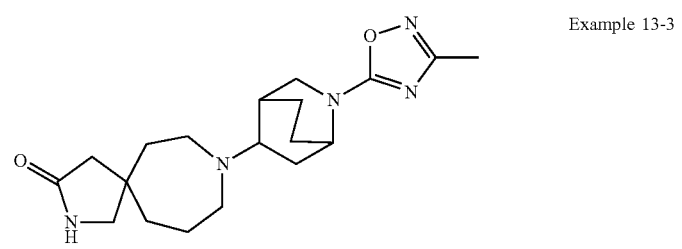
Example 13-3

TABLE 1-continued
| | |
|---|---|
| 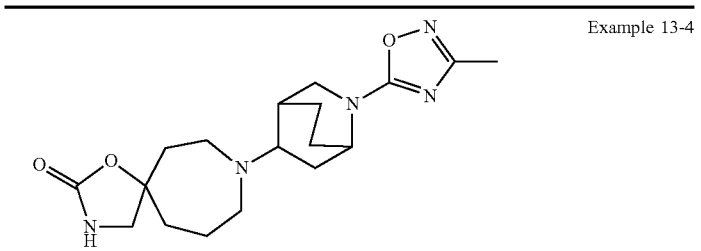 | Example 13-4 |
| 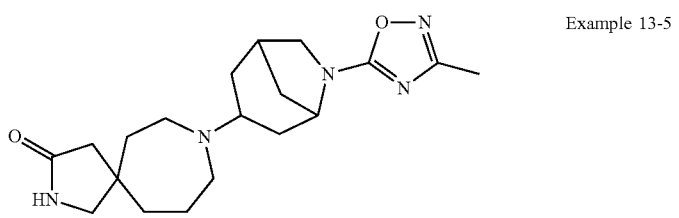 | Example 13-5 |
| 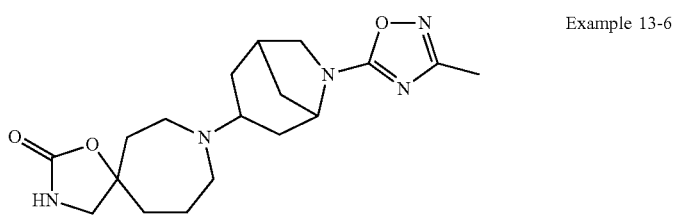 | Example 13-6 |
| 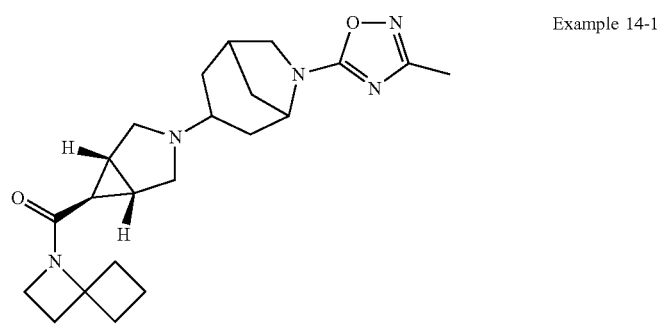 | Example 14-1 |
| 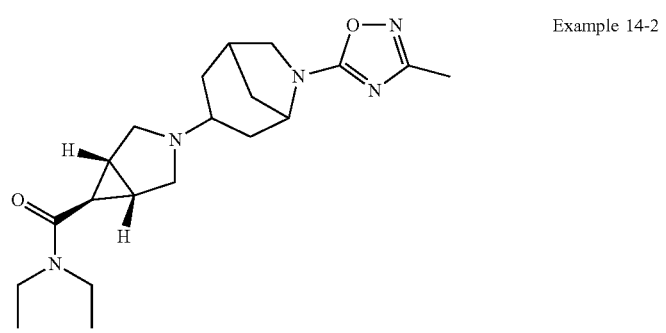 | Example 14-2 |
| 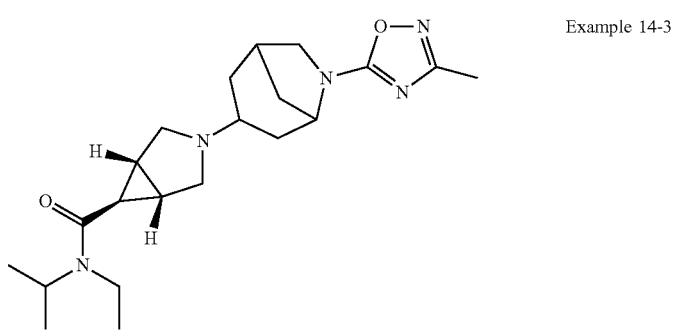 | Example 14-3 |

TABLE 1-continued
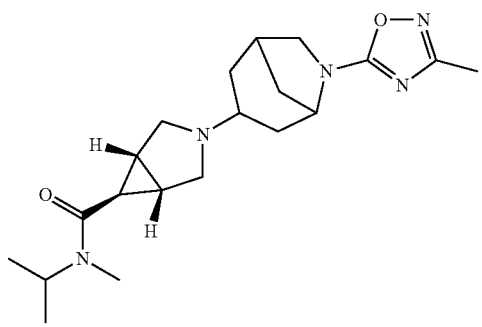 [SMILES: Cc1noc(N2CC3CC(N4C[C@@H]5[C@H](C4)[C@H]5C(=O)N(C)C(C)C)CC2C3)n1]
Example 14-4
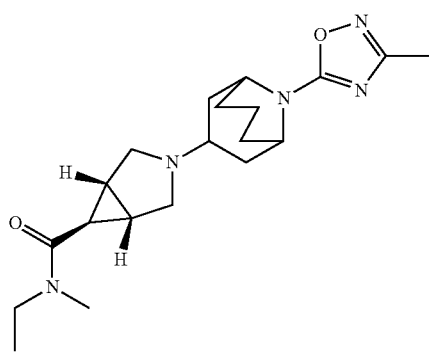 [SMILES: CCN(C)C(=O)[C@H]1[C@@H]2CN(C3CC4CCCC(C3)N4c3nc(C)no3)C[C@@H]21]
Example 14-5
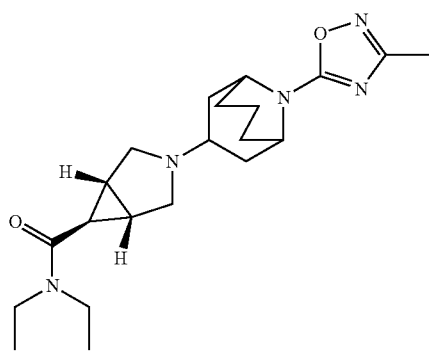 [SMILES: CCN(CC)C(=O)[C@H]1[C@@H]2CN(C3CC4CCCC(C3)N4c3nc(C)no3)C[C@@H]21]
Example 14-6
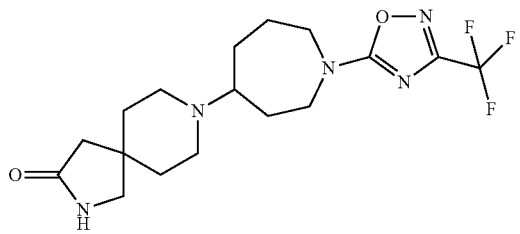 [SMILES: O=C1NCC2(CCN(C3CCCN(c4nc(C(F)(F)F)no4)CC3)CC2)O1]
Example 15-1
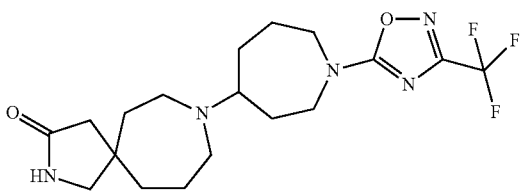 [SMILES: O=C1NCC2(CCCN(C3CCCN(c4nc(C(F)(F)F)no4)CC3)CC2)O1]
Example 15-2

TABLE 1-continued
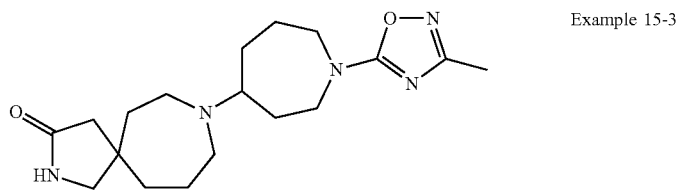 Example 15-3
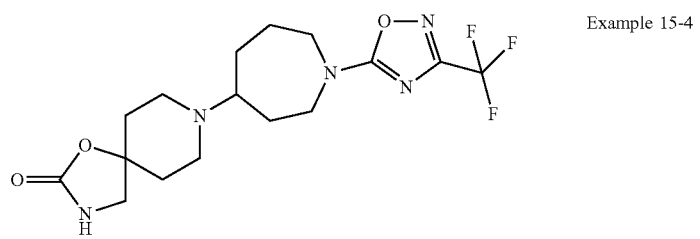 Example 15-4
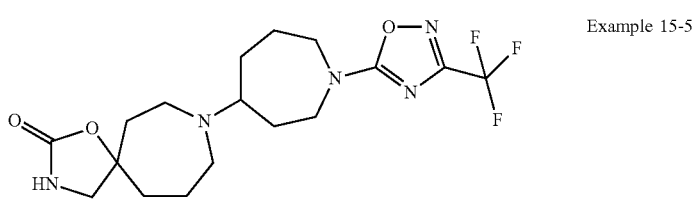 Example 15-5
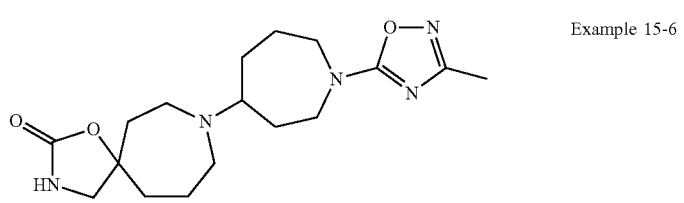 Example 15-6
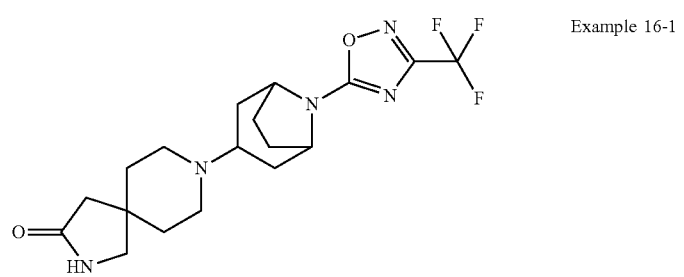 Example 16-1
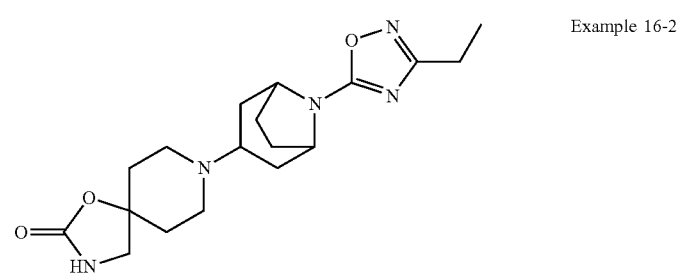 Example 16-2
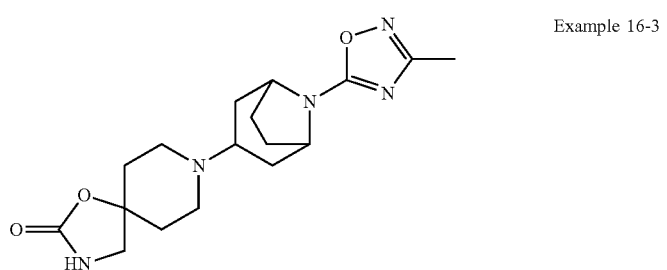 Example 16-3

TABLE 1-continued
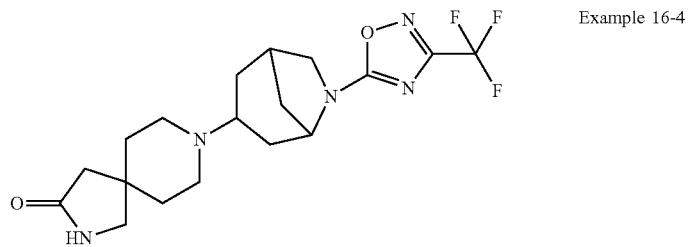
Example 16-4
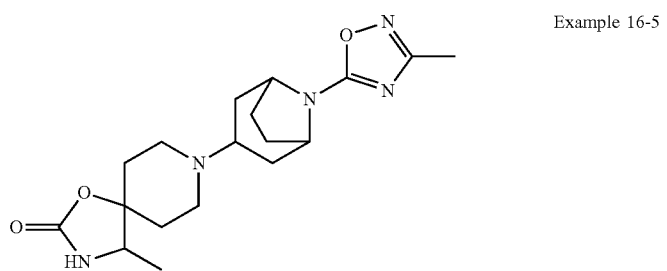
Example 16-5
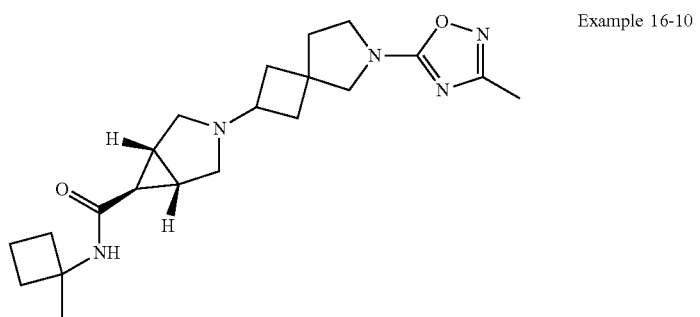
Example 16-10
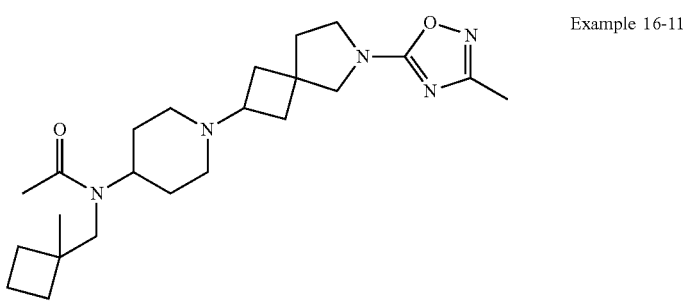
Example 16-11
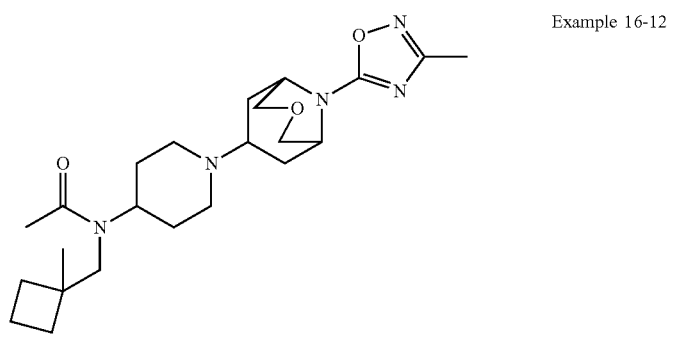
Example 16-12

TABLE 1-continued
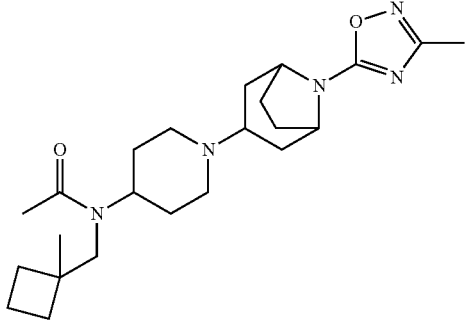 [SMILES: CC(=O)N(CC1(C)CCC1)C1CCN(C2CC3CCC(C2)N3c2nc(C)no2)CC1]
Example 16-13
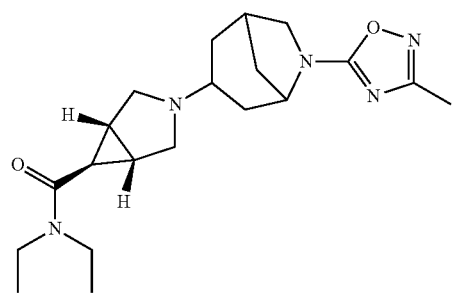 [SMILES: CCN(CC)C(=O)[C@H]1[C@@H]2CN(C3CC4CC(C3)N(c3nc(C)no3)C4)C[C@@H]21]
Example 16-14
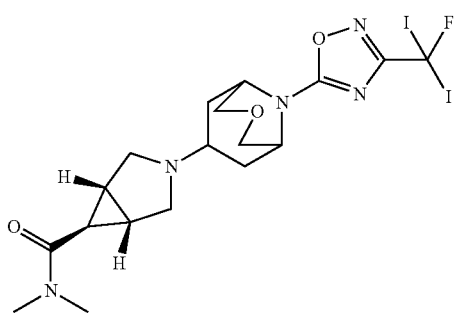 [SMILES: CN(C)C(=O)[C@H]1[C@@H]2CN(C3CC4COCC(C3)N4c3nc(C(F)(I)I)no3)C[C@@H]21]
Example 16-15
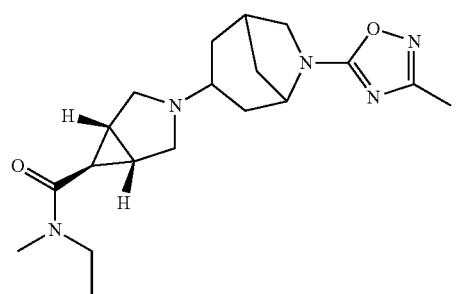 [SMILES: CCN(C)C(=O)[C@H]1[C@@H]2CN(C3CC4CC(C3)N(c3nc(C)no3)C4)C[C@@H]21]
Example 16-16
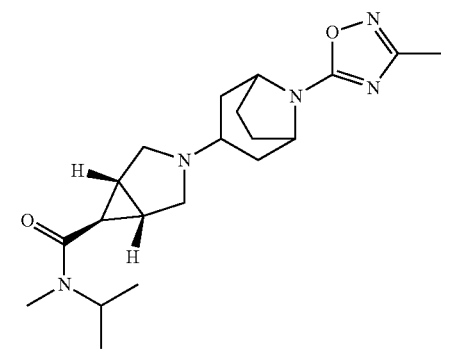 [SMILES: Cc1noc(N2C3CCC2CC(N2C[C@@H]4[C@H](C2)[C@H]4C(=O)N(C)C(C)C)C3)n1]
Example 16-17

TABLE 1-continued
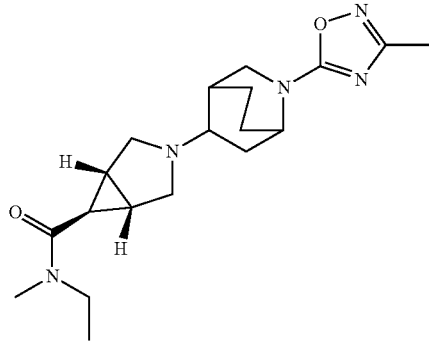 [SMILES: CCN(C)C(=O)[C@H]1[C@@H]2CN(C3CC4CCC3CN4c3nc(C)no3)C[C@@H]21]
Example 16-18
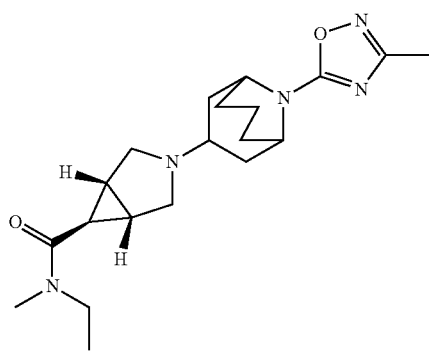 [SMILES: CCN(C)C(=O)[C@H]1[C@@H]2CN(C3CC4CCCC(C3)N4c3nc(C)no3)C[C@@H]21]
Example 16-19
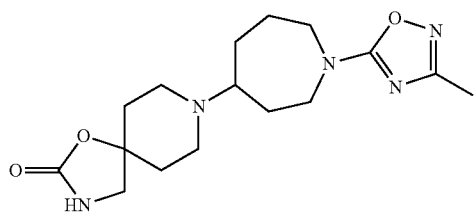 [SMILES: Cc1noc(N2CCCC(N3CCC4(CC3)CNC(=O)O4)CC2)n1]
Example 17-1
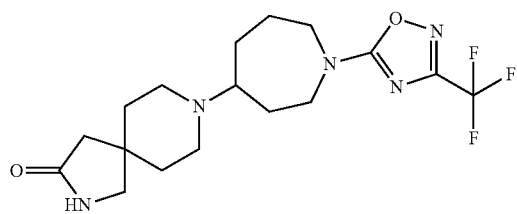 [SMILES: O=C1CC2(CCN(C3CCCN(c4nc(C(F)(F)F)no4)CC3)CC2)CN1]
Example 17-2
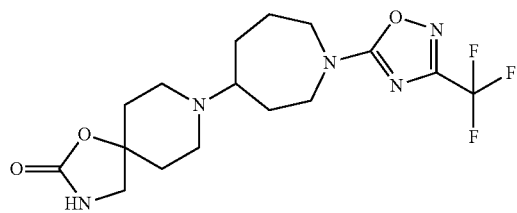 [SMILES: O=C1NCC2(CCN(C3CCCN(c4nc(C(F)(F)F)no4)CC3)CC2)O1]
Example 17-3
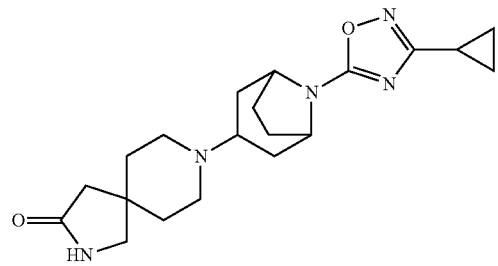 [SMILES: O=C1CC2(CCN(C3CC4CCC(C3)N4c3nc(C4CC4)no3)CC2)CN1]
Example 17-4

TABLE 1-continued
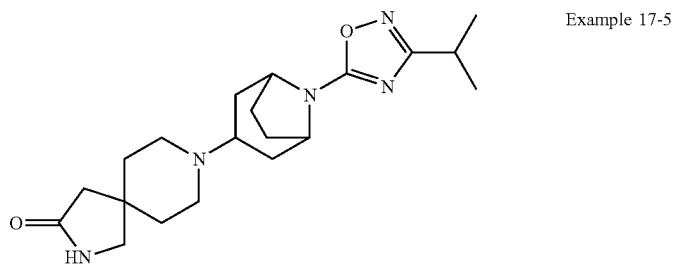
Example 17-5
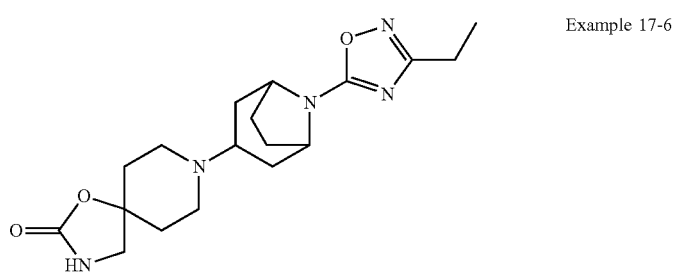
Example 17-6
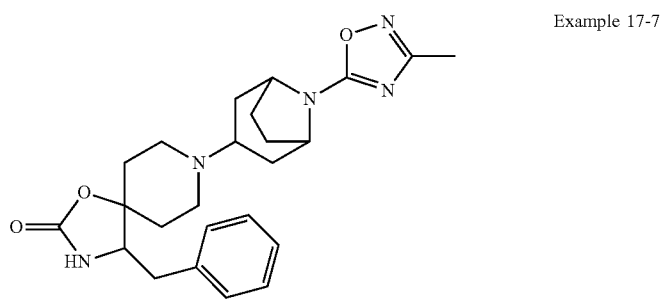
Example 17-7
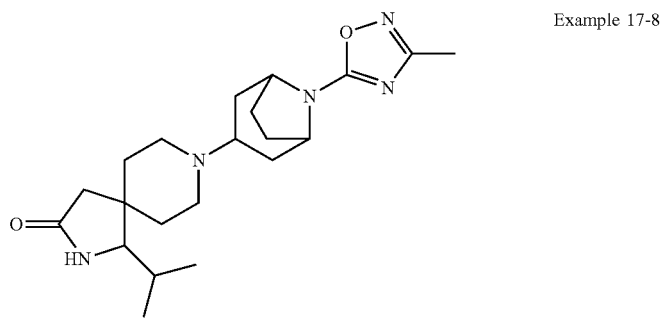
Example 17-8
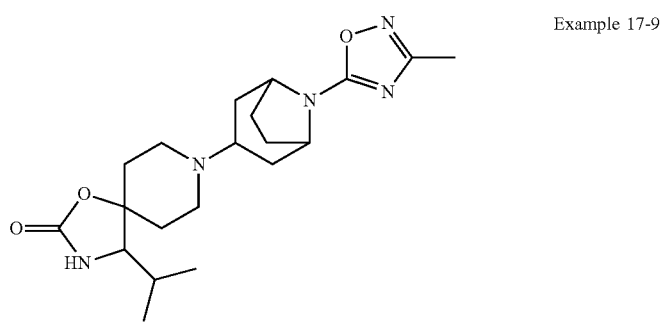
Example 17-9

TABLE 1-continued
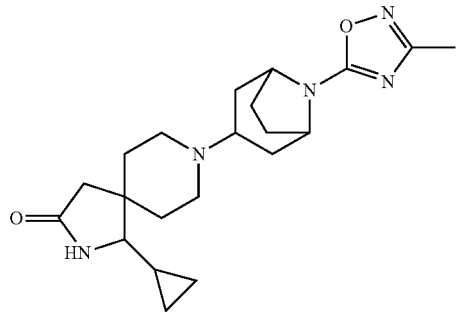 [SMILES: Cc1noc(N2C3CCC2CC(N2CCC4(CC2)CC(=O)NC4C2CC2)C3)n1]
Example 17-10
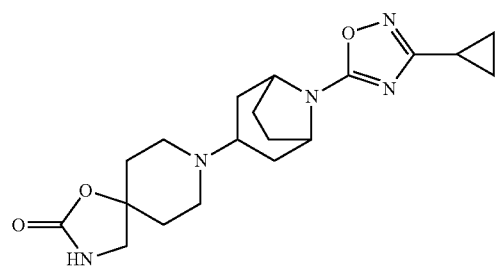 [SMILES: O=C1NCC2(CCN(C3CC4CCC(C3)N4c3nc(C4CC4)no3)CC2)O1]
Example 17-11
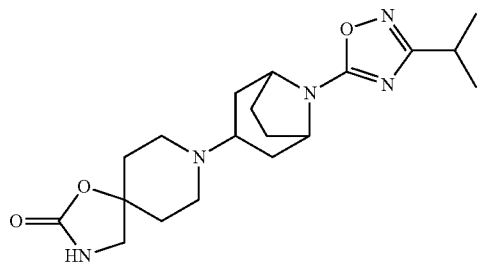 [SMILES: CC(C)c1noc(N2C3CCC2CC(N2CCC4(CC2)CNC(=O)O4)C3)n1]
Example 17-12
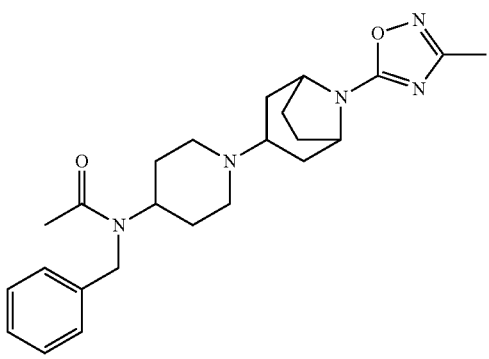 [SMILES: CC(=O)N(Cc1ccccc1)C1CCN(C2CC3CCC(C2)N3c2nc(C)no2)CC1]
Example 17-13
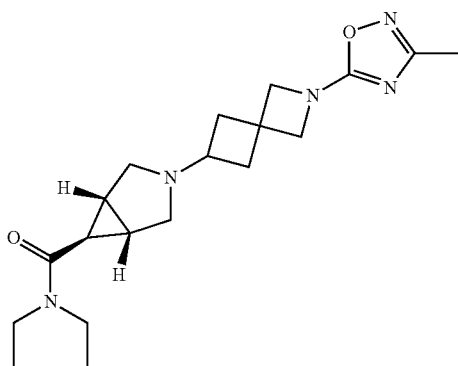 [SMILES: CCN(CC)C(=O)[C@H]1[C@@H]2CN(C3CC4(C3)CN(c3nc(C)no3)C4)C[C@@H]21]
Example 17-14

TABLE 1-continued
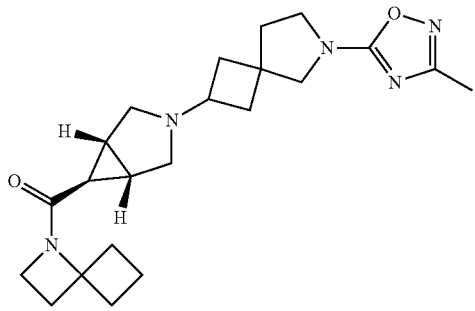 [SMILES: Cc1noc(N2CCC3(CC(N4C[C@@H]5[C@H](C4)[C@H]5C(=O)N4CCC45CCC5)C3)C2)n1]
Example 17-15
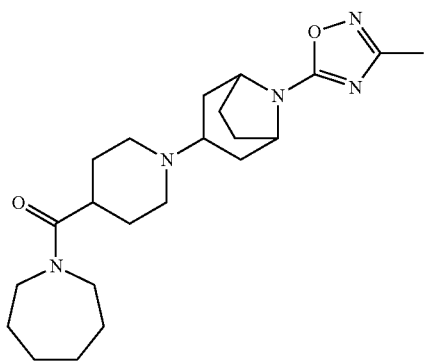 [SMILES: Cc1noc(N2C3CCC2CC(N2CCC(C(=O)N4CCCCCC4)CC2)C3)n1]
Example 17-16
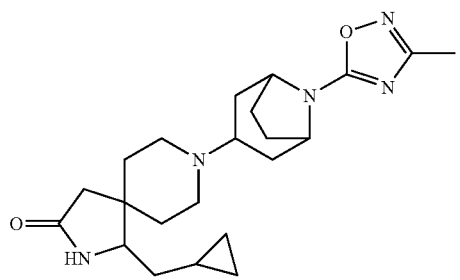 [SMILES: Cc1noc(N2C3CCC2CC(N2CCC4(CC2)CC(=O)NC4CC2CC2)C3)n1]
Example 17-17
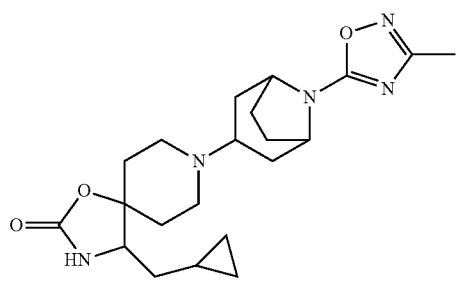 [SMILES: Cc1noc(N2C3CCC2CC(N2CCC4(CC2)OC(=O)NC4CC2CC2)C3)n1]
Example 17-18
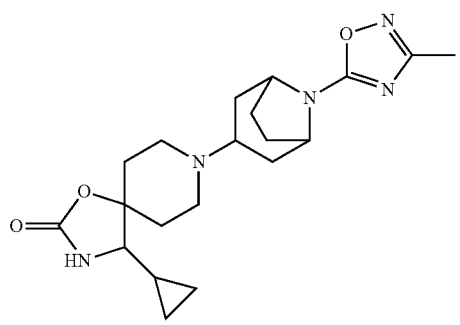 [SMILES: Cc1noc(N2C3CCC2CC(N2CCC4(CC2)OC(=O)NC4C2CC2)C3)n1]
Example 17-19

TABLE 1-continued
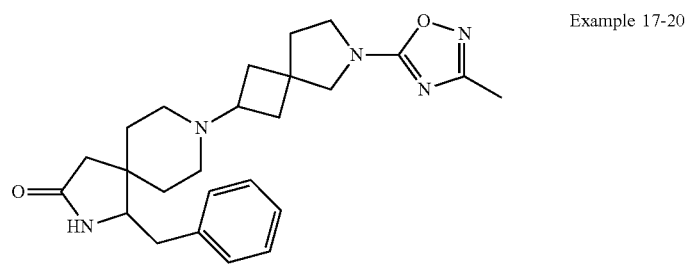
Example 17-20
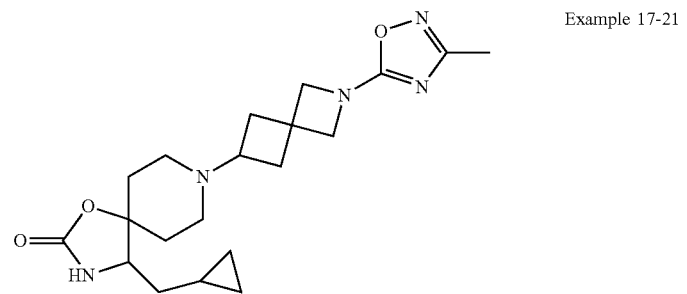
Example 17-21
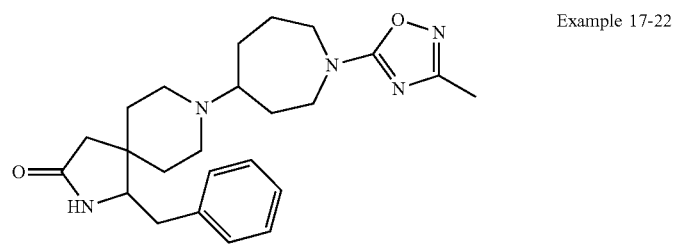
Example 17-22
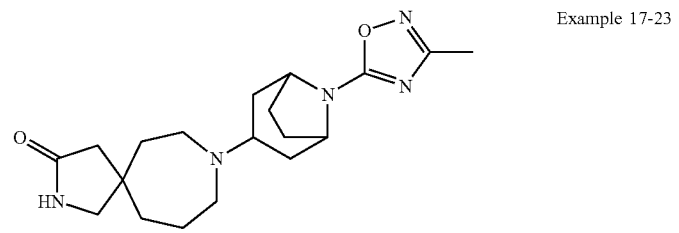
Example 17-23
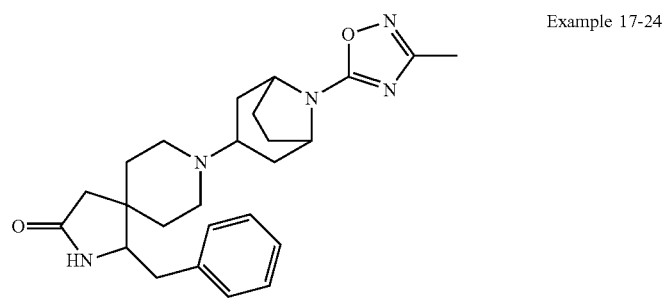
Example 17-24
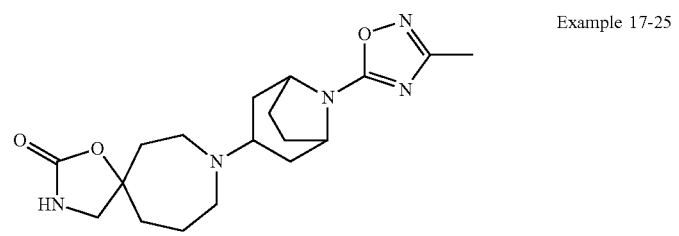
Example 17-25

TABLE 1-continued

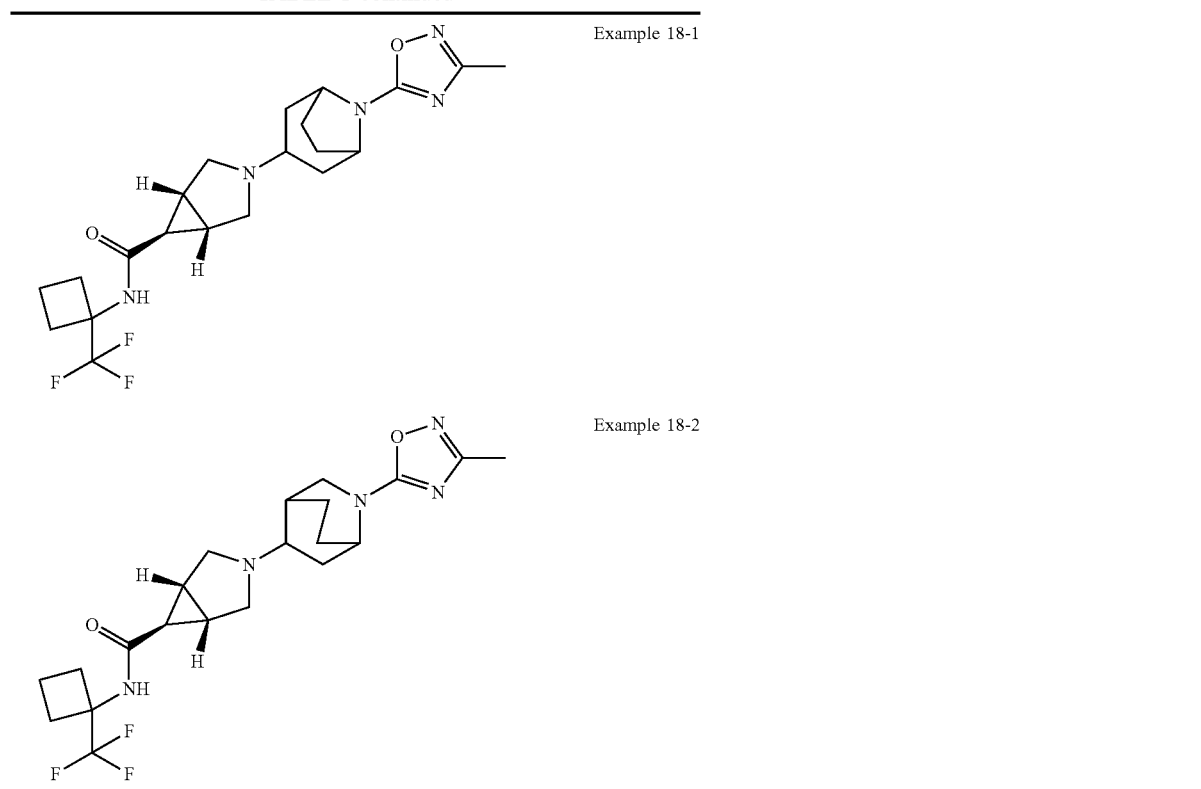

Example 18-1

Example 18-2

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and the Silica gel F254 as a stationary phase from Merck. Microwave-mediated reactions were performed in Biotage Initiator or CEM Discover microwave reactors.

LCMS Analysis

LCMS analysis of compounds was performed under electrospray conditions using the instruments and methods given in the tables below:

| System | Instrument Name | LC Detector | Mass Detector |
|---|---|---|---|
| 1 | Waters 2695 | Photo Diode Array | ZQ-2000 Detector |
| 2 | Waters Acquity H Class | Photo Diode Array | SQ Detector |
| 3 | Shimadzu Nexera | Photo Diode Array | LCMS-2020 |
| 4 | Agilent 1290 RRLC | Photo Diode Array | Agilent 6120 |
| 5 | Hewlett Packard HP 1100 | G1315A DAD | Micromass ZQ |

| Method Name | Solvent System | Column used | Gradient | UV Range | Mass Range | Column Temp. ° C. | Flow Rate ml/min |
|---|---|---|---|---|---|---|---|
| A | (A) 2 mM ammonium acetate + 0.1% formic acid in water (B) 0.1% formic acid in acetonitrile | BEH C18 2.1 × 50 mm, 1.7 μm or equivalent | 98:2 at 0.01 min up to 0.30 min, 50:50 at 0.60 min, 25:75 at 1.10 min, 0:100 at 2.00 min up to 2.70 min, 98:2 at 2.71 min up to 3.00 min | 200-400 nm | 100-1200 amu | Ambient | 0.55 |

-continued

| Method Name | Solvent System | Column used | Gradient | UV Range | Mass Range | Column Temp. ° C. | Flow Rate ml/min |
|---|---|---|---|---|---|---|---|
| B | (A) 20 mM ammonium acetate in water (B) methanol | X-Bridge C18 4.6 × 150 mm, 5 μm or equivalent | 90:10 at 0.01 min, 10:90 at 5.00 min, 0:100 at 7.00 min up to 11.00 min, 90:10 at 11.01 min up to 12.00 min | 200-400 nm | 60-1000 amu | Ambient | 1.00 |
| C | (A) 10 mM ammonium acetate in water (B) acetonitrile | YMC Triart C18 4.6 × 150 mm, 5 μm or equivalent | 100:0 at 0.01 min, 50:50 at 7.00 min, 0:100 at 9.00 min up to 11.00 min, 100:0 at 11.01 min up to 12.00 min | 200-400 nm | 60-1000 amu | Ambient | 1.00 |
| D | (A) 0.1% ammonia in water (B) 0.1% ammonia in acetonitrile | X-Bridge C18 4.6 × 50 mm, 3.5 μm or equivalent | 95:5 at 0.01 min, 10:90 at 5.00 min, 5:95 at 5.80 min up to 7.20 min, 95:5 at 7.21 min up to 10.00 min | 200-400 nm | 60-1000 amu | Ambient | 1.00 |
| E | (A) 5 mM ammonium acetate + 0.1% formic acid in water (B) 0.1% formic acid in acetonitrile | BEH C18 2.1 × 50 mm, 1.7 μm or equivalent | 95:5 at 0.01 min up to 0.40 min, 60:40 at 0.60 min, 40:60 at 1.20 min, 0:100 at 2.30 min up to 3.00 min, 95:5 at 3.01 min up to 3.50 min | 200-400 nm | 100-1200 amu | Ambient | 0.55 |
| F | (A) 5 mM ammonium bicarbonate in water (B) acetonitrile | X-Bridge C18 4.6 × 50 mm, 3.5 μm or equivalent | 95:5 at 0.01 min, 10:90 at 5.00 min, 5:95 at 5.80 min up to 7.20 min, 95:5 at 7.21 min up to 10.00 min | 200-400 nm | 60-1000 amu | Ambient | 1.00 |
| G | (A) 2.5 L water + 2.5 mL 28% ammonia solution in water B) 2.5 L acetonitrile + 135 mL water + 2.5 mL 28% ammonia solution in water | Gemini-NX C-18, 2.0 × 30 mm, 3 μm | 98:2 at 0.00 min up to 0.10 min, 5:95 at 8.40 min up to 10.00 min | 230-400 nm | 130-800 amu | 45 | 1.50 |
| H | (A) 2 mM ammonium acetate + 0.1% formic acid in water (B) 0.1% formic acid in acetonitrile | BEH C18 2.1 × 50 mm, 1.7 μm or equivalent | 98:2 at 0.01 min up to 0.30 min (flow rate 0.55), 50:50 at 0.60 min (flow rate 0.55), 25:75 at 1.10 min (flow rate 0.55), 0:100 at 2.00 min up to 2.70 min (flow rate 0.60), 98:2 at 2.71 min up to 3.00 min (flow rate 0.55) | 200-400 nm | 100-1200 amu | Ambient | 0.55-0.60 |

LCMS data in the experimental section and Tables 2 and 3 are given in the format: (Instrument system, Method): Mass ion, retention time, UV detection wavelength.

Compound Purification

Final purification of compounds was performed by preparative reversed phase HPLC, chiral HPLC or chiral SFC using the instruments and methods detailed below where data is given in the following format: Purification technique: [phase (column description, column length×internal diameter, particle size), solvent flow-rate, gradient—given as % of mobile phase B in mobile phase A (over time), mobile phase (A), mobile phase (B)].

Preparative HPLC Purification:
Shimadzu LC-20AP binary system with SPD-20A UV detector
Chiral HPLC Purification:
Shimadzu LC-20AP binary system with SPD-20A UV detector
Chiral SFC Purification:
Waters SFC 200
Sepiatec 100
Berger Multigram 2
Purification Method A
Prep HPLC: [Reversed Phase (X SELECT PHENYL HEXYL, 250×19 mm, 5 μm), 15 mL/min, gradient 10%-40% (over 23 min), 100% (over 2 min), 100%-10% (over 4 min), mobile phase (A): 5 mM ammonium bicarbonate in water+0.1% ammonia in water, (B): 100% acetonitrile].

Purification Method B
Prep HPLC: [Reversed Phase (X-BRIDGE C-8, 250×19 mm, 5 μm), 15 mL/min, gradient 10%-33% (over 25 min), 100% (over 2 min), 10% (over 3 min), mobile phase (A): 5 mM ammonium bicarbonate in water+0.1% ammonia in water, (B): 100% acetonitrile].

Purification Method C
Prep HPLC: [Reversed Phase (X-BRIDGE C-18, 250×19 mm, 5 μm), 15 mL/min, gradient 37%-40% (over 23 min), 100% (over 2 min), 37% (over 2 min), mobile phase (A): 5 mM ammonium bicarbonate in water+0.1% ammonia in water, (B): 100% acetonitrile].

Purification Method D
Prep HPLC: [Reversed Phase (X-BRIDGE C-8, 250×19 mm, 5 μm), 15 mL/min, gradient 30%-40% (over 20 min), 100% (over 2 min), 100-30% (over 3 min), mobile phase (A): 5 mM ammonium bicarbonate in water+0.1% ammonia in water, (B): 100% acetonitrile].

Purification Method E
Prep HPLC: [Reversed Phase (X-BRIDGE C-8, 250×19 mm, 5 μm), 15 mL/min, gradient 5%-40% (over 20 min), 40% (over 3 min), 100% (over 2 min), 100-5% (over 2 min), mobile phase (A): 5 mM ammonium bicarbonate in water+0.1% ammonia in water, (B): 100% acetonitrile].

Purification Method F

Prep HPLC: [Reversed Phase (X SELECT PHENYL HEXYL, 250×19 mm, 5 μm), 5 mL/min, gradient 15%-47% (over 15 min), 100% (over 1 min), 10% (over 3 min), mobile phase (A): 5 mM ammonium bicarbonate in water+0.1% ammonia in water, (B): 100% acetonitrile].

Purification Method G

Prep HPLC: [Reversed Phase (X-BRIDGE C-8, 250×19 mm, 5 μm), 15 mL/min, gradient 5%-50% (over 17 min), 50-70% (over 2 min), 100% (over 3 min), 100-5% (over 3 min), mobile phase (A): 5 mM ammonium bicarbonate in water+0.1% ammonia in water, (B): 100% acetonitrile].

Purification Method H

Prep HPLC: [Reversed Phase (X-BRIDGE C-8, 250×19 mm, 5 μm), 16 mL/min, gradient 15%-42% (over 20 min), 100% (over 2 min), 100%-15% (over 3 min), mobile phase (A): 5 mM ammonium bicarbonate in water+0.1% ammonia in water, (B): 100% acetonitrile].

Purification Method I

Prep HPLC: [Reversed Phase (X-BRIDGE C-18, 250×19 mm, 5 μm), 16 mL/min, gradient 5%-30% (over 19 min), 100% (over 3 min), 100%-5% (over 4 min), mobile phase (A): 5 mM ammonium bicarbonate in water+0.1% ammonia in water, (B): 100% acetonitrile].

Purification Method J

Prep HPLC: [Reversed Phase (X-BRIDGE C-18, 250×19 mm, 5 μm), 10 mL/min, gradient 0%-30% (over 45 min), 30-30% (over 48 min), 100% (over 2 min), 100%-0% (over 3 min), mobile phase (A): 5 mM ammonium bicarbonate in water+0.1% ammonia in water, (B): 100% acetonitrile].

Purification Method K

Prep HPLC: [Reversed Phase (X-BRIDGE C-8, 250×19 mm, 5 μm), 15 mL/min, gradient 5%-38% (over 25 min), 100% (over 2 min), 100-5% (over 5 min), mobile phase (A): 5 mM ammonium bicarbonate in water+0.1% ammonia in water, (B): 100% acetonitrile].

Purification Method L

Prep HPLC: [Reversed Phase (X-BRIDGE C-18, 250×19 mm, 5 μm), 16 mL/min, gradient 20%-30% (over 25 min), 30-30% (over 5 min), 100% (over 3 min), 100%-20% (over 5 min), mobile phase (A): 5 mM ammonium bicarbonate in water+0.1% ammonia in water, (B): 100% acetonitrile].

Purification Method M

Prep HPLC: [Reversed Phase (X SELECT PHENYL HEXYL, 250×19 mm, 5 μm), 15 mL/min, gradient 15%-30% (over 30 min), 30-30% (over 6 min), 100% (over 2 min), 100-15% (over 4 min), mobile phase (A): 5 mM ammonium bicarbonate in water+0.1% ammonia in water, (B): 100% acetonitrile].

Purification Method N

Prep HPLC: [Reversed Phase (X SELECT PHENYL HEXYL, 250×19 mm, 5 μm), 15 mL/min, gradient 25%-35% (over 23 min), 100% (over 1 min), 100-25% (over 4 min), mobile phase (A): 5 mM ammonium bicarbonate in water+0.1% ammonia in water, (B): 100% acetonitrile].

Purification Method O

Chiral HPLC: [Normal Phase (CHIRALPAK AD-H, 250×21 mm, 5 μm), 18 mL/min, Isochratic (A:B) 45:55 (over 45 min), mobile phase (A): 0.1% diethylamine in hexane, (B): 0.1% diethylamine in isopropanol:methanol (30:70)].

Purification Method P

Prep HPLC: [Reversed Phase (X-BRIDGE C-18, 250×19 mm, 5 μm), 13 mL/min, gradient 15%-20% (over 30 min), 20-20% (over 6 min), 100% (over 1 min), 100%-15% (over 6 min), mobile phase (A): 5 mM ammonium bicarbonate in water+0.1% ammonia in water, (B): 100% acetonitrile].

Purification Method Q

Prep HPLC: [Reversed Phase (X-BRIDGE C-18, 250×19 mm, 5 μm), 15 mL/min, gradient 5%-17% (over 32 min), 17-17% (over 58 min), 100% (over 3 min), 100%-5% (over 4 min), mobile phase (A): 5 mM ammonium bicarbonate in water+0.1% ammonia in water, (B): 100% acetonitrile].

Purification Method R

Prep HPLC: [Reversed Phase (X-BRIDGE C-8, 250×19 mm, 5 μm), 15 mL/min, gradient 20%-35% (over 25 min), 35-35% (over 3 min), 100% (over 2 min), 100-20% (over 3 min), mobile phase (A): 5 mM ammonium bicarbonate in water+0.1% ammonia in water, (B): 100% acetonitrile].

Purification Method S

SFC: [(CHIRALCEL OX-H, 250×21 mm, 5 μm), 70 mL/min, Isochratic (A:B) 70:30 (over 8.5 min), mobile phase (A): 100% liquid $CO_2$, (B): 0.1% diethylamine in isopropanol:methanol (50:50)].

Purification Method T

Prep HPLC: [Reversed Phase (X-BRIDGE C-8, 250×19 mm, 5 μm), 15 mL/min, gradient 18%-30% (over 18 min), 100% (over 2 min), 100-18% (over 2 min), mobile phase (A): 5 mM ammonium bicarbonate in water+0.1% ammonia in water, (B): 100% acetonitrile].

Purification Method U

Chiral HPLC: [Normal Phase (CHIRALCEL OX-H, 250×21 mm, 5 μm), 18 mL/min, Isochratic (A:B) 90:10 (over 32 min), mobile phase (A): 0.1% diethylamine in hexane, (B): 0.1% diethylamine in isopropanol:acetonitrile (70:30)].

Purification Method V

Prep HPLC: [Reversed Phase (X-BRIDGE C-18, 250×19 mm, 5 μm), 15 mL/min, gradient 10%-25% (over 25 min), 25-25% (over 7 min), 100% (over 2 min), 100%-10% (over 2 min), mobile phase (A): 5 mM ammonium bicarbonate in water+0.1% ammonia in water, (B): 100% acetonitrile].

Purification Method W

Prep HPLC: [Reversed Phase (X SELECT PHENYL HEXYL, 250×19 mm, 5 μm), 15 mL/min, gradient 25%-40% (over 15 min), 100% (over 3 min), 100%-25% (over 5 min), mobile phase (A): 0.1% ammonia in water, (B): 100% acetonitrile].

Purification Method X

SFC: [(LUX A1, 250×21.2 mm, 5 μm), 50 mL/min, Isochratic (A:B) 65:35, mobile phase (A): 100% liquid $CO_2$, (B): 0.1% ammonia in methanol].

Purification Method Y

Prep HPLC: [Reversed Phase (X-BRIDGE C-8, 250×19 mm, 5 μm), 15 mL/min, gradient 8%-20% (over 23 min), 20%-20% (over 2 min), 100% (over 2 min), 100%-8% (over 5 min), mobile phase (A): 5 mM ammonium bicarbonate in water+0.1% ammonia in water, (B): 100% acetonitrile].

Purification Method Z

SFC: [(CHIRALPAK AD-H, 250×21 mm, 5 μm), 75 mL/min, Isochratic (A:B) 82:18 (over 20 min), mobile phase (A): 100% liquid $CO_2$, (B): 0.1% diethylamine in methanol].

Purification Method AA

Prep HPLC: [Reversed Phase (X-BRIDGE C-8, 250×19 mm, 5 μm), 15 mL/min, gradient 8%-23% (over 17 min), 23%-23% (over 2 min), 100% (over 2 min), 100%-8% (over 4 min), mobile phase (A): 5 mM ammonium bicarbonate in water+0.1% ammonia in water, (B): 100% acetonitrile].

Purification Method AB

Prep HPLC: [Reversed Phase (YMC ACTUS TRIART C-18, 250×20 mm, 5 μm), 15 mL/min, gradient 15%-30% (over 28 min), 100% (over 2 min), 100%-15% (over 2 min), mobile phase (A): 5 mM ammonium bicarbonate in water+0.1% ammonia in water, (B): 100% acetonitrile].

Purification Method AC

SFC: [(CHIRALPAK AD-H, 250×21 mm, 5 μm), 75 mL/min, Isocratic (A:B) 75:25 (over 18 min), mobile phase (A): 100% liquid $CO_2$, (B): 0.1% diethylamine in methanol].

Purification Method AD

Prep HPLC: [Reversed Phase (X-BRIDGE C-18, 250×50 mm, 5 μm), 90 mL/min, gradient 5%-35% (over 20 min), 100% (over 2 min), 100%-5% (over 3 min), mobile phase (A): 5 mM ammonium bicarbonate in water+0.1% ammonia in water, (B): 100% acetonitrile].

Purification Method AE

Chiral HPLC: [Normal Phase (CHIRALPAK AD-H, 250×21 mm, 5 μm), 18 mL/min, Isocratic (A:B) 70:30 (over 35 min), mobile phase (A): 0.1% diethylamine in hexane, (B): 0.1% diethylamine in isopropanol:methanol (50:50)].

Purification Method AF

Prep HPLC: [Reversed Phase (X SELECT PHENYL HEXYL, 250×19 mm, 5 μm), 13 mL/min, gradient 15%-30% (over 30 min), 30%-30% (over 10 min), 100% (over 2 min), 100%-15% (over 3 min), mobile phase (A): 5 mM ammonium bicarbonate in water+0.1% ammonia in water, (B): 100% acetonitrile].

Purification Method AG

SFC: [(CHIRALPAK AD-H, 250×21 mm, 5 μm), 80 mL/min, Isocratic (A:B) 75:25 (over 13 min), mobile phase (A): 100% liquid $CO_2$, (B): 0.1% diethylamine in isopropanol:methanol (50:50)].

Purification Method AH

Prep HPLC: [Reversed Phase (X-BRIDGE C-18, 250×50 mm, 5 μm), 80 mL/min, gradient 5%-18% (over 50 min), 18%-18% (over 10 min), 100% (over 3 min), 100%-5% (over 7 min), mobile phase (A): 5 mM ammonium bicarbonate in water+0.1% ammonia in water, (B): 100% acetonitrile].

Purification Method AI

SFC: [(CHIRALPAK AD-H, 250×21 mm, 5 μm), 80 mL/min, Isocratic (A:B) 70:30 (over 20 min), mobile phase (A): 100% liquid $CO_2$, (B): 0.1% diethylamine in methanol].

Purification Method AJ

Prep HPLC: [Reversed Phase (X-BRIDGE C-8, 250×19 mm, 5 μm), 15 mL/min, gradient 0%-27% (over 28 min), 27%-27% (over 6 min), 100% (over 4 min), 100%-0% (over 2 min), mobile phase (A): 5 mM ammonium bicarbonate in water+0.1% ammonia in water, (B): 100% acetonitrile].

Purification Method AK

Chiral HPLC: [Normal Phase (CHIRALPAK AD-H, 250×21 mm, 5 μm), 18 mL/min, Isocratic (A:B) 90:10 (over 27 min), mobile phase (A): 0.1% diethylamine in hexane, (B): 0.1% diethylamine in isopropanol].

Purification Method AL

Prep HPLC: [Reversed Phase (X-BRIDGE C-8, 250×19 mm, 5 μm), 15 mL/min, gradient 15%-35% (over 20 min), 35%-35% (over 3 min), 100% (over 2 min), 100%-15% (over 3 min), mobile phase (A): 5 mM ammonium bicarbonate in water+0.1% ammonia in water, (B): 100% acetonitrile].

Purification Method AM

SFC: [(CHIRALPAK AD-H, 250×21 mm, 5 μm), 80 mL/min, Isocratic (A:B) 65:35 (over 16.5 min), mobile phase (A): 100% liquid $CO_2$, (B): 0.1% diethylamine in methanol].

Purification Method AN

Prep HPLC: [Reversed Phase (X-BRIDGE C-18, 250×19 mm, 5 μm), 15 mL/min, gradient 10%-30% (over 20 min), 30%-30% (over 5 min), 100% (over 2 min), 100%-10% (over 3 min), mobile phase (A): 5 mM ammonium bicarbonate in water+0.1% ammonia in water, (B): 100% acetonitrile].

Purification Method AO

Chiral HPLC: [Normal Phase (CHIRALPAK AD-H, 250×21 mm, 5 μm), 18 mL/min, Isocratic (A:B) 85:15 (over 30 min), mobile phase (A): 0.1% diethylamine in hexane, (B): 0.1% diethylamine in isopropanol].

Purification Method AP

Prep HPLC: [Reversed Phase (X-BRIDGE C-18, 250×19 mm, 5 μm), 16 mL/min, gradient 10%-32% (over 18 min), 100% (over 2 min), 100%-10% (over 2 min), mobile phase (A): 5 mM ammonium bicarbonate in water+0.1% ammonia in water, (B): 100% acetonitrile].

Purification Method AQ

Prep HPLC: [Reversed Phase (X-BRIDGE C-18, 250×19 mm, 5 μm), 13 mL/min, gradient 20%-25% (over 17 min), 25%-25% (over 3 min), 100% (over 2 min), 100%-20% (over 3 min), mobile phase (A): 5 mM ammonium bicarbonate in water+0.1% ammonia in water, (B): 100% acetonitrile].

Purification Method AR

Chiral HPLC: [Normal Phase (CHIRALCEL OX-H, 250×21 mm, 5 μm), 18 mL/min, Isocratic (A:B) 78:22 (over 37 min), mobile phase (A): 0.1% diethylamine in hexane, (B): 0.1% diethylamine in isopropanol:methanol (50:50)].

Purification Method AS

Prep HPLC: [Reversed Phase (X SELECT PHENYL HEXYL, 250×19 mm, 5 μm), 15 mL/min, gradient 25%-38% (over 16 min), 100% (over 2 min), 100%-25% (over 5 min), mobile phase (A): 5 mM ammonium bicarbonate in water+0.1% ammonia in water, (B): 100% acetonitrile].

Purification Method AT

Prep HPLC: [Reversed Phase (X SELECT PHENYL HEXYL, 250×19 mm, 5 μm), 15 mL/min, gradient 5%-35% (over 20 min), 100% (over 4 min), 100%-5% (over 4 min), mobile phase (A): 0.1% ammonia in water, (B): 100% acetonitrile].

Purification Method AU

Prep HPLC: [Reversed Phase (X-BRIDGE C-8, 250×19 mm, 5 μm), 15 mL/min, gradient 5%-28% (over 18 min), 28%-28% (over 2 min), 100% (over 2 min), 100%-5% (over 2 min), mobile phase (A): 5 mM ammonium bicarbonate in water+0.1% ammonia in water, (B): 100% acetonitrile].

Purification Method AV

Prep HPLC: [Reversed Phase (X-BRIDGE C-8, 250×19 mm, 5 μm), 15 mL/min, gradient 10%-20% (over 25 min), 20%-20% (over 8 min), 100% (over 2 min), 100%-10% (over 5 min), mobile phase (A): 5 mM ammonium bicarbonate in water+0.1% ammonia in water, (B): 100% acetonitrile].

Purification Method AW

Prep HPLC: [Reversed Phase (X-BRIDGE C-8, 250×19 mm, 5 μm), 15 mL/min, gradient 15%-20% (over 22 min), 20%-20% (over 5 min), 100% (over 2 min), 100%-15% (over 6 min), mobile phase (A): 5 mM ammonium bicarbonate in water+0.1% ammonia in water, (B): 100% acetonitrile].

Purification Method AX

Prep HPLC: [Reversed Phase (X-BRIDGE C-8, 250×19 mm, 5 μm), 10 mL/min, gradient 5%-55% (over 18 min), 55%-55% (over 6 min), 100% (over 2 min), 100%-5% (over 6 min), mobile phase (A): 5 mM ammonium bicarbonate in water+0.1% ammonia in water, (B): 100% acetonitrile].

Purification Method AY

Prep HPLC: [Reversed Phase (X-BRIDGE C-18, 250×19 mm, 5 μm), 15 mL/min, gradient 20%-45% (over 22 min), 100% (over 2 min), 100%-20% (over 5 min), mobile phase (A): 5 mM ammonium bicarbonate in water+0.1% ammonia in water, (B): 100% acetonitrile].

Purification Method AZ

Prep HPLC: [Reversed Phase (X-BRIDGE C-18, 250×19 mm, 5 μm), 16 mL/min, gradient 30%-39% (over 14 min), 100% (over 2 min), 100%-30% (over 4 min), mobile phase (A): 5 mM ammonium bicarbonate in water+0.1% ammonia in water, (B): 100% acetonitrile].

Purification Method BA

SFC: [(CHIRALPAK AD-H, 250×21 mm, 5 μm), 80 mL/min, Isochratic (A:B) 85:15 (over 7 min), mobile phase (A): 100% liquid $CO_2$, (B): 0.1% diethylamine in methanol].

Purification Method BB

Prep HPLC: [Reversed Phase (X-BRIDGE C-8, 250×19 mm, 5 μm), 13 mL/min, gradient 25%-35% (over 28 min), 35%-35% (over 2 min), 100% (over 2 min), 100%-25% (over 5 min), mobile phase (A): 5 mM ammonium bicarbonate in water+0.1% ammonia in water, (B): 100% acetonitrile].

Purification Method BC

Prep HPLC: [Reversed Phase (X-BRIDGE C-8, 250×19 mm, 5 μm), 13 mL/min, gradient 25%-40% (over 30 min), 40%-40% (over 2 min), 100% (over 2 min), 100%-25% (over 6 min), mobile phase (A): 5 mM ammonium bicarbonate in water+0.1% ammonia in water, (B): 100% acetonitrile].

Purification Method BD

Prep HPLC: [Reversed Phase (X-BRIDGE C-8, 250×19 mm, 5 μm), 14 mL/min, gradient 20%-50% (over 20 min), 50%-50% (over 5 min), 100% (over 2 min), 100%-20% (over 6 min), mobile phase (A): 5 mM ammonium bicarbonate in water+0.1% ammonia in water, (B): 100% acetonitrile].

Purification Method BE

Prep HPLC: [Reversed Phase (X-BRIDGE C-8, 250×19 mm, 5 μm), 12 mL/min, gradient 5%-50% (over 23 min), 50%-50% (over 5 min), 100% (over 2 min), 100%-5% (over 3 min), mobile phase (A): 5 mM ammonium bicarbonate in water+0.1% ammonia in water, (B): 100% acetonitrile].

Purification Method BF

Prep HPLC: [Reversed Phase (X-BRIDGE C-8, 250×19 mm, 5 μm), 13 mL/min, gradient 5%-55% (over 22 min), 55%-55% (over 6 min), 100% (over 2 min), 100%-5% (over 3 min), mobile phase (A): 5 mM ammonium bicarbonate in water+0.1% ammonia in water, (B): 100% acetonitrile].

Purification Method BG

Prep HPLC: [Reversed Phase (X-BRIDGE C-18, 250×19 mm, 5 μm), 14 mL/min, gradient 25%-52% (over 25 min), 52%-52% (over 9 min), 100% (over 2 min), 100%-25% (over 4 min), mobile phase (A): 5 mM ammonium bicarbonate in water+0.1% ammonia in water, (B): 100% acetonitrile].

Abbreviations

AcOH=acetic acid
aq.=aqueous
DCM=dichloromethane
DIPEA=diisopropylethylamine
DMF=dimethylformamide
DMSO=dimethylsulfoxide
ES(I)=electro spray ionization
$Et_2O$=diethyl ether
EtOAc=ethyl acetate
EtOH=ethanol
h=hour(s)
$H_2O$=water
HATU=1-[bis(dimethylamino)methylene]-1H-1,2,3-triazolo[4,5-b]pyridinium 3-oxid hexafluorophosphate
HCl=hydrogen chloride, hydrochloric acid
HPLC=high performance liquid chromatography
LC=liquid chromatography
MeCN=acetonitrile
MeOH=Methanol
min(s)=minute(s)
MS=mass spectrometry
nm=nanometre(s)
NMR=nuclear magnetic resonance
sat.=saturated
SFC=supercritical fluid chromatography
STAB=sodium triacetoxyborohydride
TFA=trifluoroacetic acid
THF=tetrahydrofuran
TLC=thin layer chromatography Prefixes n-, s-, i-, t- and tert- have their usual meanings: normal, secondary, iso, and tertiary.

Synthesis of Intermediates:

Route 1

Typical Procedure for the Preparation of Ketones, as Exemplified by the Preparation of Intermediate 3, 2-(3-methyl-1,2,4-oxadiazol-5-yl)-2-azaspiro[3.3]heptan-6-one

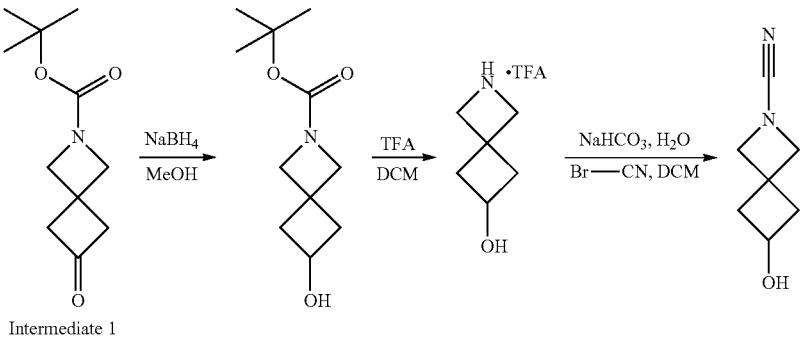

Intermediate 1

-continued

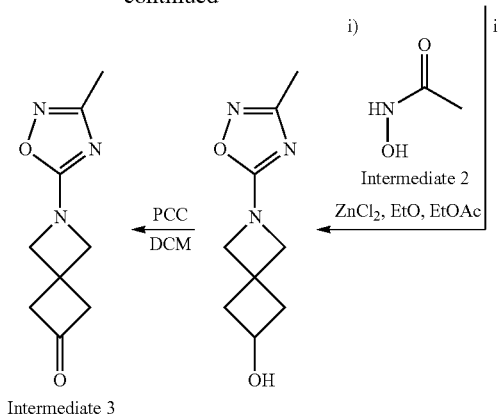

Intermediate 3 tert-Butyl 6-oxo-2-azaspiro[3.3]heptane-2-carboxylate (Intermediate 1) (500 mg, 2.37 mmol) was dissolved in MeOH (10 mL) and the resulting solution was cooled to 0° C. Sodium borohydride (270 mg, 7.10 mmol) was added portion wise and the resulting reaction mixture was stirred at 25° C. for 2 h. The solvents were removed in-vacuo and the residue was partitioned between H$_2$O (80 mL) and EtOAc (60 mL). The aqueous layer was further extracted with EtOAc (2×60 mL), and the organic layers were combined, dried (Na$_2$SO$_4$), and the solvent was removed in-vacuo. The residue was triturated with pentane to give tert-butyl 6-hydroxy-2-azaspiro[3.3]heptane-2-carboxylate (500 mg, 99%) as a solid.

LCMS (System 2, Method E): m/z 214 (M+H)$^+$ (ESI +ve), at 1.54 min, 202 nm.

tert-Butyl 6-hydroxy-2-azaspiro[3.3]heptane-2-carboxylate (500 mg, 2.34 mmol) was dissolved in DCM (10 mL) and the resulting solution was cooled to 0° C. Trifluoroacetic acid (1 mL) was added dropwise and the resulting reaction mixture was stirred at 25° C. for 6 h. The solvents were removed in-vacuo and the residue was triturated with pentane (3×1 mL) to give 2-azaspiro[3.3]heptan-6-ol trifluoroacetic acid salt (260 mg, 98%) as a gum.

LCMS (System 2, Method E): m/z 114 (M+H)$^+$ (ESI +ve), at 0.22 min, 202 nm.

2-Azaspiro[3.3]heptan-6-ol trifluoroacetic acid salt (250 mg, 2.21 mmol) was dissolved in DCM (10 mL), treated with sat. aq. NaHCO$_3$ (1 mL) and cooled to 0° C. for 10 min. Cyanogen bromide (255 mg, 2.43 mmol) was added portion wise and the resulting reaction mixture was stirred at 25° C. for 5 h. The solvents were removed in-vacuo and the residue was basified with sat. aq. NaHCO$_3$ solution. The precipitated solids were removed by filtration and washed with DCM 5 to 6 times. The combined filtrate and washings were then dried (Na$_2$SO$_4$), the solvent was removed in-vacuo and the crude product was purified by trituration with pentane to give 6-hydroxy-2-azaspiro[3.3]heptane-2-carbonitrile (230 mg, 75%) as a gum.

LCMS (System 2, Method E): m/z 139 (M+H)$^+$ (ESI +ve), at 0.76 min, 202 nm.

6-Hydroxy-2-azaspiro[3.3]heptane-2-carbonitrile (180 mg, 1.30 mmol) was dissolved in a mixture of EtOAc:Et$_2$O (5:1) (5 mL) and N-hydroxyacetamide (Intermediate 2) (125 mg, 1.69 mmol) was added. The resulting mixture was stirred at 25° C. for 5 min, then a solution of ZnCl$_2$ in diethyl ether (1 M, 1 mL, 1 mmol) was added drop wise. The reaction mixture was stirred at 25° C. for 20 min, during which time a white precipitate formed. The reaction mixture was diluted with Et$_2$O (3×10 mL) and the solvent was decanted off each time. The remaining solid was dissolved in EtOH (3 mL), treated with aq. HCl (4 M, 2 mL) and heated at reflux for 6 h. The solvents were removed in-vacuo and the residue was basified with aq. NaHCO$_3$ and then partitioned between H$_2$O (80 mL) and DCM (60 mL). The aqueous layer was further extracted with DCM (2×60 mL) and the combined organic layers were dried (Na$_2$SO$_4$) and the solvent was removed in-vacuo. The residue was purified by trituration with pentane to give 2-(3-methyl-1,2,4-oxadiazol-5-yl)-2-azaspiro[3.3]heptan-6-ol (60 mg, 24%) as a gum.

LCMS (System 2, Method E): m/z 196 (M+H)$^+$ (ESI +ve), at 1.34 min, 202 nm.

2-(3-Methyl-1,2,4-oxadiazol-5-yl)-2-azaspiro[3.3]heptan-6-ol (80 mg, 0.41 mmol) was dissolved in DCM (5 mL) and the solution was cooled to 0° C. Pyridinium chlorochromate (132 mg, 0.62 mmol) was added portion wise and the resulting reaction mixture was stirred at 25° C. for 3 h. The solvents were then removed in-vacuo and the residue was basified with NaHCO$_3$ solution and partitioned between H$_2$O (60 mL) and EtOAc (45 mL). The aqueous layer was further extracted with EtOAc (2×45 mL), and the combined organic layers were dried (Na$_2$SO$_4$), and the solvent was removed in-vacuo. The residue was triturated with pentane to give 2-(3-methyl-1,2,4-oxadiazol-5-yl)-2-azaspiro[3.3]heptan-6-one (Intermediate 3) (60 mg, 76%) as a gum.

The data for Intermediate 3 are in Table 2.

Route 2

Typical Procedure for the Preparation of Alcohols, as Exemplified by the Preparation of Intermediate 6, 6-azaspiro[3.4]octan-2-ol hydrochloride salt

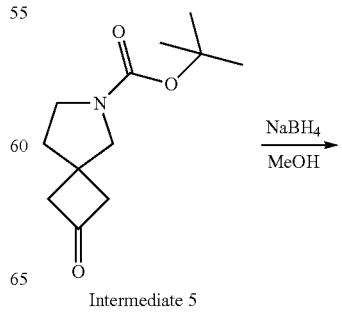

Intermediate 5

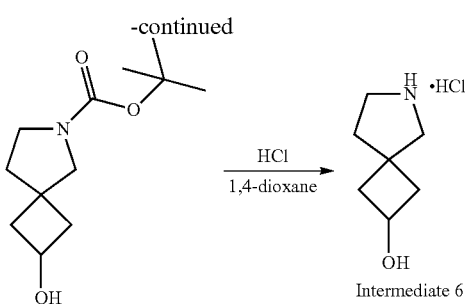

Intermediate 6 tert-Butyl 2-oxo-6-azaspiro[3.4]octane-6-carboxylate (Intermediate 5) (10 g, 44.3 mmol), was dissolved in MeOH (1000 mL) and the resulting solution was cooled to 0° C. Sodium borohydride (2.0 g, 53.2 mmol) was added portion wise and the resulting reaction mixture was stirred at 25° C. for 1 h. The solvents were removed in-vacuo and the residue was partitioned between H$_2$O (250 mL) and EtOAc (250 mL). The aqueous layer was further extracted with EtOAc (2×150 mL), and the organic layers were combined, dried (Na$_2$SO$_4$), and the solvent was removed in-vacuo to give tert-butyl 2-hydroxy-6-azaspiro[3.4]octane-6-carboxylate (9.2 g, 91%) as a gum.

LCMS (System 3, Method F): m/z 228 (M+H)$^+$ (ESI +ve), at 3.09 min, 202 nm.

tert-Butyl 2-hydroxy-6-azaspiro[3.4]octane-6-carboxylate (9 g, 39.6 mmol) was slowly dissolved in HCl solution in 1,4-dioxane (4 M, 90 mL) and the resulting reaction mixture was stirred at 25° C. for 16 h. The solvent was removed in-vacuo and the residue was purified by trituration with diethyl ether (3×50 mL) to give 6-azaspiro[3.4]octan-2-ol hydrochloride salt (Intermediate 6) (7 g, 90%) as a gum.

The data for Intermediate 6 are in Table 2.

Route 3

Typical Procedure for the Preparation of Alcohols, as Exemplified by the Preparation of Intermediate 27, 2-azabicyclo[2.2.2]octan-5-ol hydrochloride salt

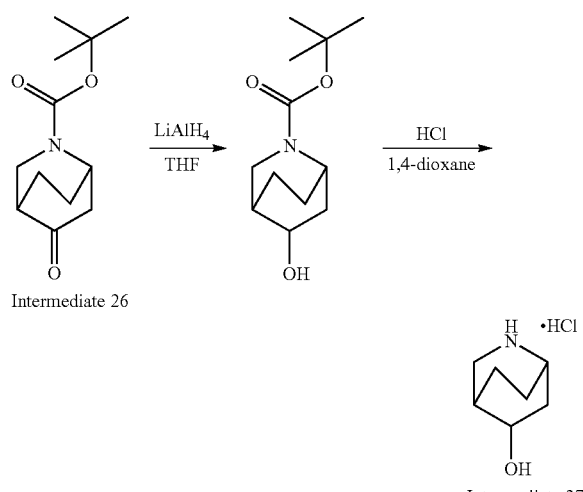

tert-Butyl 5-oxo-2-azabicyclo[2.2.2]octane-2-carboxylate (Intermediate 26) (500 mg, 2.2 mmol) was dissolved in THF (10 mL) and the solution was cooled to −20° C. under an atmosphere of nitrogen. Lithium aluminium hydride solution in THF (1 M, 3.3 mL, 3.3 mmol) was added at −20° C. and the resulting mixture was stirred at 0° C. for 2 h. The reaction mixture was partitioned between cold H$_2$O (25 mL) and EtOAc (15 mL) and the aqueous layer was further extracted with EtOAc (2×15 mL). The combined organic layers were dried (Na$_2$SO$_4$) and the solvent was removed in-vacuo to give tert-butyl 5-hydroxy-2-azabicyclo[2.2.2]octane-2-carboxylate (500 mg, 99%) as a gum.

LCMS (System 2, Method E): m/z 172 (M+H-56)$^+$ (ESI +ve), at 1.60 min, 202 nm.

tert-Butyl 5-hydroxy-2-azabicyclo[2.2.2]octane-2-carboxylate (500 mg, 2.2 mmol) was dissolved in HCl solution in 1,4-dioxane (4 M, 10 mL) at 0° C. and then stirred at room temperature for 2 h. The solvent was removed in-vacuo and the residue was triturated with n-pentane (2×10 mL) to give 2-azabicyclo[2.2.2]octan-5-ol hydrochloride salt (Intermediate 27) (280 mg, 100%) as a solid. The data for Intermediate 27 are in Table 2.

Route 4

Typical Procedure for the Preparation of Alcohols, as Exemplified by the Preparation of Intermediate 30, 9-azabicyclo[3.3.1]nonan-3-ol trifluoroacetic acid salt

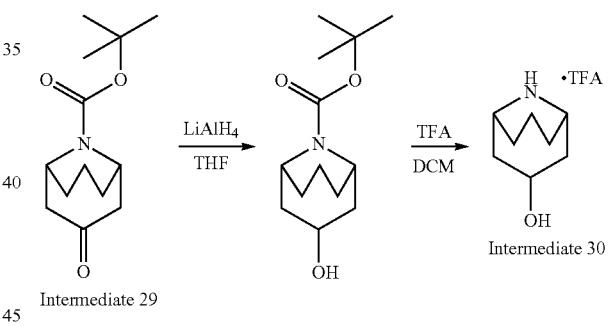

Intermediate 29

Intermediate 30

Lithium aluminium hydride solution in THF (1 M, 37.6 mL, 37.6 mmol) was added dropwise at 0° C. to a solution of tert-butyl 3-oxo-9-azabicyclo[3.3.1]nonane-9-carboxylate (Intermediate 29) (6 g, 25.1 mmol) in THF (60 mL), and the reaction mixture was stirred at 0° C. for 4 h. The reaction was then quenched by the addition of ice-cold water (20 mL), and the mixture was extracted with ethyl acetate (2×50 mL). The organic layers were combined, dried (Na$_2$SO$_4$), and the solvent was removed in-vacuo to give tert-butyl 3-hydroxy-9-azabicyclo[3.3.1]nonane-9-carboxylate (6 g, 99%) as a solid. The product was used crude in the next step without further purification or characterisation.

tert-Butyl 3-hydroxy-9-azabicyclo[3.3.1]nonane-9-carboxylate (6 g, 24.1 mmol) was dissolved in DCM (30 mL) and the resulting solution cooled to 0° C. TFA (15 mL) was added and the mixture was stirred at room temperature for 4 h. The solvent was removed in-vacuo and the residue was triturated with toluene (2×15 mL) to give 9-azabicyclo

[3.3.1]nonan-3-ol trifluoroacetic acid salt (Intermediate 30) (8.5 g, 100%) as a gum.

The data for Intermediate 30 are in Table 2.

Route 5

Typical Procedure for the Preparation of Amines, as Exemplified by the Preparation of Intermediate 47, [(2R,4R)-4-fluoro-1-(piperidin-4-yl)pyrrolidin-2-yl]methanol trifluoroacetic acid salt

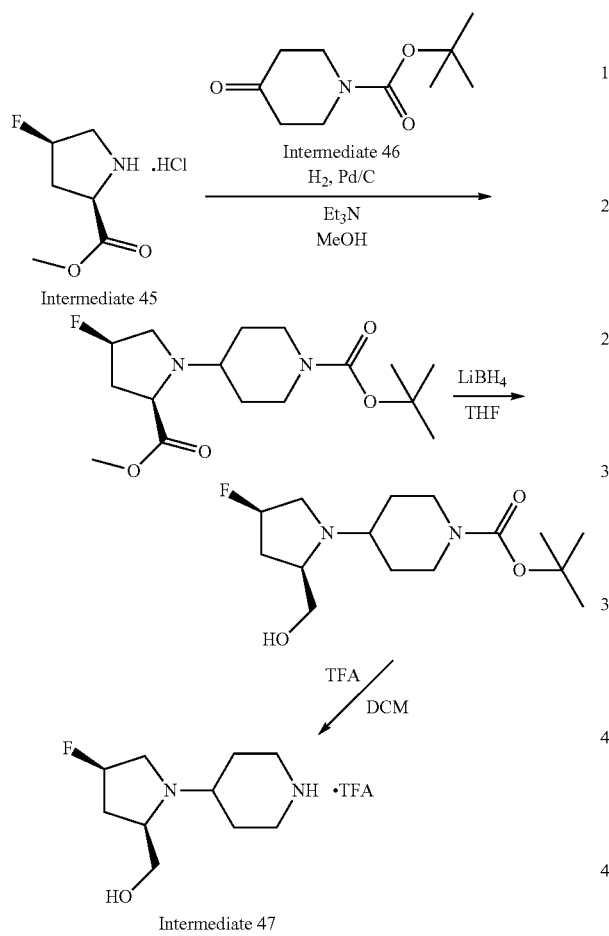

Intermediate 47

Methyl (2R,4R)-4-fluoropyrrolidine-2-carboxylate hydrochloride salt (Intermediate 45) (11.3 g, 61.7 mmol) was dissolved in methanol (280 mL) and tert-butyl 4-oxopiperidine-1-carboxylate (Intermediate 46) (12.2 g, 61.7 mmol), triethylamine (13 mL, 92.6 mmol) and 10% palladium on carbon catalyst (~50% wet with $H_2O$, 6 g) was added. The reaction mixture was stirred under hydrogen at one atmosphere pressure at 25° C. for 18 h, then filtered through Celite and the filtrate was concentrated in-vacuo. The resulting crude product was triturated with pentane to give tert-butyl 4-[(2R,4R)-4-fluoro-2-(methoxycarbonyl)pyrrolidin-1-yl]piperidine-1-carboxylate (18 g, 89%) as a solid.

LCMS (System 1, Method D): m/z 331 (M+H)$^+$ (ESI +ve), at 4.23 min, 210 nm.

tert-Butyl 4-[(2R,4R)-4-fluoro-2-(methoxycarbonyl)pyrrolidin-1-yl]piperidine-1-carboxylate (18 g, 54.5 mmol) was dissolved in THF (200 mL) and the resulting solution was cooled to 0° C. Lithium borohydride solution in THF (3 M, 54 mL, 164 mmol) was then added dropwise, and the mixture was stirred at 25° C. for 17 h. The solvents were removed in-vacuo and the residue was basified with saturated $NaHCO_3$ solution and partitioned between $H_2O$ (600 mL) and DCM (400 mL). The aqueous layer was further extracted with EtOAc (2×400 mL), then all the organic layers were combined, dried ($Na_2SO_4$) and the solvent was removed in-vacuo. The residue was purified by trituration with pentane (3×10 mL) to give tert-butyl 4-[(2R,4R)-4-fluoro-2-(hydroxymethyl)pyrrolidin-1-yl]piperidine-1-carboxylate (14.5 g, 88%) as a gum.

LCMS (System 1, Method D): m/z 303 (M+H)$^+$ (ESI +ve), at 3.57 min, 210 nm.

tert-Butyl 4-[(2R,4R)-4-fluoro-2-(hydroxymethyl)pyrrolidin-1-yl]piperidine-1-carboxylate (14.5 g, 0.42 mmol) was dissolved in DCM (100 mL) and the resulting solution was cooled to 0° C. Trifluoroacetic acid (30 mL) was added dropwise and the reaction mixture was stirred at 25° C. for 8 h. The solvents were removed in-vacuo and the residue was purified by trituration with pentane (3×10 mL) to give [(2R,4R)-4-fluoro-1-(piperidin-4-yl)pyrrolidin-2-yl]methanol trifluoroacetic acid salt (Intermediate 47) (9.60 g, 100%) as a colourless gum.

The data for Intermediate 47 are in Table 2.

Route 6

Typical Procedure for the Preparation of Amines, as Exemplified by the Preparation of Intermediate 51, 4-[2-(1-methyl-1H-pyrazol-4-yl)pyrrolidin-1-yl]piperidine trifluoroacetic acid salt

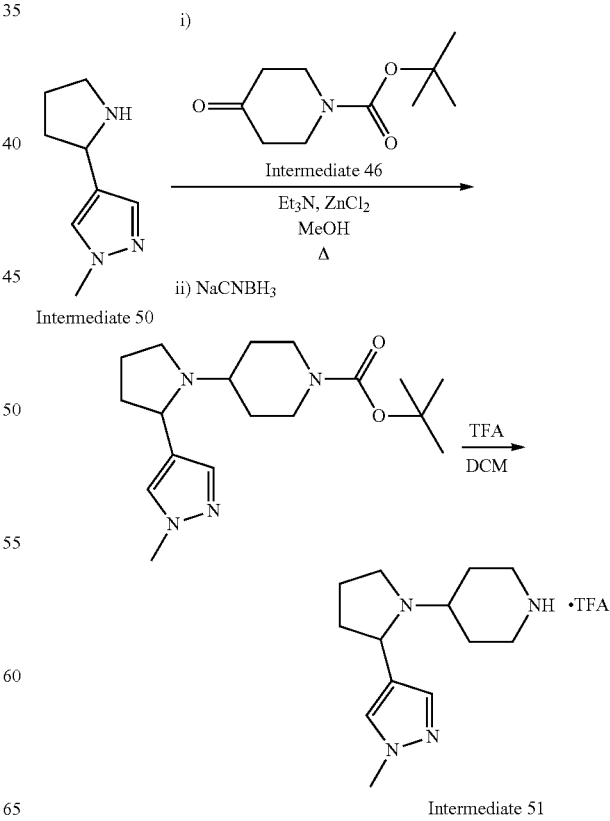

Intermediate 51

1-Methyl-4-(pyrrolidin-2-yl)-1H-pyrazole (Intermediate 50) (0.25 g, 1.66 mmol), tert-butyl 4-oxopiperidine-1-carboxylate (Intermediate 46) (0.32 g, 1.66 mmoL), ZnCl$_2$ solution in diethyl ether (1 M, 0.083 mL, 0.083 mmol) and triethylamine (0.72 mL, 4.97 mmol) were dissolved in MeOH (10 mL) and the resulting mixture was stirred at 70° C. for 4 h. The mixture was then cooled to 0° C. and NaBH$_3$CN (0.21 g, 3.31 mmoL) was added portionwise. The reaction mixture was stirred at room temperature for 16 h and then the solvents were removed in-vacuo. The residue was partitioned between H$_2$O (50 mL) and EtOAc (100 mL), and the aqueous layer was further extracted with EtOAc (2×100 mL). The combined organic layers were dried (Na$_2$SO$_4$) and the solvent was removed in-vacuo to give the crude product which was purified by column chromatography using alumina and MeOH/DCM as solvents to give tert-butyl 4-(2-(1-methyl-1H-pyrazol-4-yl)pyrrolidin-1-yl)piperidine-1-carboxylate (0.33 g, 59%) as a gum.

LCMS (System 3, Method F): m/z 335 (M+H)$^+$ (ESI +ve), at 3.23 min, 215 nm.

To a stirred solution of tert-butyl 4-(2-(1-methyl-1H-pyrazol-4-yl)pyrrolidin-1-yl)piperidine-1-carboxylate (0.30 g, 0.90 mmol) in DCM (3 mL) at 0° C. was added TFA (3 mL) dropwise and the resulting mixture was stirred at room temperature for 3 h. The solvent was evaporated in-vacuo and the residue co-evaporated from toluene (3×5 mL) to give 4-[2-(1-methyl-1H-pyrazol-4-yl)pyrrolidin-1-yl]piperidine trifluoroacetic acid salt (Intermediate 51) (0.20 g, 95%) as a gum.

The data for Intermediate 51 are in Table 2.

Route 7

Typical Procedure for the Preparation of Ketones, as Exemplified by the Preparation of Intermediate 60, 8-(3-(trifluoromethyl)-1,2,4-oxadiazol-5-yl)-8-azabicyclo[3.2.1]octan-3-one Trifluoroacetic acid (25 mL) was added dropwise at 0° C. to a solution of tert-butyl 3-oxo-8-azabicyclo[3.2.1]octane-8-carboxylate (Intermediate 17) (10 g, 44.4 mmol) in DCM (100 mL). The resulting mixture was stirred at room temperature for 2 h, then the solvent was evaporated under reduced pressure and the residue was triturated with toluene (3×15 mL) to give the crude 8-azabicyclo[3.2.1]octan-3-one trifluoroacetic acid salt (16 g, 100%), which was carried forward to the next reaction without further purification.

LCMS (System 4, Method B): m/z 126 (M+H)$^+$ (ESI +ve), at 2.20 min, 214 nm.

A solution of 8-azabicyclo[3.2.1]octan-3-one trifluoroacetic acid salt (16 g, 0.067 mol) in DCM (150 mL) was added dropwise to a solution of sodium bicarbonate (26 g, 0.32 mol) in water (100 mL) with vigorous stirring. A solution of cyanogen bromide (16.3 g, 0.153 mol) in DCM (25 mL) was then added at 0° C., the ice bath was removed and the resulting reaction mixture was stirred at room temperature for 16 h. Solid sodium carbonate was added until the pH was adjusted to 7, then the mixture was extracted with DCM (3×25 mL). The organic phases were dried over anhydrous Na$_2$SO$_4$ and concentrated under reduced pressure. The residue was purified by column chromatography (Normal phase, Silica gel 60-120 mesh, 0 to 3% MeOH in DCM) to afford 3-oxo-8-azabicyclo[3.2.1]octane-8-carbonitrile (6.5 g, 65%).

LCMS (System 4, Method B): m/z 151 (M+H)$^+$ (ESI +ve), at 4.13 min, 202 nm.

3-Oxo-8-azabicyclo[3.2.1]octane-8-carbonitrile (1 g, 6.65 mmol) and 2,2,2-trifluoro-N-hydroxyacetimidamide (Intermediate 59) (1 g, 7.99 mmol) were dissolved in ethanol (50 mL), ZnCl$_2$ solution in diethyl ether (1 M, 7.99 mL, 7.99 mmol) was added and the resulting mixture was stirred at room temperature for 16 h. Aqueous HCl (4 M, 6 mL) was then added and the mixture was heated at reflux at 90° C. overnight. Saturated sodium bicarbonate solution (50 mL) was added and the mixture was extracted with ethyl acetate (3×10 mL). The combined organic layers were dried over anhydrous Na$_2$SO$_4$, concentrated under reduced pressure and the residue was purified by column chromatography (Normal phase, Silica gel 60-120 mesh, 0 to 7% EtOAC in hexanes) to give 8-(3-(trifluoromethyl)-1,2,4-oxadiazol-5-yl)-8-azabicyclo[3.2.1]octan-3-one (Intermediate 60) (517 mg, 30%).

The data for Intermediate 60 are in Table 2.

Route 8

Typical Procedure for the Preparation of Amines, as Exemplified by the Preparation of Intermediate 62, (1R,5S,6r)-N-(-methylcyclobutyl)-3-azabicyclo[3.1.0]hexane-6-carboxamide hydrochloride salt

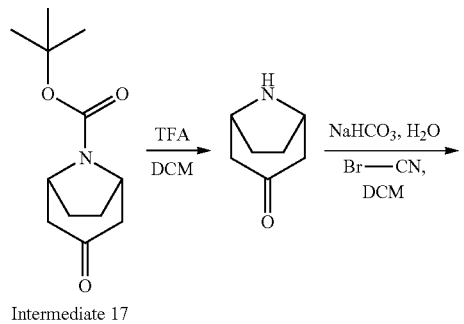

Intermediate 17

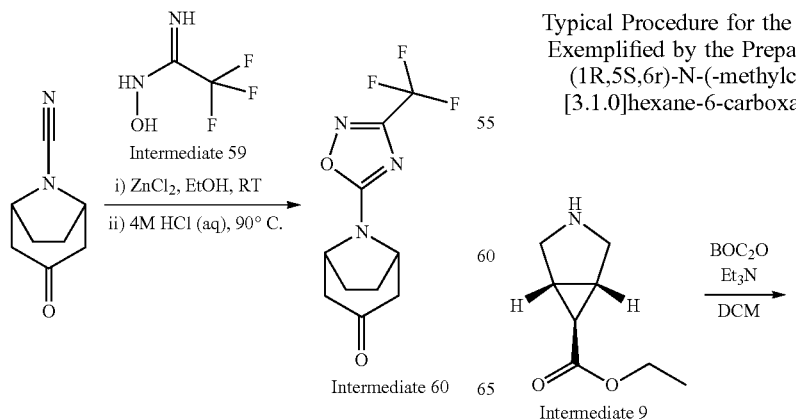

Intermediate 60

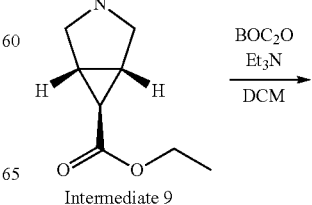

Intermediate 9

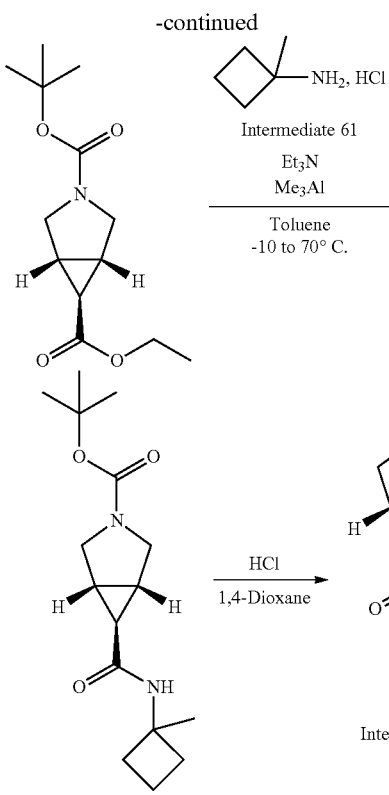

LCMS (System 3, Method F): m/z 293 (M–H)– (ESI –ve), at 3.80 min, 202 nm.

tert-Butyl(1R,5S,6r)-6-((1-methylcyclobutyl)carbamoyl)-3-azabicyclo[3.1.0]hexane-3-carboxylate (550 mg, 1.87 mmol) was dissolved in 1,4-dioxane (6 mL) and the solution was cooled to 0° C. HCl solution in 1,4-dioxane (4 M, 10 mL) was added and the reaction mixture was stirred at 25° C. for 5 h. The solvents were removed in-vacuo and the residue was purified by trituration with pentane (3×3 mL) to give (1R,5S,6r)-N-(1-methylcyclobutyl)-3-azabicyclo[3.1.0]hexane-6-carboxamide hydrochloride salt (Intermediate 62) (408 mg, 95%) as a solid.

The data for Intermediate 62 are in Table 2.

Route 9

Typical Procedure for the Preparation of Amines, as Exemplified by the Preparation of Intermediate 68, N-((1-methylcyclobutyl)methyl)piperidine-4-carboxamide trifluoroacetic acid salt

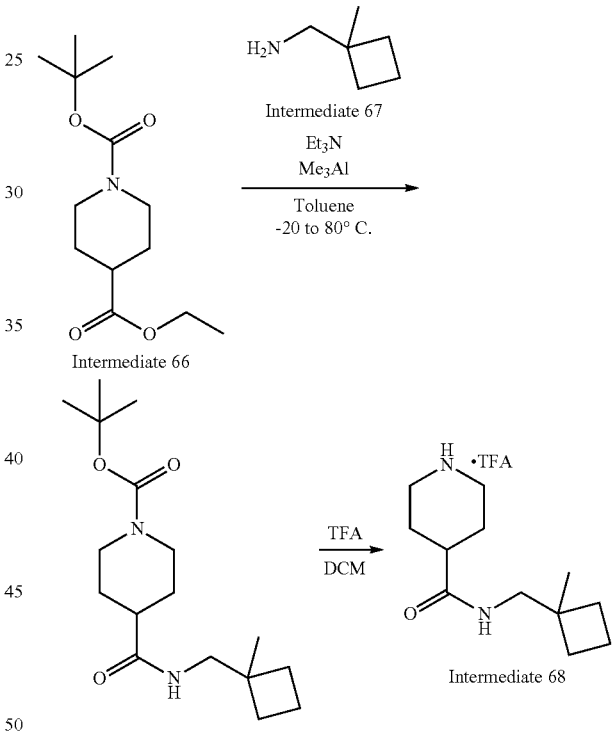

Ethyl(1R,5S,6r)-3-azabicyclo[3.1.0]hexane-6-carboxylate (Intermediate 9) (2.0 g, 8.16 mmol) was dissolved in DCM (25 mL) and triethylamine (3.45 mL, 24.5 mmol) was added. The mixture was cooled to 0° C., stirred for 20 mins and di-tert-butyl dicarbonate (2.65 g, 12.2 mmol) was added. The resulting reaction mixture was then stirred at 25° C. for 18 h. The solvents were removed in-vacuo and the residue was partitioned between H$_2$O (80 mL) and ethyl acetate (60 mL). The aqueous layer was further extracted with ethyl acetate (2×60 mL), the combined organic layers were dried (Na$_2$SO$_4$) and the solvent was removed in-vacuo. The residue was purified by column chromatography (Normal-Phase activated Al$_2$O$_3$, 0% to 40% ethyl acetate in hexanes) to give 3-(tert-butyl) 6-ethyl(1R,5S,6r)-3-azabicyclo[3.1.0]hexane-3,6-dicarboxylate (1.70 g, 82%) as a liquid.

LCMS (System 3, Method F): m/z 241 (M-15+H)$^+$ (ESI +ve), at 4.06 min, 202 nm.

1-Methylcyclobutan-1-amine hydrochloride (Intermediate 61) (948 mg, 7.84 mmol) was suspended in toluene (10 mL) and triethylamine (1.70 mL, 11.8 mmol) was added. The mixture was cooled to –10° C., trimethylaluminum solution in toluene (2 M, 5.9 mL, 11.8 mmol) was added dropwise and stirring was continued for 20 min. 3-(tert-Butyl) 6-ethyl(1R,5S,6r)-3-azabicyclo[3.1.0]hexane-3,6-dicarboxylate (1.0 g, 3.92 mmol) was added at –10° C., then the reaction mixture was stirred at 70° C. for 40 h. The solvents were removed in-vacuo and the residue was partitioned between H$_2$O (80 mL) and ethyl acetate (60 mL). The aqueous layer was further extracted with ethyl acetate (2×80 mL) and the combined organic layers were dried (Na$_2$SO$_4$) and the solvent was removed in-vacuo. The residue was purified by column chromatography (Normal-Phase activated Al$_2$O$_3$, 0% to 60% ethyl acetate in hexanes) to give tert-butyl (1R,5S,6r)-6-((1-methylcyclobutyl)carbamoyl)-3-azabicyclo[3.1.0]hexane-3-carboxylate (560 mg, 49%) as a solid.

1-(tert-Butyl) 4-ethyl piperidine-1,4-dicarboxylate (Intermediate 64) (700 mg, 0.0027 mole) and (1-methylcyclobutyl)methanamine (Intermediate 65) (434 mg, 0.0032 mole) were dissolved in toluene (3.0 mL) and triethylamine (1.13 mL, 0.008 mole) was added, followed by trimethylaluminum solution in toluene (2 M, 5.44 mL, 0.0108 mole) added dropwise at –20° C. The mixture was stirred for 30 min at –20° C. and then heated at 80° C. for 48 hrs. The reaction mixture was concentrated under reduced pressure and the residue was partitioned between cold H$_2$O (200 mL) and DCM (100 mL). The aqueous layer was further extracted with DCM (2×100 mL) and the combined organic layers were dried (Na$_2$SO$_4$) and the solvent was removed in-vacuo. The crude product was purified by column chromatography (Normal phase, 100-120 mesh silica gel, 0 to 39% ethyl acetate in hexanes) to give tert-butyl 4-(((1- methylcyclobutyl)methyl)carbamoyl)piperidine-1-carboxylate (320 mg, 38%) as a solid.

LCMS (System 2, Method H): m/z 311 (M+H)$^+$ (ESI +ve), at 1.71 min, 202 nm.

A solution of tert-butyl 4-(((1-methylcyclobutyl)methyl) carbamoyl)piperidine-1-carboxylate (320 mg, 0.00103 mol) in DCM (2 mL) was cooled to 0° C. and TFA (1 mL) was added dropwise, then the resulting reaction mixture was stirred at RT for 2 h. The solvent was removed in-vacuo and the residue was purified by trituration with toluene (3×5 mL) to give the crude N-((1-methylcyclobutyl)methyl)piperidine-4-carboxamide trifluoroacetic acid salt (Intermediate 66) (410 mg, 100%), which was used without further purification.

The data for Intermediate 66 are in Table 2.

General Synthetic Procedures:

Route A

Typical Procedure for the Preparation of Amines as Exemplified by the Preparation of Example 1-1,2-(3-methyl-1,2,4-oxadiazol-5-yl)-6-[4-(1H-pyrazol-1-yl)piperidin-1-yl]-2-azaspiro[3.3]heptane

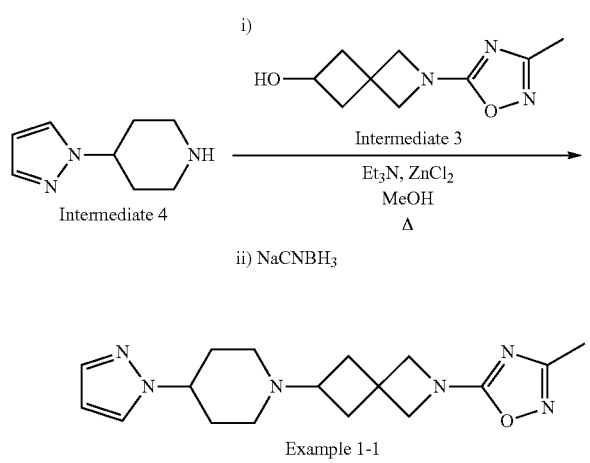

4-(1H-Pyrazol-1-yl)piperidine (Intermediate 4) (47 mg, 0.31 mmol), 2-(3-methyl-1,2,4-oxadiazol-5-yl)-2-azaspiro[3.3]heptan-6-one (Intermediate 3) (60 mg, 0.31 mmol), triethylamine (0.1 mL, 0.93 mmol) and ZnCl$_2$ (4 mg, 0.03 mmol) were dissolved in MeOH (10 mL) and the resulting mixture was stirred at 65° C. for 8 h. The mixture was then cooled to 0° C. and NaBH$_3$CN (58 mg, 0.93 mmol) was added portion wise and the resulting reaction mixture was stirred at 25° C. for 16 h. The solvents were removed in-vacuo, the residue was partitioned between H$_2$O (50 mL) and EtOAc (40 mL), and the aqueous layer was further extracted with EtOAc (2×40 mL). The combined organic layers were dried (Na$_2$SO$_4$), the solvent was removed in-vacuo, and the residue was purified using Purification Method A to give 2-(3-methyl-1,2,4-oxadiazol-5-yl)-6-[4-(1H-pyrazol-1-yl)piperidin-1-yl]-2-azaspiro[3.3]heptane (Example 1-1) (17 mg, 17%) as a solid.

The data for Example 1-1 are in Table 3.

Route B

Typical Procedure for the Preparation of Amines as Exemplified by the Preparation of Example 6-5, N-(1-methylcyclobutyl)-1-[8-(3-methyl-1,2,4-oxadiazol-5-yl)-8-azabicyclo[3.2.1]oct-3-yl]piperidine-4-carboxamide

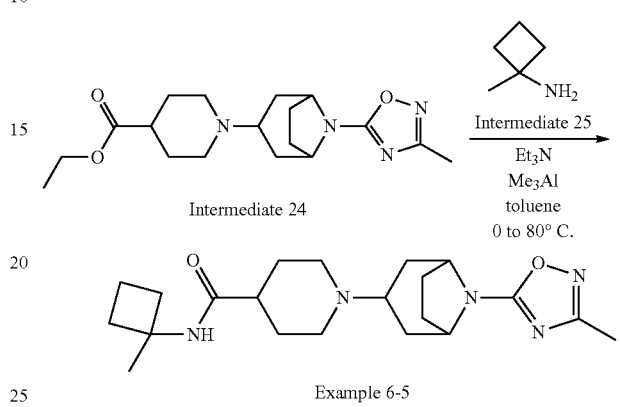

Triethylamine (0.12 ml, 0.86 mmol) was added dropwise to a solution of 1-methylcyclobutan-1-amine (Intermediate 25) (27 mg, 0.3 mmol) in toluene (10 mL) and the mixture was stirred at room temperature for 15 min. Ethyl 1-[8-(3-methyl-1,2,4-oxadiazol-5-yl)-8-azabicyclo[3.2.1]oct-3-yl] piperidine-4-carboxylate (Intermediate 24) (100 mg, 0.29 mmol) was added and the reaction mixture was stirred at room temperature for 15 min and then cooled to 0° C. Trimethylaluminium solution in toluene (2 M, 0.43 mL, 0.86 mmol) was added at 0° C., and then the reaction mixture was stirred at 80° C. for 16 h. The mixture was partitioned between H$_2$O (10 mL) and ethyl acetate (20 mL), and the aqueous layer was further extracted with ethyl acetate (2×20 mL). The combined organic layers were dried (Na$_2$SO$_4$) and the solvent was removed in-vacuo to give the crude product, which was purified by Purification Method L to give N-(1-methylcyclobutyl)-1-[8-(3-methyl-1,2,4-oxadiazol-5-yl)-8-azabicyclo[3.2.1]oct-3-yl]piperidine-4-carboxamide, Example 6-5 Isomer 1 (40 mg, 24%) as a gum and N-(1-methylcyclobutyl)-1-[8-(3-methyl-1,2,4-oxadiazol-5-yl)-8-azabicyclo[3.2.1]oct-3-yl]piperidine-4-carboxamide, Example 6-5 Isomer 2 (5 mg, 3%) as a solid.

The data for Example 6-5 Isomer 2 are in Table 3.

Route C

Typical Procedure for the Preparation of Amines as Exemplified by the Preparation of Example 10-12, (2S)-N-methyl-2-{1-[1-(3-methyl-1,2,4-oxadiazol-5-yl)azepan-4-yl]piperidin-4-yl}pyrrolidine-1-carboxamide

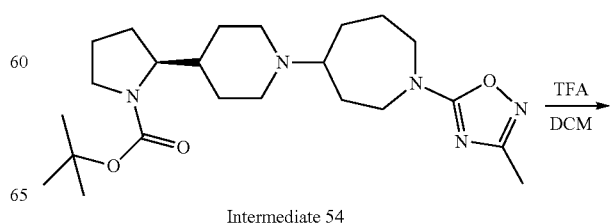

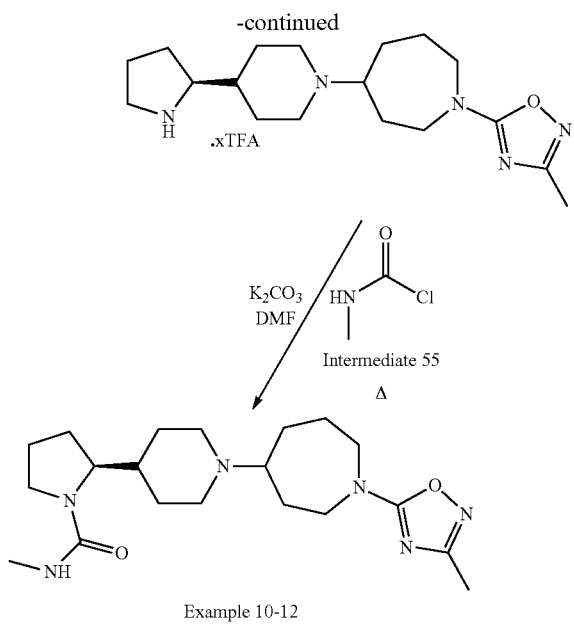

Example 10-12

To a stirred solution of tert-butyl (2S)-2-{1-[1-(3-methyl-1,2,4-oxadiazol-5-yl)azepan-4-yl]piperidin-4-yl}pyrrolidine-1-carboxylate (Intermediate 54) (260 mg, 0.60 mmol) in DCM (3 mL) was added TFA (3 mL) dropwise at 0° C. The reaction mixture was stirred at room temperature for 3 h, then the solvent was evaporated in-vacuo and the residue co-evaporated from toluene (3×5 mL) to give 1-(3-methyl-1,2,4-oxadiazol-5-yl)-4-{4-[(2S)-pyrrolidin-2-yl]piperidin-1-yl}azepane trifluoroacetic acid salt (190 mg, 95%) as a gum.

LCMS (System 3, Method F): m/z 334 (M+H)$^+$ (ESI +ve), at 1.95 min, 225 nm.

To a stirred solution of 1-(3-methyl-1,2,4-oxadiazol-5-yl)-4-{4-[(2S)-pyrrolidin-2-yl]piperidin-1-yl}azepane trifluoroacetic acid salt (300 mg, 1.29 mmol) in DMF (3 mL) was added K$_2$CO$_3$ (533 mg, 3.86 mmol) and the resulting mixture was stirred at room temperature for 1 h. Methylcarbamyl chloride (Intermediate 55) (240 mg, 2.58 mmol) was added and the reaction mixture was stirred at 80° C. for 16 h. The reaction mixture was then diluted with ice-cold water (10 mL) and extracted with EtOAc (20 mL). The aqueous layer was further extracted with EtOAc (2×10 mL), then all the organic layers were combined, dried (Na$_2$SO$_4$) and evaporated under reduced pressure to give the crude product, which was purified by Purification Method AQ followed by Purification Method AR to give (2S)—N-methyl-2-{1-[1-(3-methyl-1,2,4-oxadiazol-5-yl)azepan-4-yl]piperidin-4-yl}pyrrolidine-1-carboxamide, Example 10-12 Isomer 1 (11 mg, 2%) as a gum and (2S)—N-methyl-2-{1-[1-(3-methyl-1,2,4-oxadiazol-5-yl)azepan-4-yl]piperidin-4-yl}pyrrolidine-1-carboxamide, Example 10-12 Isomer 2 (10 mg, 2%) as a gum.

The data for Example 10-12 Isomer 1 and Example 10-12 Isomer 2 are in Table 3.

TABLE 2

Table 2 - Starting Materials and Intermediates

| Intermediate Number | Name | Synthetic Route | Intermediates Used | Data |
|---|---|---|---|---|
| 1 | tert-Butyl 6-oxo-2-azaspiro[3.3]heptane-2-carboxylate | — | — | Commercially available, CAS: 1181816-12-5 |
| 2 | N-Hydroxyacetamide | — | — | Commercially available, CAS: 546-88-3 |
| 3 | 2-(3-Methyl-1,2,4-oxadiazol-5-yl)-2-azaspiro[3.3]heptan-6-one | 1 | 1 and 2 | LCMS (System 2, Method E): m/z 194 (M + H)$^+$ (ES$^+$), at 1.36 min, 226 nm |
| 4 | 4-(1H-Pyrazol-1-yl)piperidine | — | — | Commercially available, CAS: 762240-09-5 |
| 5 | tert-Butyl 2-oxo-6-azaspiro[3.4]octane-6-carboxylate | — | — | Commercially available, CAS: 203661-71-6 |
| 6 | 6-Azaspiro[3.4]octan-2-ol hydrochloride salt | 2 | 5 | $^1$H NMR (400 MHz, DMSO-d$_6$) δ 9.42 (br. s, 1H), 9.31 (br. s, 1H), 4.13-4.00 (m, 1H), 3.14-2.97 (m, 4H), 2.36-2.25 (m, 1H), 2.23-2.12 (m, 1H), 1.93-1.77 (m, 4H). One exchangeable proton not observed. |
| 7 | 6-(3-Methyl-1,2,4-oxadiazol-5-yl)-6-azaspiro[3.4]octan-2-one | 1 (from Step 3) | 6 and 2 | LCMS (System 3, Method F): m/z 208 (M + H)$^+$ (ES$^+$), at 2.25 min, 202 nm |
| 8 | 4-Phenylpiperidine-4-carbonitrile | — | — | Commercially available, CAS: 40481-13-8 |
| 9 | Ethyl (1R,5S,6r)-3-azabicyclo[3.1.0]hexane-6-carboxylate | — | — | Commercially available, CAS: 174456-77-0 |
| 10 | tert-Butyl 6-oxo-2-azaspiro[3.4]octane-2-carboxylate | — | — | Commercially available, CAS: 1363382-39-1 |
| 11 | 2-Azaspiro[3.4]octan-6-ol hydrochloride salt | 2 | 10 | $^1$H NMR (400 MHz, DMSO-d$_6$) δ 9.07 (br. s, 1H), 8.12 (br. s, 1H), 4.12-4.03 (m, 1H), 3.93-3.65 (m, 4H), 3.00-2.87 (m, 1H), 2.10-1.94 (m, 1H), 1.84-1.66 (m, 3H), 1.64-1.40 (m, 2H). |

TABLE 2-continued

Table 2 - Starting Materials and Intermediates

| Intermediate Number | Name | Synthetic Route | Intermediates Used | Data |
|---|---|---|---|---|
| 12 | 2-(3-Methyl-1,2,4-oxadiazol-5-yl)-2-azaspiro[3.4]octan-6-one | 1 (from Step 3) | 11 and 2 | LCMS (System 2, Method E): m/z 208 (M + H)$^+$ (ES$^+$), at 1.39 min, 230 nm |
| 13 | Piperidin-4-ol | — | — | Commercially available, CAS: 5382-16-1 |
| 14 | 1-(3-Methyl-1,2,4-oxadiazol-5-yl)piperidin-4-one | 1 (from Step 3) | 13 and 2 | LCMS (System 2, Method E): m/z 182 (M + H)$^+$ (ES$^+$), at 1.31 min, 228 nm |
| 15 | tert-Butyl 6-oxo-3-azabicyclo[3.1.1]heptane-3-carboxylate | — | — | Commercially available, CAS: 1251013-26-9 |
| 16 | 3-(3-Methyl-1,2,4-oxadiazol-5-yl)-3-azabicyclo[3.1.1]heptan-6-one | 1 | 15 and 2 | LCMS (System 4, Method B): m/z 194 (M + H)$^+$ (ES$^+$), at 3.91 min, 202 nm |
| 17 | tert-Butyl 3-oxo-8-azabicyclo[3.2.1]octane-8-carboxylate | — | — | Commercially available, CAS: 185099-67-6 |
| 18 | 8-(3-Methyl-1,2,4-oxadiazol-5-yl)-8-azabicyclo[3.2.1]octan-3-one | 1 | 17 and 2 | LCMS (System 3, Method F): m/z 208 (M + H)$^+$ (ES$^+$), at 2.33 min, 202 nm |
| 19 | 2,8-Diazaspiro[4.5]decan-3-one | — | — | Commercially available, CAS: 561314-57-6 |
| 20 | N-Hydroxypropanamide | — | — | Commercially available, CAS: 2580-63-4 |
| 21 | 8-(3-Ethyl-1,2,4-oxadiazol-5-yl)-8-azabicyclo[3.2.1]octan-3-one | 1 | 17 and 20 | LCMS (System 3, Method F): m/z 222 (M + H)$^+$ (ES$^+$), at 2.67 min, 202 nm |
| 22 | 1-Oxa-3,8-diazaspiro[4.5]decan-2-one | — | — | Commercially available, CAS: 5052-95-9 |
| 23 | Ethyl piperidine-4-carboxylate | — | — | Commercially available, CAS: 1126-09-6 |
| 24 | Ethyl 1-[8-(3-methyl-1,2,4-oxadiazol-5-yl)-8-azabicyclo[3.2.1]oct-3-yl]piperidine-4-carboxylate | A | 23 and 18 | LCMS (System 3, Method F): m/z 349 (M + H)$^+$ (ES$^+$), at 3.21 min, 202 nm |
| 25 | 1-Methylcyclobutan-1-amine | — | — | Commercially available, CAS: 40571-47-9 |
| 26 | tert-Butyl 5-oxo-2-azabicyclo[2.2.2]octane-2-carboxylate | — | — | Commercially available, CAS: 617714-22-4 |
| 27 | 2-Azabicyclo[2.2.2]octan-5-ol hydrochloride salt | 3 | 26 | LCMS (System 4, Method C): m/z 128 (M + H)$^+$ (ES$^+$), at 2.56 and 3.66 min, no UV absorption at 202 nm |
| 28 | 2-(3-Methyl-1,2,4-oxadiazol-5-yl)-2-azabicyclo[2.2.2]octan-5-one | 1 (from Step 3) | 27 and 2 | LCMS (System 3, Method F): m/z 208 (M + H)$^+$ (ES$^+$), at 2.27 min, 202 nm |
| 29 | tert-Butyl 3-oxo-9-azabicyclo[3.3.1]nonane-9-carboxylate | — | — | Commercially available, CAS: 512822-27-4 |
| 30 | 9-Azabicyclo[3.3.1]nonan-3-ol trifluoroacetic acid salt | 4 | 29 | LCMS (System 4, Method B): m/z 142 (M + H)$^+$ (ES$^+$), at 1.82 min, 202 nm |
| 31 | 9-(3-Methyl-1,2,4-oxadiazol-5-yl)-9-azabicyclo[3.3.1]nonan-3-one | 1 (from Step 3) | 30 and 2 | LCMS (System 3, Method F): m/z 222 (M + H)$^+$ (ES$^+$), at 2.46 min, 202 nm |
| 32 | Ethyl 1-[9-(3-methyl-1,2,4-oxadiazol-5-yl)-9-azabicyclo[3.3.1]non-3-yl]piperidine-4-carboxylate | A | 23 and 31 | LCMS (System 3, Method F): m/z 363 (M + H)$^+$ (ES$^+$), at 3.08 min, 202 nm |
| 33 | tert-Butyl 7-oxo-3-oxa-9-azabicyclo[3.3.1]nonane-9-carboxylate | — | — | Commercially available, CAS: 280761-97-9 |
| 34 | 3-Oxa-9-azabicyclo[3.3.1]nonan-7-ol hydrochloride salt | 3 | 33 | $^1$H NMR (400 MHz, DMSO-d$_6$) δ 9.40 (br. s, 1H), 9.08 (br. s, 1H), 4.98-4.86 (m, 1H), 4.02-3.79 (m, 5H), 3.61-3.52 (m, 2H), 2.37-2.25 (m, 2H), 1.85-1.75 (m, 2H). |
| 35 | 9-(3-Methyl-1,2,4-oxadiazol-5-yl)-3-oxa-9-azabicyclo[3.3.1]nonan-7-one | 1 (from Step 3) | 34 and 2 | LCMS (System 3, Method F): m/z 224 (M + H)$^+$ (ES$^+$), at 1.84 min, 202 nm |

TABLE 2-continued

Table 2 - Starting Materials and Intermediates

| Intermediate Number | Name | Synthetic Route | Intermediates Used | Data |
|---|---|---|---|---|
| 36 | Methyl (1R,5S,6r)-3-azabicyclo[3.1.0]hexane-6-carboxylate | — | — | Commercially available, CAS: 1024038-72-9 |
| 37 | Methyl (1R,5S,6r)-3-[9-(3-methyl-1,2,4-oxadiazol-5-yl)-3-oxa-9-azabicyclo[3.3.1]nonan-7-yl]-3-azabicyclo[3.1.0]hexane-6-carboxylate | A | 36 and 35 | LCMS (System 3, Method F): m/z 349 (M + H)$^+$ (ES$^+$), at 2.90 min, 202 nm |
| 38 | N-Ethylethanamine | — | — | Commercially available, CAS: 109-89-7 |
| 39 | tert-Butyl 4-oxoazepane-1-carboxylate | — | — | Commercially available, CAS: 188975-88-4 |
| 40 | Azepan-4-ol hydrochloride salt | 2 | 39 | $^1$H NMR (400 MHz, DMSO-d$_6$) δ 9.18-8.88 (m, 2H), 3.90-3.57 (m, 2H), 3.21-3.07 (m, 1H), 3.07-2.87 (m, 3H), 1.98-1.87 (m, 1H), 1.87-1.68 (m, 3H), 1.68-1.53 (m, 2H). |
| 41 | 1-(3-Methyl-1,2,4-oxadiazol-5-yl)azepan-4-one | 1 (from Step 3) | 40 and 2 | LCMS (System 4, Method B): m/z 196 (M + H)$^+$ (ES$^+$), at 3.34 min, 202 nm |
| 42 | 4-Ethyl-1-oxa-3,8-diazaspiro[4.5]decan-2-one | — | — | See WO2016147011 |
| 43 | 4,4-Dimethyl-1-oxa-3,8-diazaspiro[4.5]decan-2-one | — | — | See WO2016147011 |
| 44 | Spiro[indole-3,4'-piperidin]-2(1H)-one | — | — | Commercially available, CAS: 252882-61-4 |
| 45 | Methyl (2R,4R)-4-fluoropyrrolidine-2-carboxylate hydrochloride salt | — | — | Commercially available, CAS: 1445948-46-8 |
| 46 | tert-Butyl 4-oxopiperidine-1-carboxylate | — | — | Commercially available, CAS: 79099-07-3 |
| 47 | [(2R,4R)-4-Fluoro-1-(piperidin-4-yl)pyrrolidin-2-yl]methanol trifluoroacetic acid salt | 5 | 45 and 46 | LCMS (System 4, Method B): m/z 203 (M + H)$^+$ (ES$^+$), at 2.10 min, 202 nm |
| 48 | [(2R)-4,4-Difluoro-1-(piperidin-4-yl)pyrrolidin-2-yl]methanol | — | — | See WO2017021728 |
| 49 | (5S)-5-Ethyl-1-(piperidin-4-yl)pyrrolidin-2-one | — | — | See WO2017021728 |
| 50 | 1-Methyl-4-(pyrrolidin-2-yl)-1H-pyrazole | — | — | Commercially available, CAS: 1170640-87-5 |
| 51 | 4-[2-(1-Methyl-1H-pyrazol-4-yl)pyrrolidin-1-yl]piperidine | 6 | 50 and 46 | LCMS (System 2, Method A): m/z 235 (M + H)$^+$ (ES$^+$), at 0.27 min, 202 nm |
| 52 | N-Ethyl-N-(piperidin-4-yl)acetamide | — | — | Commercially available, CAS: 139062-99-0 Also see WO2017021730 |
| 53 | tert-Butyl (2S)-2-(piperidin-4-yl)pyrrolidine-1-carboxylate | — | — | Commercially available, CAS: 1449131-15-0 |
| 54 | tert-Butyl (2S)-2-{1-[1-(3-methyl-1,2,4-oxadiazol-5-yl)azepan-4-yl]piperidin-4-yl}pyrrolidine-1-carboxylate | A | 54 and 41 | LCMS (System 3, Method F): m/z 434 (M + H)$^+$ (ES$^+$), at 3.69 min, 202 nm |
| 55 | Methylcarbamyl chloride | — | — | Commercially available, CAS: 6452-47-7 |
| 56 | tert-Butyl 3-oxo-6-azabicyclo[3.2.1]octane-6-carboxylate | — | — | Commercially available, CAS: 359779-74-1 |
| 57 | 6-Azabicyclo[3.2.1]octan-3-ol trifluoroacetic acid salt | 4 | 56 | LCMS (System 4, Method B): m/z 128 (M + H)$^+$ (ES$^+$), at 1.46 min, 202 nm |
| 58 | 6-(3-Methyl-1,2,4-oxadiazol-5-yl)-6-azabicyclo[3.2.1]octan-3-one | 1 (from Step 3) | 56 and 2 | LCMS (System 4, Method B): m/z 208 (M + H)$^+$ (ES$^+$), at 3.88 min, 202 nm |
| 59 | 2,2,2-Trifluoro-N-hydroxyacetimidamide | — | — | Commercially available, CAS: 4314-35-6 |
| 60 | 8-(3-(Trifluoromethyl)-1,2,4-oxadiazol-5-yl)-8-azabicyclo[3.2.1]octan-3-one | 7 | 17 and 59 | 1H NMR (400 MHz, DMSO-d$_6$) δ 4.72-4.62 (m, 2H), 2.89-2.77 (m, 2H), 2.39-2.28 (m, 2H), 2.23-2.09 (m, 2H), 1.79-1.67 (m, 2H). |

TABLE 2-continued

Table 2 - Starting Materials and Intermediates

| Intermediate Number | Name | Synthetic Route | Intermediates Used | Data |
|---|---|---|---|---|
| 61 | 1-Methylcyclobutan-1-amine hydrochloride | — | — | Commercially available, CAS: 174886-05-6 |
| 62 | (1R,5S,6r)-N-(1-methylcyclobutyl)-3-azabicyclo[3.1.0]hexane-6-carboxamide hydrochloride salt | 8 | 9 and 61 | LCMS (System 3, Method F): m/z 193 (M − H)$^-$ (ES$^-$), at 1.92 min, 202 nm |
| 63 | 1-(Trifluoromethyl)cyclobutan-1-amine hydrochloride | — | — | Commercially available, CAS: 1260768-75-9 |
| 64 | 1-Ethylcyclobutan-1-amine hydrochloride | — | — | Commercially available, CAS: 279215-56-4 |
| 65 | 1-Methylcyclopentan-1-amine hydrochloride | — | — | Commercially available, CAS: 102014-58-4 |
| 66 | 1-(tert-Butyl) 4-ethyl piperidine-1,4-dicarboxylate | — | — | Commercially available, CAS: 142851-03-4 |
| 67 | (1-Methylcyclobutyl)methanamine | — | — | Commercially available, CAS: 933722-69-1 |
| 68 | N-((1-Methylcyclobutyl)methyl)piperidine-4-carboxamide trifluoroacetic acid salt | 9 | 66 and 67 | LCMS (System 3, Method F): m/z 211 (M + H)$^+$ (ES$^+$), at 2.39 min, 202 nm |
| 69 | Ethyl 1-(8-(3-(trifluoromethyl)-1,2,4-oxadiazol-5-yl)-8-azabicyclo[3.2.1]octan-3-yl)piperidine-4-carboxylate | A | 23 and 60 | LCMS (System 3, Method F): m/z 403 (M + H)$^+$ (ES$^+$), at 4.06 min, 239 nm |

TABLE 3

Table 3 - NMR and LCMS properties and the methods used to prepare and purify compounds represented by Examples 1 - 12-14

| Ex. No. | Name | Synthetic Method and Intermediates Used | Purification Method | $^1$H NMR | LCMS System and Method | LCMS data |
|---|---|---|---|---|---|---|
| 1-1 | 2-(3-Methyl-1,2,4-oxadiazol-5-yl)-6-[4-(1H-pyrazol-1-yl)piperidin-1-yl]-2-azaspiro[3.3]heptane | A 3 and 4 | A | $^1$H NMR (400 MHz, Methanol-$d_4$) δ 7.67 (d, J = 2 Hz, 1H), 7.48 (d, J = 2 Hz, 1H), 6.29 (t, J = 2 Hz, 1H), 4.25 (s, 2H), 4.23-4.15 (m, 1H), 4.14 (s, 2H), 3.03-2.93 (m, 2H), 2.81-2.68 (m, 1H), 2.51-2.41 (m, 2H), 2.16 (s, 3H), 2.21-1.94 (m, 8H). | System 3 Method F | m/z 329 (M + H)$^+$ (ES$^+$), at 2.76 min, 202 nm |
| 2-1 | Isomer 2: 6-(3-Methyl-1,2,4-oxadiazol-5-yl)-2-[4-(1H-pyrazol-1-yl)piperidin-1-yl]-6-azaspiro[3.4]octane | A 4 and 7 | B | $^1$H NMR (400 MHz, Methanol-$d_4$) δ 7.68 (d, J = 2 Hz, 1H), 7.49 (d, J = 2 Hz, 1H), 6.29 (t, J = 2 Hz, 1H), 4.27-4.15 (m, 1H), 3.59 (t, J = 6.8 Hz, 2H), 3.47 (s, 2H), 3.06-2.99 (m, 2H), 2.94-2.83 (m, 1H), 2.24-2.18 (m, 2H), 2.17 (s, 3H), 2.14-2.07 (m, 4H), 2.06-1.96 (m, 6H). | System 3 Method F | m/z 343 (M + H)$^+$ (ES$^+$), at 2.82 min, 202 nm |
| 2-2 | Isomer 2: 1-[6-(3-Methyl-1,2,4-oxadiazol-5-yl)-6-azaspiro[3.4]oct-2-yl]-4-phenylpiperidine-4-carbonitrile | A 7 and 8 | C | $^1$H NMR (400 MHz, Methanol-$d_4$) δ 7.58-7.50 (m, 2H), 7.48-7.39 (m, 2H), 7.40-7.31 (m, 1H), 3.60 (t, J = 6.8 Hz, 2H), 3.47 (s, 2H), 3.06 (d, J = 12.2 Hz, 2H), 3.03-2.90 (m, 1H), 2.36-2.19 (m, 4H), 2.17 (s, 3H), 2.19-2.06 (m, 6H), 2.06-1.97 (m, 2H). | System 3 Method F | m/z 378 (M + H)$^+$ (ES$^+$), at 3.84 min, 202 nm |
| 2-3 | Isomer 2: Ethyl (1R,5S,6r)-3-[6-(3-methyl-1,2,4-oxadiazol-5-yl)-6-azaspiro[3.4]oct-2-yl]-3-azabicyclo[3.1.0]hexane-6-carboxylate | A 7 and 9 | D | $^1$H NMR (400 MHz, Methanol-$d_4$) δ 4.10 (q, J = 7.1 Hz, 2H), 3.59-3.50 (m, 2H), 3.44 (s, 2H), 3.09-3.00 (m, 3H), 2.44-2.36 (m, 2H), 2.16 (s, 3H), 2.13-2.02 (m, 3H), 2.02-1.92 (m, 6H), 1.24 (t, J = 7.1 Hz, 3H). | System 3 Method F | m/z 347 (M + H)$^+$ (ES$^+$), at 3.52 min, 202 nm |
| 3-1 | Isomer 2: 2-(3-Methyl-1,2,4-oxadiazol-5-yl)-6-[4-(1H-pyrazol-1-yl)piperidin-1-yl]-2-azaspiro[3.4]octane | A 4 and 12 | E | $^1$H NMR (400 MHz, Methanol-$d_4$) δ 7.68 (d, J = 2 Hz, 1H), 7.48 (d, J = 2 Hz, 1H), 6.29 (t, J = 2 Hz, 1H), 4.26-4.12 (m, 2H), 4.12-3.99 (m, 3H), 3.15 (d, J = 11.5 Hz, 2H), 2.77-2.68 (m, 1H), 2.33-2.18 (m, 2H), 2.16 (s, 3H), 2.15-1.91 (m, 8H), 1.87-1.76 (m, 1H), 1.66-1.53 (m, 1H). | System 3 Method F | m/z 343 (M + H)$^+$ (ES$^+$), at 2.72 min, 202 nm |
| 4-1 | 1'-(3-Methyl-1,2,4-oxadiazol-5-yl)-4-(1H-pyrazol-1-yl)-1,4'-bipiperidine | A 4 and 14 | F | $^1$H NMR (400 MHz, Methanol-$d_4$) δ 7.68 (d, J = 2 Hz, 1H), 7.48 (d, J = 2 Hz, 1H), 6.29 (t, J = 2 Hz, 1H), 4.21-4.10 (m, 3H), 3.22-3.08 (m, 4H), 2.72-2.67 (m, 1H), 2.53-2.42 (m, 2H), 2.17 (s, 3H), 2.16-2.09 (m, 2H), 2.08-1.95 (m, 4H), 1.68-1.55 (m, 2H). | System 3 Method F | m/z 317 (M + H)$^+$ (ES$^+$), at 2.60 min, 202 nm |
| 5-1 | Isomer 1: 3-(3-Methyl-1,2,4-oxadiazol-5-yl)-6-[4-(1H-pyrazol-1-yl)piperidin-1-yl]-3-azabicyclo[3.1.1]heptane | A 4 and 16 | G | $^1$H NMR (400 MHz, Methanol-$d_4$) δ 7.70 (d, J = 2 Hz, 1H), 7.49 (d, J = 2 Hz, 1H), 6.29 (t, J = 2 Hz, 1H), 4.28-4.16 (m, 1H), 3.89 (d, J = 10.9 Hz, 2H), 3.72 (d, J = 10.9 Hz, 2H), 3.38-3.21 (m, 2H), 2.72-2.63 (m, 1H), 2.57 (d, J = 6.4 Hz, 2H), 2.41 (d, J = 5.2 Hz, 2H), 2.20 (s, 3H), 2.16-2.07 (m, 4H), 2.04 (d, J = 10.9 Hz, 1H), 1.56-1.49 (m, 1H), 1.31-1.26 (m, 1H). | System 3 Method F | m/z 329 (M + H)$^+$ (ES$^+$), at 2.88 min, 202 nm |
| 6-1 | Isomer 1: 8-(3-Methyl-1,2,4-oxadiazol-5-yl)-3-[4-(1H-pyrazol-1-yl)piperidin-1-yl]-8-azabicyclo[3.2.1]octane | A 4 and 18 | H | $^1$H NMR (400 MHz, Methanol-$d_4$) δ 7.65 (d, J = 2 Hz, 1H), 7.47 (d, J = 2 Hz, 1H), 6.27 (t, J = 2 Hz, 1H), 4.46-4.40 (m, 2H), 4.20-4.10 (m, 1H), 3.08 (t, J = 11.8 Hz, 2H), 3.00-2.89 (m, 1H), 2.34-2.23 (m, 2H), 2.20 (s, 3H), 2.15-2.04 (m, 4H), 2.02-1.93 (m, 4H), 1.93-1.86 (m, 2H), 1.76-1.66 (m, 2H). | System 3 Method F | m/z 343 (M + H)$^+$ (ES$^+$), at 2.75 min, 202 nm |

TABLE 3-continued

Table 3 - NMR and LCMS properties and the methods used to prepare and purify compounds represented by Examples 1 - 12-14

| Ex. No. | Name | Synthetic Method and Intermediates Used | Purification Method | $^1$H NMR | LCMS System and Method | LCMS data |
|---|---|---|---|---|---|---|
| 6-2 | Isomer 1: 8-[8-(3-Methyl-1,2,4-oxadiazol-5-yl)-8-azabicyclo[3.2.1]oct-3-yl]-2,8-diazaspiro[4.5]decan-3-one | A 18 and 19 | I | $^1$H NMR (400 MHz, Methanol-d$_4$) δ 4.47-4.35 (m, 2H), 3.17 (s, 2H), 2.91-2.78 (m, 1H), 2.66-2.34 (m, 4H), 2.24-2.15 (m, 6H), 2.14-2.04 (m, 2H), 2.01-1.91 (m, 2H), 1.91-1.80 (m, 2H), 1.76-1.53 (m, 5H). One exchangeable proton not observed. | System 3 Method F | m/z 346 (M + H)$^+$ (ES$^+$), at 2.14 min, 202 nm |
| 6-2 | Isomer 2: 8-[8-(3-Methyl-1,2,4-oxadiazol-5-yl)-8-azabicyclo[3.2.1]oct-3-yl]-2,8-diazaspiro[4.5]decan-3-one | A 18 and 19 | I | $^1$H NMR (400 MHz, Methanol-d$_4$) δ 4.40-4.27 (m, 2H), 3.19 (s, 2H), 2.74-2.41 (m, 4H), 2.40-2.29 (m, 1H), 2.28-2.13 (m, 7H), 2.11-1.98 (m, 4H), 1.92-1.80 (m, 2H), 1.78-1.62 (m, 4H). One exchangeable proton not observed. | System 3 Method F | m/z 346 (M + H)$^+$ (ES$^+$), at 2.25 min, 202 nm |
| 6-3 | Isomer 2: 8-[8-(3-Ethyl-1,2,4-oxadiazol-5-yl)-8-azabicyclo[3.2.1]oct-3-yl]-2,8-diazaspiro[4.5]decan-3-one | A 19 and 21 | J | $^1$H NMR (400 MHz, Methanol-d$_4$) δ 4.38-4.31 (m, 2H), 3.18 (s, 2H), 2.56 (q, J = 7.6 Hz, 2H), 2.57-2.39 (m, 4H), 2.32-2.22 (m, 1H), 2.24-2.13 (m, 5H), 2.13-1.98 (m, 2H), 1.88 (dd, J = 14.5, 5.6 Hz, 2H), 1.74-1.59 (m, 5H), 1.25 (t, J = 7.6 Hz, 3H). One exchangeable proton not observed. | System 3 Method F | m/z 360 (M + H)$^+$ (ES$^+$), at 2.56 min, 202 nm |
| 6-4 | Isomer 1: 8-[8-(3-Methyl-1,2,4-oxadiazol-5-yl)-8-azabicyclo[3.2.1]octan-3-yl]-1-oxa-3,8-diazaspiro[4.5]decan-2-one | A 18 and 22 | K | $^1$H NMR (400 MHz, Methanol-d$_4$) δ 4.48-4.37 (m, 2H), 3.33 (s, 2H), 2.98-2.84 (m, 1H), 2.74-2.62 (m, 2H), 2.56 (t, J = 10.9 Hz, 2H), 2.19 (s, 3H), 2.15-2.03 (m, 2H), 2.00-1.83 (m, 6H), 1.82-1.62 (m, 4H). One exchangeable proton not observed. | System 3 Method F | m/z 348 (M + H)$^+$ (ES$^+$), at 2.28 min, 202 nm |
| 6-4 | Isomer 2: 8-[8-(3-Methyl-1,2,4-oxadiazol-5-yl)-8-azabicyclo[3.2.1]octan-3-yl]-1-oxa-3,8-diazaspiro[4.5]decan-2-one | A 18 and 22 | K | $^1$H NMR (400 MHz, Methanol-d$_4$) δ 4.41-4.26 (m, 2H), 3.35 (s, 2H), 2.79-2.44 (m, 4H), 2.39-2.29 (m, 1H), 2.18 (s, 3H), 2.17-2.08 (m, 4H), 2.08-2.01 (m, 2H), 2.00-1.89 (m, 4H), 1.89-1.79 (m, 2H). One exchangeable proton not observed. | System 3 Method F | m/z 348 (M + H)$^+$ (ES$^+$), at 2.40 min, 202 nm |
| 6-5 | Isomer 2: N-(1-Methylcyclobutyl)-1-[8-(3-methyl-1,2,4-oxadiazol-5-yl)-8-azabicyclo[3.2.1]oct-3-yl]piperidine-4-carboxamide | B 24 and 25 | L | $^1$H NMR (400 MHz, Methanol-d$_4$) δ 4.37-4.29 (m, 2H), 3.21 (d, J = 11.2 Hz, 2H), 2.30-2.20 (m, 2H), 2.20-1.93 (m, 10H), 2.18 (s, 3H), 1.93-1.78 (m, 6H), 1.78-1.63 (m, 4H), 1.41 (s, 3H). One exchangeable proton not observed. | System 3 Method F | m/z 388 (M + H)$^+$ (ES$^+$), at 3.06 min, 202 nm |
| 7-1 | Isomer 1: 2-(3-Methyl-1,2,4-oxadiazol-5-yl)-5-[4-(1H-pyrazol-1-yl)piperidin-1-yl]-2-azabicyclo[2.2.2]octane | A 4 and 28 | M | $^1$H NMR (400 MHz, Methanol-d$_4$) δ 7.68 (d, J = 2 Hz, 1H), 7.49 (d, J = 2 Hz, 1H), 6.29 (t, J = 2 Hz, 1H), 4.28-4.14 (m, 1H), 4.06-3.99 (m, 1H), 3.65-3.58 (m, 1H), 3.52-3.44 (m, 1H), 3.38-3.15 (m, 2H), 2.46-2.38 (m, 1H), 2.34-2.29 (m, 1H), 2.29-2.19 (m, 1H), 2.17 (s, 3H), 2.15-1.99 (m, 7H), 1.95-1.78 (m, 2H), 1.66-1.53 (m, 2H). | System 3 Method F | m/z 343 (M + H)$^+$ (ES$^+$), at 2.87 min, 202 nm |
| 7-1 | Isomer 2: 2-(3-Methyl-1,2,4-oxadiazol-5-yl)-5-[4-(1H-pyrazol-1-yl)piperidin-1-yl]-2-azabicyclo[2.2.2]octane | A 4 and 28 | M | $^1$H NMR (400 MHz, Methanol-d$_4$) δ 7.67 (d, J = 2 Hz, 1H), 7.47 (d, J = 2 Hz, 1H), 6.28 (t, J = 2 Hz, 1H), 4.27-4.14 (m, 1H), 4.08-4.01 (m, 1H), 3.81-3.71 (m, 1H), 3.44-3.36 (m, 1H), 3.31-3.18 (m, 2H), 2.46-2.30 (m, 2H), 2.17 (s, 3H), 2.14-1.98 (m, 7H), 1.97-1.74 (m, 3H), 1.71 (d, J = 8.2 Hz, 2H). | System 3 Method F | m/z 343 (M + H)$^+$ (ES$^+$), at 2.99 min, 202 nm |

TABLE 3-continued

Table 3 - NMR and LCMS properties and the methods used to prepare and purify compounds represented by Examples 1 - 12-14

| Ex. No. | Name | Synthetic Method and Intermediates Used | Purification Method | ¹H NMR | LCMS System and Method | LCMS data |
|---|---|---|---|---|---|---|
| 8-1 | Isomer 2: 9-(3-Methyl-1,2,4-oxadiazol-5-yl)-3-[4-(1H-pyrazol-1-yl)piperidin-1-yl]-9-azabicyclo[3.3.1]nonane | A 4 and 31 | N then O | ¹H NMR (400 MHz, Methanol-$d_4$) δ 7.66 (d, J = 2 Hz, 1H), 7.48 (d, J = 2 Hz, 1H), 6.28 (t, J = 2 Hz, 1H), 4.42-4.33 (m, 2H), 4.24-4.13 (m, 1H), 3.44-3.34 (m, 1H), 3.20 (d, J = 11.8 Hz, 2H), 2.40-2.28 (m, 2H), 2.18 (s, 3H), 2.16-2.07 (m, 4H), 2.06-1.89 (m, 4H), 1.89-1.77 (m, 3H), 1.76-1.67 (m, 1H), 1.40-1.19 (m, 1H), 1.15 (d, J = 6.2 Hz, 0.3H), 0.95-0.82 (m, 0.7H). | System 3 Method F | m/z 357 (M + H)⁺ (ES⁺), at 3.01 min, 215 nm |
| 8-2 | Isomer 1: 8-[9-(3-Methyl-1,2,4-oxadiazol-5-yl)-9-azabicyclo[3.3.1]non-3-yl]-2,8-diazaspiro[4.5]decan-3-one | A 19 and 31 | P | ¹H NMR (400 MHz, Methanol-$d_4$) δ 4.45 (d, J = 10.7 Hz, 2H), 3.19 (s, 2H), 2.65-2.55 (m, 4H), 2.44-2.29 (m, 3H), 2.21 (s, 2H), 2.19-1.99 (m, 2H), 2.16 (s, 3H), 1.79-1.66 (m, 6H), 1.62-1.49 (m, 4H). One exchangeable proton not observed. | System 3 Method F | m/z 360 (M + H)⁺ (ES⁺), at 2.45 min, 202 nm |
| 8-3 | Isomer 1: 8-[9-(3-Methyl-1,2,4-oxadiazol-5-yl)-9-azabicyclo[3.3.1]non-3-yl]-1-oxa-3,8-diazaspiro[4.5]decan-2-one | A 22 and 31 | Q | ¹H NMR (400 MHz, Methanol-$d_4$) δ 4.46 (d, J = 10.3 Hz, 2H), 3.35 (s, 2H), 2.77-2.63 (m, 4H), 2.48-2.31 (m, 3H), 2.19-2.02 (m, 1H), 2.16 (s, 3H), 2.00-1.90 (m, 2H), 1.87-1.67 (m, 4H), 1.64-1.49 (m, 5H). One exchangeable proton not observed. | System 3 Method F | m/z 362 (M + H)⁺ (ES⁺), at 2.43 min, 202 nm |
| 8-4 | Isomer 1: N-(1-Methylcyclobutyl)-1-[9-(3-methyl-1,2,4-oxadiazol-5-yl)-9-azabicyclo[3.3.1]non-3-yl]piperidine-4-carboxamide | B 32 and 25 | R then S | ¹H NMR (400 MHz, Methanol-$d_4$) δ 4.58-4.36 (m, 2H), 3.11 (d, J = 11.7 Hz, 2H), 2.49-2.20 (m, 7H), 2.16 (s, 3H), 2.13-2.04 (m, 1H), 2.02-1.90 (m, 3H), 1.88-1.67 (m, 8H), 1.65-1.48 (m, 5H), 1.41 (s, 3H). | System 3 Method F | m/z 402 (M + H)⁺ (ES⁺), at 3.16 min, 202 nm |
| 9-1 | Isomer 1: 9-(3-Methyl-1,2,4-oxadiazol-5-yl)-7-[4-(1H-pyrazol-1-yl)piperidin-1-yl]-3-oxa-9-azabicyclo[3.3.1]nonane | A 4 and 35 | T then U | ¹H NMR (400 MHz, Methanol-$d_4$) δ 7.66 (d, J = 2 Hz, 1H), 7.47 (d, J = 2 Hz, 1H), 6.28 (t, J = 2 Hz, 1H), 4.24-4.10 (m, 3H), 3.95 (d, J = 11.7 Hz, 2H), 3.87-3.72 (m, 3H), 3.18-3.09 (m, 2H), 2.41-2.29 (m, 2H), 2.23-2.15 (m, 2H), 2.20 (s, 3H), 2.15-2.07 (m, 2H), 2.04-1.92 (m, 2H), 1.91-1.79 (m, 2H). | System 3 Method F | m/z 359 (M + H)⁺ (ES⁺), at 2.43 min, 220 nm |
| 9-2 | Isomer 2: (1R,5S,6r)-N,N-Diethyl-3-[9-(3-methyl-1,2,4-oxadiazol-5-yl)-3-oxa-9-azabicyclo[3.3.1]non-7-yl]-3-azabicyclo[3.1.0]hexane-6-carboxamide | B 37 and 38 | V | ¹H NMR (400 MHz, Methanol-$d_4$) δ 4.13-4.03 (m, 2H), 3.96-3.86 (m, 2H), 3.86-3.76 (m, 2H), 3.67-3.61 (m, 1H), 3.52-3.39 (m, 2H), 3.39-3.31 (m, 2H), 3.20-3.08 (m, 1H), 2.58-2.32 (m, 3H), 2.24-2.07 (m, 2H), 2.19 (s, 3H), 1.98-1.88 (m, 2H), 1.79-1.65 (m, 2H), 1.22 (t, J = 7.1 Hz, 3H), 1.12-1.01 (m, 3H). | System 3 Method F | m/z 390 (M + H)⁺ (ES⁺), at 2.75 min, 202 nm |
| 10-1 | Isomer 1: 1-(3-Methyl-1,2,4-oxadiazol-5-yl)-4-[4-(1H-pyrazol-1-yl)piperidin-1-yl]azepane | A 4 and 41 | W then X | ¹H NMR (400 MHz, Chloroform-d) δ 7.50-7.48 (m, 1H), 7.43-7.41 (m, 1H), 6.26-6.22 (m, 1H), 4.17-4.06 (m, 1H), 3.81-3.67 (m, 2H), 3.56-3.40 (m, 2H), 2.98-2.86 (m, 2H), 2.64-2.52 (m, 2H), 2.48-2.32 (m, 2H), 2.21 (t, J = 0.5 Hz, 3H), 2.20-2.11 (m, 2H), 2.10-1.88 (m, 5H), 1.85-1.73 (m, 1H), 1.72-1.59 (m, 1H), 1.58-1.45 (m, 1H). | System 5 Method G | m/z 331 (M + H)⁺ (ES⁺), at 2.94 min, 254 nm |
| 10-1 | Isomer 1: 1-(3-Methyl-1,2,4-oxadiazol-5-yl)-4-[4-(1H-pyrazol-1-yl)piperidin-1-yl]azepane | A 4 and 41 | W then X | ¹H NMR (400 MHz, Chloroform-d) δ 7.50-7.48 (m, 1H), 7.42 (d, J = 2.3 Hz, 1H), 6.25-6.23 (m, 1H), 4.15-4.05 (m, 1H), 3.80-3.67 (m, 1H), 3.55-3.40 (m, 1H), 2.95-2.86 (m, 2H), 2.61-2.52 (m, 1H), 2.45-2.33 (m, 2H), 2.21 (s, 3H), 2.18-2.10 (m, 2H), 2.08-1.87 (m, 5H), 1.84-1.72 (m, 1H), 1.72-1.59 (m, 1H), 1.55-1.44 (m, 1H). | System 5 Method G | m/z 331 (M + H)⁺ (ES⁺), at 2.95 min, 254 nm |

TABLE 3-continued

Table 3 - NMR and LCMS properties and the methods used to prepare and purify compounds represented by Examples 1 - 12-14

| Ex. No. | Name | Synthetic Method and Intermediates Used | Purification Method | ¹H NMR | LCMS System and Method | LCMS data |
|---|---|---|---|---|---|---|
| 10-2 | Isomer 1: 8-[1-(3-Methyl-1,2,4-oxadiazol-5-yl)azepan-4-yl]-2,8-diazaspiro[4.5]decan-3-one | A 19 and 41 | Y then Z | ¹H NMR (400 MHz, Methanol-$d_4$) δ 3.82-3.63 (m, 2H), 3.59-3.44 (m, 2H), 3.18 (s, 2H), 2.62-2.44 (m, 6H), 2.20 (s, 2H), 2.17 (s, 3H), 2.13-2.02 (m, 1H), 2.03-1.91 (m, 1H), 1.86-1.74 (m, 1H), 1.73-1.60 (m, 5H), 1.58-1.45 (m, 1H). One exchangeable proton not observed. | System 3 Method F | m/z 334 (M + H)⁺ (ES⁺), at 1.98 min, 202 nm |
| 10-2 | Isomer 2: 8-[1-(3-Methyl-1,2,4-oxadiazol-5-yl)azepan-4-yl]-2,8-diazaspiro[4.5]decan-3-one | A 19 and 41 | Y then Z | ¹H NMR (400 MHz, Methanol-$d_4$) δ 3.82-3.64 (m, 2H), 3.57-3.44 (m, 2H), 3.18 (s, 2H), 2.63-2.44 (m, 6H), 2.20 (s, 2H), 2.17 (s, 3H), 2.12-2.04 (m, 1H), 2.04-1.93 (m, 1H), 1.86-1.74 (m, 1H), 1.73-1.60 (m, 5H), 1.59-1.47 (m, 1H). One exchangeable proton not observed. | System 3 Method F | m/z 334 (M + H)⁺ (ES⁺), at 1.99 min, 202 nm |
| 10-3 | Racemic mixture: 8-[1-(3-Methyl-1,2,4-oxadiazol-5-yl)azepan-4-yl]-1-oxa-3,8-diazaspiro[4.5]decan-2-one | A 22 and 41 | AA | ¹H NMR (400 MHz, DMSO-$d_6$) δ 7.46 (s, 1H), 3.70-3.55 (m, 2H), 3.47-3.36 (m, 2H), 3.18 (s, 2H), 2.57-2.44 (m, 3H), 2.44-2.36 (m, 2H), 2.08 (s, 3H), 1.93-1.81 (m, 2H), 1.80-1.60 (m, 6H), 1.59-1.48 (m, 1H), 1.48-1.37 (m, 1H). | System 3 Method F | m/z 336 (M + H)⁺ (ES⁺), at 2.13 min, 202 nm |
| 10-4 | Isomer 1: 4-Ethyl-8-[1-(3-methyl-1,2,4-oxadiazol-5-yl)azepan-4-yl]-1-oxa-3,8-diazaspiro[4.5]decan-2-one | A 42 and 41 | AB then AC | ¹H NMR (400 MHz, Methanol-$d_4$) δ 3.83-3.66 (m, 2H), 3.59-3.46 (m, 2H), 3.40-3.34 (m, 1H), 2.89-2.59 (m, 5H), 2.17 (s, 3H), 2.16-2.07 (m, 1H), 2.06-1.97 (m, 2H), 1.97-1.76 (m, 5H), 1.75-1.66 (m, 1H), 1.65-1.51 (m, 2H), 1.50-1.38 (m, 1H), 0.99 (t, J = 7.4 Hz, 3H). One exchangeable proton not observed. | System 3 Method F | m/z 364 (M + H)⁺ (ES⁺), at 2.42 min, 228 nm |
| 10-4 | Isomer 2: 4-Ethyl-8-[1-(3-methyl-1,2,4-oxadiazol-5-yl)azepan-4-yl]-1-oxa-3,8-diazaspiro[4.5]decan-2-one | A 42 and 41 | AB then AC | ¹H NMR (400 MHz, Methanol-$d_4$) δ 3.81-3.67 (m, 2H), 3.58-3.46 (m, 2H), 3.39-3.33 (m, 1H), 2.83-2.58 (m, 5H), 2.17 (s, 3H), 2.14-2.06 (m, 1H), 2.05-1.95 (m, 2H), 1.95-1.73 (m, 5H), 1.72-1.65 (m, 1H), 1.65-1.52 (m, 2H), 1.51-1.39 (m, 1H), 0.99 (t, J = 7.4 Hz, 3H). One exchangeable proton not observed. | System 3 Method F | m/z 364 (M + H)⁺ (ES⁺), at 2.42 min, 230 nm |
| 10-4 | Isomer 3: 4-Ethyl-8-[1-(3-methyl-1,2,4-oxadiazol-5-yl)azepan-4-yl]-1-oxa-3,8-diazaspiro[4.5]decan-2-one | A 42 and 41 | AB then AC | ¹H NMR (400 MHz, Methanol-$d_4$) δ 3.82-3.63 (m, 2H), 3.60-3.44 (m, 2H), 3.39-3.33 (m, 1H), 2.77-2.52 (m, 5H), 2.17 (s, 3H), 2.13-2.05 (m, 1H), 2.04-1.92 (m, 2H), 1.92-1.71 (m, 5H), 1.70-1.65 (m, 1H), 1.64-1.50 (m, 2H), 1.50-1.38 (m, 1H), 0.98 (t, J = 7.4 Hz, 3H). One exchangeable proton not observed. | System 3 Method F | m/z 364 (M + H)⁺ (ES⁺), at 2.40 min, 202 nm |
| 10-4 | Isomer 4: 4-Ethyl-8-[1-(3-methyl-1,2,4-oxadiazol-5-yl)azepan-4-yl]-1-oxa-3,8-diazaspiro[4.5]decan-2-one | A 42 and 41 | AB then AC | ¹H NMR (400 MHz, Methanol-$d_4$) δ 3.81-3.62 (m, 2H), 3.60-3.46 (m, 2H), 3.38-3.32 (m, 1H), 2.77-2.52 (m, 5H), 2.17 (s, 3H), 2.13-2.04 (m, 1H), 2.04-1.93 (m, 2H), 1.92-1.71 (m, 5H), 1.71-1.63 (m, 1H), 1.62-1.50 (m, 2H), 1.49-1.37 (m, 1H), 0.98 (t, J = 7.4 Hz, 3H). One exchangeable proton not observed. | System 3 Method F | m/z 364 (M + H)⁺ (ES⁺), at 2.40 min, 228 nm |
| 10-5 | Isomer 1: 4,4-Dimethyl-8-[1-(3-methyl-1,2,4-oxadiazol-5-yl)azepan-4-yl]-1-oxa-3,8-diazaspiro[4.5]decan-2-one | A 43 and 41 | AD then AE | ¹H NMR (400 MHz, Methanol-$d_4$) δ 3.81-3.62 (m, 2H), 3.58-3.43 (m, 2H), 2.82-2.69 (m, 2H), 2.65-2.48 (m, 3H), 2.17 (s, 3H), 2.12-2.04 (m, 1H), 2.04-1.78 (m, 5H), 1.77-1.50 (m, 4H), 1.20 (s, 6H). One exchangeable proton not observed. | System 3 Method F | m/z 364 (M + H)⁺ (ES⁺), at 2.32 min, 202 nm |

TABLE 3-continued

Table 3 - NMR and LCMS properties and the methods used to prepare and purify compounds represented by Examples 1 - 12-14

| Ex. No. | Name | Synthetic Method and Intermediates Used | Purification Method | $^1$H NMR | LCMS System and Method | LCMS data |
|---|---|---|---|---|---|---|
| 10-6 | Isomer 1: 1'-[1-[1-(3-Methyl-1,2,4-oxadiazol-5-yl)azepan-4-yl]spiro[indole-3,4'-piperidin]-2(1H)-one | A 44 and 41 | AF then AG | $^1$H NMR (400 MHz, Methanol-$d_4$) δ 7.38 (d, J = 7.5 Hz, 1H), 7.24-7.17 (m, 1H), 7.06-6.98 (m, 1H), 6.90 (d, J = 7.7 Hz, 1H), 3.97-3.88 (m, 1H), 3.84-3.70 (m, 2H), 3.62-3.51 (m, 2H), 3.16-3.05 (m, 2H), 2.86-2.76 (m, 2H), 2.75-2.66 (m, 1H), 2.26-2.15 (m, 1H), 2.18 (s, 3H), 2.14-2.00 (m, 2H), 1.96-1.79 (m, 4H), 1.77-1.58 (m, 2H). One exchangeable proton not observed. | System 3 Method F | m/z 382 (M + H)$^+$ (ES$^+$), at 3.03 min, 202 nm |
| 10-7 | Isomer 1: [(2R,4R)-4-Fluoro-1-{1-[1-(3-methyl-1,2,4-oxadiazol-5-yl)azepan-4-yl]piperidin-4-yl}pyrrolidin-2-yl]methanol | A 47 and 41 | AH then AI | $^1$H NMR (400 MHz, Methanol-$d_4$) δ 5.12 (dt, J = 54.2, 4.4 Hz, 1H), 3.79-3.64 (m, 2H), 3.61-3.45 (m, 3H), 3.45-3.38 (m, 1H), 3.24-3.11 (m, 1H), 3.08-2.97 (m, 1H), 2.91-2.83 (m, 2H), 2.84-2.68 (m, 1H), 2.60-2.48 (m, 2H), 2.38-2.22 (m, 2H), 2.17 (s, 3H), 2.10-1.91 (m, 5H), 1.91-1.72 (m, 3H), 1.72-1.59 (m, 1H), 1.59-1.42 (m, 3H). One exchangeable proton not observed. | System 3 Method F | m/z 382 (M + H)$^+$ (ES$^+$), at 2.37 min, 220 nm |
| 10-7 | Isomer 2: [(2R,4R)-4-Fluoro-1-{1-[1-(3-methyl-1,2,4-oxadiazol-5-yl)azepan-4-yl]piperidin-4-yl}pyrrolidin-2-yl]methanol | A 47 and 41 | AH then AI | $^1$H NMR (400 MHz, Methanol-$d_4$) δ 5.12 (dt, J = 54.1, 4.4 Hz, 1H), 3.80-3.65 (m, 2H), 3.61-3.45 (m, 3H), 3.45-3.37 (m, 1H), 3.23-3.11 (m, 1H), 3.07-2.98 (m, 1H), 2.91-2.84 (m, 2H), 2.84-2.68 (m, 1H), 2.60-2.48 (m, 2H), 2.38-2.26 (m, 2H), 2.17 (s, 3H), 2.13-1.91 (m, 5H), 1.91-1.72 (m, 3H), 1.72-1.57 (m, 1H), 1.57-1.44 (m, 3H). One exchangeable proton not observed. | System 3 Method F | m/z 382 (M + H)$^+$ (ES$^+$), at 2.37 min, 220 nm |
| 10-8 | Isomer 1: [(2R)-4,4-Difluoro-1-{1-[1-(3-methyl-1,2,4-oxadiazol-5-yl)azepan-4-yl]piperidin-4-yl}pyrrolidin-2-yl]methanol | A 48 and 41 | AJ then AK | $^1$H NMR (400 MHz, Methanol-$d_4$) δ 3.81-3.64 (m, 2H), 3.61-3.44 (m, 4H), 3.26-3.11 (m, 2H), 3.10-2.97 (m, 1H), 2.95-2.82 (m, 2H), 2.76-2.64 (m, 1H), 2.64-2.52 (m, 1H), 2.41-2.23 (m, 3H), 2.22-2.14 (m, 1H), 2.17 (s, 3H), 2.12-2.03 (m, 1H), 2.03-1.92 (m, 2H), 1.87-1.73 (m, 3H), 1.71-1.60 (m, 1H), 1.59-1.41 (m, 3H). One exchangeable proton not observed. | System 4 Method D | m/z 400 (M + H)$^+$ (ES$^+$), at 2.48 min, 228 nm |
| 10-8 | Isomer 2: [(2R)-4,4-Difluoro-1-{1-[1-(3-methyl-1,2,4-oxadiazol-5-yl)azepan-4-yl]piperidin-4-yl}pyrrolidin-2-yl]methanol | A 48 and 41 | AJ then AK | $^1$H NMR (400 MHz, Methanol-$d_4$) δ 3.81-3.65 (m, 2H), 3.61-3.44 (m, 4H), 3.26-3.11 (m, 2H), 3.11-2.98 (m, 1H), 2.95-2.83 (m, 2H), 2.76-2.65 (m, 1H), 2.65-2.53 (m, 1H), 2.41-2.26 (m, 3H), 2.24-2.13 (m, 1H), 2.17 (s, 3H), 2.13-2.04 (m, 1H), 2.03-1.91 (m, 2H), 1.87-1.75 (m, 3H), 1.74-1.59 (m, 1H), 1.58-1.44 (m, 3H). One exchangeable proton not observed. | System 4 Method D | m/z 400 (M + H)$^+$ (ES$^+$), at 2.47 min, 202 nm |
| 10-9 | Isomer 2: (5S)-5-Ethyl-1-{1-[1-(3-methyl-1,2,4-oxadiazol-5-yl)azepan-4-yl]piperidin-4-yl}pyrrolidin-2-one | A 49 and 41 | AL then AM | $^1$H NMR (400 MHz, Methanol-$d_4$) δ 3.79-3.66 (m, 3H), 3.66-3.56 (m, 1H), 3.56-3.45 (m, 2H), 2.95-2.81 (m, 2H), 2.61-2.52 (m, 1H), 2.50-2.41 (m, 1H), 2.41-2.30 (m, 2H), 2.30-2.20 (m, 1H), 2.17 (s, 3H), 2.15-1.92 (m, 5H), 1.91-1.74 (m, 5H), 1.73-1.60 (m, 2H), 1.60-1.44 (m, 2H), 0.92 (t, J = 7.4 Hz, 3H). | System 3 Method F | m/z 376 (M + H)$^+$ (ES$^+$), at 2.77 min, 202 nm |

TABLE 3-continued

Table 3 - NMR and LCMS properties and the methods used to prepare and purify compounds represented by Examples 1 - 12-14

| Ex. No. | Name | Synthetic Method and Intermediates Used | Purification Method | ¹H NMR | LCMS System and Method | LCMS data |
|---|---|---|---|---|---|---|
| 10-10 | Isomer 1b: 1-(3-Methyl-1,2,4-oxadiazol-5-yl)-4-{4-[2-(1-methyl-1H-pyrazol-4-yl)pyrrolidin-1-yl]piperidin-1-yl}azepane | A 51 and 41 | AN to give Isomers 1 and 2 then AO to give Isomers 1a and 1b from Isomer 1 | ¹H NMR (400 MHz, Methanol-d₄) δ 7.52 (s, 1H), 7.41 (s, 1H), 3.92-3.81 (m, 1H), 3.85 (s, 3H), 3.77-3.64 (m, 2H), 3.54-3.42 (m, 2H), 2.98-2.89 (m, 1H), 2.88-2.77 (m, 2H), 2.76-2.68 (m, 1H), 2.56-2.46 (m, 1H), 2.38-2.29 (m, 1H), 2.26-2.09 (m, 3H), 2.16 (s, 3H), 2.07-1.82 (m, 6H), 1.81-1.68 (m, 3H), 1.67-1.59 (m, 1H), 1.59-1.41 (m, 3H). | System 3 Method F | m/z 414 (M + H)⁺ (ES⁺), at 2.36 min, 225 nm |
| 10-10 | Isomer 2a: 1-(3-Methyl-1,2,4-oxadiazol-5-yl)-4-{4-[2-(1-methyl-1H-pyrazol-4-yl)pyrrolidin-1-yl]piperidin-1-yl}azepane | A 51 and 41 | AN to give Isomers 1 and 2 then AO to give Isomers 2a and 2b from Isomer 2 | ¹H NMR (400 MHz, Methanol-d₄) δ 7.54 (s, 1H), 7.42 (s, 1H), 3.97-3.89 (m, 1H), 3.86 (s, 3H), 3.77-3.64 (m, 2H), 3.55-3.43 (m, 2H), 3.01-2.91 (m, 1H), 2.89-2.71 (m, 3H), 2.59-2.48 (m, 1H), 2.44-2.33 (m, 1H), 2.28-2.10 (m, 3H), 2.16 (s, 3H), 2.09-1.84 (m, 6H), 1.83-1.68 (m, 3H), 1.67-1.41 (m, 4H). | System 3 Method F | m/z 414 (M + H)⁺ (ES⁺), at 2.34 min, 226 nm |
| 10-10 | Isomer 2b: 1-(3-Methyl-1,2,4-oxadiazol-5-yl)-4-{4-[2-(1-methyl-1H-pyrazol-4-yl)pyrrolidin-1-yl]piperidin-1-yl}azepane | A 51 and 41 | AN to give Isomers 1 and 2 then AO to give Isomers 2a and 2b from Isomer 2 | ¹H NMR (400 MHz, Methanol-d₄) δ 7.52 (s, 1H), 7.41 (s, 1H), 3.92-3.82 (m, 1H), 3.85 (s, 3H), 3.76-3.64 (m, 2H), 3.54-3.42 (m, 2H), 2.98-2.89 (m, 1H), 2.88-2.76 (m, 2H), 2.76-2.68 (m, 1H), 2.56-2.47 (m, 1H), 2.39-2.29 (m, 1H), 2.27-2.09 (m, 3H), 2.16 (s, 3H), 2.08-1.81 (m, 6H), 1.82-1.68 (m, 3H), 1.67-1.54 (m, 2H), 1.54-1.41 (m, 2H). | System 3 Method F | m/z 414 (M + H)⁺ (ES⁺), at 2.34 min, 226 nm |
| 10-11 | Racemic mixture: N-Ethyl-N-{1-[1-(3-methyl-1,2,4-oxadiazol-5-yl)azepan-4-yl]piperidin-4-yl}acetamide | A 52 and 41 | AP | ¹H NMR (400 MHz, DMSO-d₆) δ 4.17-4.01 (m, 1H), 3.75-3.52 (m, 2H), 3.52-3.34 (m, 2H), 3.27-3.09 (m, 4H), 2.83-2.70 (m, 2H), 2.24-2.12 (m, 2H), 2.09 (s, 3H), 1.98 (d, J = 5.5 Hz, 3H), 1.93-1.81 (m, 2H), 1.80-1.65 (m, 2H), 1.65-1.36 (m, 5H), 1.03 (dt, J = 40.8, 6.9 Hz, 3H). | System 3 Method F | m/z 350 (M + H)⁺ (ES⁺), at 2.37 min, 202 nm |
| 10-12 | Isomer 1: (2S)-N-Methyl-2-{1-[1-(3-methyl-1,2,4-oxadiazol-5-yl)azepan-4-yl]piperidin-4-yl}pyrrolidine-1-carboxamide | C 54 and 55 | AQ then AR | ¹H NMR (400 MHz, Methanol-d₄) δ 3.90-3.80 (m, 1H), 3.79-3.63 (m, 3H), 3.60-3.43 (m, 3H), 2.93-2.80 (m, 2H), 2.71 (s, 3H), 2.61-2.50 (m, 1H), 2.35-2.21 (m, 2H), 2.16 (s, 3H), 2.13-2.05 (m, 1H), 2.03-1.94 (m, 2H), 1.94-1.69 (m, 6H), 1.68-1.45 (m, 4H), 1.43-1.31 (m, 2H). One exchangeable proton not observed. | System 3 Method F | m/z 391 (M + H)⁺ (ES⁺), at 2.10 min, 225 nm |
| 10-12 | Isomer 2: (2S)-N-Methyl-2-{1-[1-(3-methyl-1,2,4-oxadiazol-5-yl)azepan-4-yl]piperidin-4-yl}pyrrolidine-1-carboxamide | C 54 and 55 | AQ then AR | ¹H NMR (400 MHz, Methanol-d₄) δ 3.90-3.81 (m, 1H), 3.80-3.63 (m, 3H), 3.59-3.44 (m, 3H), 3.01-2.86 (m, 2H), 2.76-2.58 (m, 1H), 2.71 (s, 3H), 2.46-2.27 (m, 2H), 2.21-2.07 (m, 1H), 2.17 (s, 3H), 2.07-1.96 (m, 2H), 1.95-1.87 (m, 2H), 1.87-1.71 (m, 4H), 1.71-1.49 (m, 4H), 1.48-1.32 (m, 2H). One exchangeable proton not observed. | System 3 Method F | m/z 391 (M + H)⁺ (ES⁺), at 2.08 min, 225 nm |

TABLE 3-continued

Table 3 - NMR and LCMS properties and the methods used to prepare and purify compounds represented by Examples 1 - 12-14

| Ex. No. | Name | Synthetic Method and Intermediates Used | Purification Method | ¹H NMR | LCMS System and Method | LCMS data |
|---|---|---|---|---|---|---|
| 11-1 | Isomer 2: 6-(3-Methyl-1,2,4-oxadiazol-5-yl)-3-[4-(1H-pyrazol-1-yl)piperidin-1-yl]-6-azabicyclo[3.2.1]octane | A 4 and 58 | AS | ¹H NMR (400 MHz, Methanol-d₄) δ 7.61 (d, J = 2 Hz, 1H), 7.45 (d, J = 2 Hz, 1H), 6.28 (t, J = 2 Hz, 1H), 4.23-4.16 (m, 1H), 4.13-4.02 (m, 1H), 3.63 (d, J = 9.7 Hz, 1H), 3.52-3.44 (m, 1H), 3.15-3.05 (m, 3H), 2.61-2.50 (m, 2H), 2.33-2.21 (m, 1H), 2.17 (s, 3H), 2.11-1.80 (m, 11H), 1.63-1.49 (m, 1H). | System 3 Method F | m/z 343 (M + H)⁺ (ES⁺), at 2.89 min, 202 nm |
| 11-2 | Isomer 2: 8-[6-(3-Methyl-1,2,4-oxadiazol-5-yl)-6-azabicyclo[3.2.1]oct-3-yl]-2,8-diazaspiro[4.5]decan-3-one | A 19 and 58 | AT | ¹H NMR (400 MHz, Methanol-d₄) δ 4.21-4.15 (m, 1H), 3.58 (d, J = 9.6 Hz, 1H), 3.49-3.43 (m, 1H), 3.12 (s, 2H), 2.60-2.52 (m, 2H), 2.52-2.40 (m, 3H), 2.38-2.27 (m, 2H), 2.18 (s, 3H), 2.14 (s, 2H), 2.10-2.01 (m, 2H), 1.97-1.92 (m, 1H), 1.91-1.81 (m, 4H), 1.63-1.52 (m, 1H), 1.52-1.39 (m, 1H). One exchangeable proton not observed. | System 3 Method F | m/z 346 (M + H)⁺ (ES⁺), at 2.10 min, 202 nm |
| 11-3 | Isomer 2: 8-[6-(3-Methyl-1,2,4-oxadiazol-5-yl)-6-azabicyclo[3.2.1]oct-3-yl]-1-oxa-3,8-diazaspiro[4.5]decan-2-one | A 22 and 58 | AU | ¹H NMR (400 MHz, Methanol-d₄) δ 4.24-4.13 (m, 1H), 3.60 (d, J = 9.6 Hz, 1H), 3.52-3.42 (m, 1H), 2.77-2.31 (m, 6H), 2.30-2.13 (m, 2H), 2.18 (s, 3H), 2.09-1.98 (m, 2H), 1.97-1.80 (m, 5H), 1.79-1.68 (m, 2H), 1.57-1.42 (m, 1H). One exchangeable proton not observed. | System 3 Method F | m/z 348 (M + H)⁺ (ES⁺), at 2.32 min, 210 nm |
| 12-1 | Isomer 1: 8-(2-(3-Methyl-1,2,4-oxadiazol-5-yl)-2-azabicyclo[2.2.2]octan-5-yl)-2,8-diazaspiro[4.5]decan-3-one | A 19 and 28 | AV | ¹H NMR (400 MHz, Methanol-d₄) δ 4.05-3.97 (m, 1H), 3.64-3.55 (m, 1H), 3.50-3.42 (m, 1H), 3.21 (s, 2H), 2.73-2.22 (m, 4H), 2.38-2.28 (m, 2H), 2.27-2.20 (m, 3H), 2.16 (s, 3H), 2.07-1.94 (m, 1H), 1.92-1.79 (m, 2H), 1.77-1.65 (m, 4H), 1.63-1.49 (m, 2H). One exchangeable proton not observed. | System 3 Method F | m/z 346 (M + H)⁺ (ES⁺), at 2.17 min, 229 nm |
| 12-1 | Isomer 2: 8-(2-(3-Methyl-1,2,4-oxadiazol-5-yl)-2-azabicyclo[2.2.2]octan-5-yl)-2,8-diazaspiro[4.5]decan-3-one | A 19 and 28 | AV | ¹H NMR (400 MHz, Methanol-d₄) δ 4.08-4.01 (m, 1H), 3.76-3.68 (m, 1H), 3.41-3.34 (m, 1H), 3.20 (s, 2H), 2.70-2.26 (m, 4H), 2.38-2.31 (m, 2H), 2.22 (s, 2H), 2.17 (s, 3H), 2.13-2.03 (m, 1H), 1.97-1.88 (m, 1H), 1.87-1.79 (m, 1H), 1.79-1.60 (m, 7H). One exchangeable proton not observed. | System 3 Method F | m/z 346 (M + H)⁺ (ES⁺), at 2.25 min, 229 nm |
| 12-2 | Isomer 2: 8-(2-(3-Methyl-1,2,4-oxadiazol-5-yl)-2-azabicyclo[2.2.2]octan-5-yl)-1-oxa-3,8-diazaspiro[4.5]decan-2-one | A 22 and 28 | AW | ¹H NMR (400 MHz, Methanol-d₄) δ 4.08-4.01 (m, 1H), 3.76-3.68 (m, 1H), 3.45-3.35 (m, 2H), 2.73 (s, 2H), 2.46 (s, 2H), 2.39-2.30 (m, 2H), 2.17 (s, 3H), 2.13-2.05 (m, 1H), 2.01-1.89 (m, 3H), 1.88-1.64 (m, 7H). One exchangeable proton not observed. | System 3 Method F | m/z 348 (M + H)⁺ (ES⁺), at 2.29 min, 230 nm |
| 12-3 | Isomer 1: 8-(8-(3-(Trifluoromethyl)-1,2,4-oxadiazol-5-yl)-8-azabicyclo[3.2.1]octan-3-yl)-2,8-diazaspiro[4.5]decan-3-one | A 19 and 60 | AX | 1H NMR (400 MHz, Methanol-d₄) δ 4.56-4.48 (m, 2H), 3.18 (s, 2H), 2.95-2.81 (m, 1H), 2.67-2.39 (m, 4H), 2.20 (s, 2H), 2.18-2.09 (m, 2H), 2.06-1.98 (m, 2H), 1.95-1.86 (m, 2H), 1.75-1.59 (m, 6H). One exchangeable proton not observed. | System 3 Method F | m/z 400 (M + H)⁺ (ES⁺), at 3.07 min, 239 nm |
| 12-3 | Isomer 2: 8-(8-(3-(Trifluoromethyl)-1,2,4-oxadiazol-5-yl)-8-azabicyclo[3.2.1]octan-3-yl)-2,8-diazaspiro[4.5]decan-3-one | A 19 and 60 | AX | 1H NMR (400 MHz, Methanol-d₄) δ 4.68-4.61 (m, 1H), 4.48-4.40 (m, 2H), 3.21 (s, 2H), 2.71-2.38 (m, 4H), 2.38-2.30 (m, 1H), 2.22 (s, 2H), 2.19-2.12 (m, 3H), 2.12-2.04 (m, 2H), 2.03-1.94 (m, 2H), 1.76-1.66 (m, 4H). One exchangeable proton not observed. | System 3 Method F | m/z 400 (M + H)⁺ (ES⁺), at 3.40 min, 239 nm |

TABLE 3-continued

Table 3 - NMR and LCMS properties and the methods used to prepare and purify compounds represented by Examples 1 - 12-14

| Ex. No. | Name | Synthetic Method and Intermediates Used | Purification Method | $^1$H NMR | LCMS System and Method | LCMS data |
|---|---|---|---|---|---|---|
| 12-4 | Isomer 1: 8-(8-(3-(Trifluoromethyl)-1,2,4-oxadiazol-5-yl)-8-azabicyclo[3.2.1]octan-3-yl)-1-oxa-3,8-diazaspiro[4.5]decan-2-one | A 22 and 60 | AY | $^1$H NMR (400 MHz, Methanol-d$_4$) δ 4.60-4.44 (m, 2H), 3.35-3.32 (m, 2H), 3.00-2.85 (m, 1H), 2.77-2.47 (m, 4H), 2.22-2.07 (m, 2H), 2.07-1.84 (m, 6H), 1.83-1.61 (m, 4H). One exchangeable proton not observed. | System 3 Method F | m/z 402 (M + H)$^+$ (ES$^+$), at 3.24 min, 238 nm |
| 12-4 | Isomer 2: 8-(8-(3-(Trifluoromethyl)-1,2,4-oxadiazol-5-yl)-8-azabicyclo[3.2.1]octan-3-yl)-1-oxa-3,8-diazaspiro[4.5]decan-2-one | A 22 and 60 | AY | $^1$H NMR (400 MHz, Methanol-d$_4$) δ 4.50-4.37 (m, 2H), 3.36 (s, 2H), 2.85-2.46 (m, 4H), 2.43-2.33 (m, 1H), 2.25-1.91 (m, 10H), 1.91-1.76 (m, 2H). One exchangeable proton not observed. | System 3 Method F | m/z 402 (M + H)$^+$ (ES$^+$), at 3.58 min, 239 nm |
| 12-6 | Isomer 1: (1R,5S,6r)-3-(2-(3-Methyl-1,2,4-oxadiazol-5-yl)-2-azaspiro[3.4]octan-6-yl)-N-(1-methylcyclobutyl)-3-azabicyclo[3.1.0]hexane-6-carboxamide | A 62 and 12 | AZ then BA | $^1$H NMR (400 MHz, Methanol-d$_4$) δ 4.16-3.97 (m, 4H), 3.13-3.03 (m, 2H), 2.71-2.61 (m, 1H), 2.47-2.36 (m, 2H), 2.32-2.20 (m, 2H), 2.16 (s, 3H), 2.11-1.90 (m, 6H), 1.88-1.76 (m, 6H), 1.63-1.48 (m, 1H), 1.41 (s, 3H). One exchangeable proton not observed. | System 3 Method F | m/z 384 (M − H)$^-$ (ES$^-$), at 3.12 min, 227 nm |
| 12-6 | Isomer 1: (1R,5S,6r)-3-(2-(3-Methyl-1,2,4-oxadiazol-5-yl)-2-azaspiro[3.4]octan-6-yl)-N-(1-methylcyclobutyl)-3-azabicyclo[3.1.0]hexane-6-carboxamide | A 62 and 12 | AZ then BA | $^1$H NMR (400 MHz, Methanol-d$_4$) δ 4.14-3.97 (m, 4H), 3.13-3.03 (m, 2H), 2.70-2.60 (m, 1H), 2.45-2.35 (m, 2H), 2.33-2.20 (m, 2H), 2.16 (s, 3H), 2.10-1.90 (m, 6H), 1.88-1.74 (m, 6H), 1.62-1.50 (m, 1H), 1.41 (s, 3H). One exchangeable proton not observed. | System 3 Method F | m/z 384 (M − H)$^-$ (ES$^-$), at 3.11 min, 225 nm |
| 12-7 | Isomer 2: 1-(8-(3-Methyl-1,2,4-oxadiazol-5-yl)-8-azabicyclo[3.2.1]octan-3-yl)-N-(1-(trifluoromethyl)cyclobutyl)piperidine-4-carboxamide | B 24 and 63 | BB | $^1$H NMR (400 MHz, Methanol-d$_4$) δ 4.37-4.28 (m, 2H), 3.24-3.16 (m, 2H), 2.56-2.39 (m, 4H), 2.29-2.19 (m, 2H), 2.18 (s, 3H), 2.17-2.12 (m, 2H), 2.10-1.93 (m, 6H), 1.93-1.82 (m, 4H), 1.82-1.64 (m, 4H). One exchangeable proton not observed. | System 3 Method F | m/z 442 (M + H)$^+$ (ES$^+$), at 3.30 min, 202 nm |
| 12-8 | Isomer 2: N-(1-Ethylcyclobutyl)-1-(8-(3-methyl-1,2,4-oxadiazol-5-yl)-8-azabicyclo[3.2.1]octan-3-yl)piperidine-4-carboxamide | B 24 and 64 | BC | $^1$H NMR (400 MHz, Methanol-d$_4$) δ 4.36-4.29 (m, 2H), 3.25-3.17 (m, 2H), 2.28-2.21 (m, 1H), 2.18 (s, 3H), 2.17-2.09 (m, 5H), 2.09-1.97 (m, 6H), 1.93-1.79 (m, 8H), 1.79-1.65 (m, 4H), 0.81 (t, J = 7.3 Hz, 3H). One exchangeable proton not observed. | System 3 Method F | m/z 402 (M + H)$^+$ (ES$^+$), at 3.23 min, 202 nm |
| 12-11 | Isomer 2: 1-(8-(3-Methyl-1,2,4-oxadiazol-5-yl)-8-azabicyclo[3.2.1]octan-3-yl)-N-(1-methylcyclopentyl)piperidine-4-carboxamide | B 24 and 65 | BD | $^1$H NMR (400 MHz, Methanol-d$_4$) δ 4.33 (s, 2H), 3.24-3.17 (m, 2H), 2.29-2.21 (m, 1H), 2.18 (s, 3H), 2.17-1.94 (m, 9H), 1.93-1.79 (m, 4H), 1.77-1.54 (m, 10H), 1.36 (s, 3H). One exchangeable proton not observed. | System 3 Method F | m/z 402 (M + H)$^+$ (ES$^+$), at 3.61 min, 202 nm |

TABLE 3-continued

Table 3 - NMR and LCMS properties and the methods used to prepare and purify compounds represented by Examples 1 - 12-14

| Ex. No. | Name | Synthetic Method and Intermediates Used | Purification Method | ¹H NMR | LCMS System and Method | LCMS data |
|---|---|---|---|---|---|---|
| 12-12 | Isomer 2: 1-(8-(3-Methyl-1,2,4-oxadiazol-5-yl)-8-azabicyclo[3.2.1]octan-3-yl)-N-((1-methylcyclobutyl)methyl)piperidine-4-carboxamide | A 68 and 18 | BE | ¹H NMR (400 MHz, Methanol-$d_4$) δ 4.36-4.29 (m, 2H), 3.26-3.18 (m, 2H), 3.16 (s, 2H), 2.30-2.20 (m, 2H), 2.18 (s, 3H), 2.16-1.98 (m, 6H), 1.95-1.81 (m, 8H), 1.81-1.72 (m, 4H), 1.69-1.59 (m, 2H), 1.10 (s, 3H). One exchangeable proton not observed. | System 3 Method F | m/z 400 (M − H)⁻ (ES⁻), at 3.33 min, 202 nm |
| 12-13 | Isomer 2: (1R,5S,6r)-3-(8-(3-methyl-1,2,4-oxadiazol-5-yl)-8-azabicyclo[3.2.1]octan-3-yl)-N-(1-methylcyclobutyl)-3-azabicyclo[3.1.0]hexane-6-carboxamide | A 62 and 18 | BF | ¹H NMR (400 MHz, Methanol-$d_4$) δ 4.29-4.20 (m, 2H), 2.49-2.42 (m, 1H), 2.33-2.15 (m, 7H), 2.18 (s, 3H), 2.07-1.79 (m, 14H), 1.41 (s, 3H). One exchangeable proton not observed. | System 3 Method F | m/z 384 (M − H)⁻ (ES⁻), at 3.77 min, 230 nm |
| 12-14 | Isomer 1: N-(1-Methylcyclobutyl)-1-(8-(3-(trifluoromethyl)-1,2,4-oxadiazol-5-yl)-8-azabicyclo[3.2.1]octan-3-yl)piperidine-4-carboxamide | B 69 and 25 | BG | ¹H NMR (400 MHz, Methanol-$d_4$) δ 4.56-4.48 (m, 2H), 3.04-2.96 (m, 2H), 2.94-2.83 (m, 1H), 2.30-2.19 (m, 2H), 2.18-2.05 (m, 5H), 2.03-1.94 (m, 4H), 1.93-1.87 (m, 2H), 1.87-1.77 (m, 2H), 1.77-1.60 (m, 6H), 1.40 (s, 3H). One exchangeable proton not observed. | System 3 Method F | m/z 442 (M − H)⁺ (ES⁺), at 3.89 min, 202 nm |
| 12-14 | Isomer 2: N-(1-Methylcyclobutyl)-1-(8-(3-(trifluoromethyl)-1,2,4-oxadiazol-5-yl)-8-azabicyclo[3.2.1]octan-3-yl)piperidine-4-carboxamide | B 69 and 25 | BG | ¹H NMR (400 MHz, Methanol-$d_4$) δ 4.46-4.39 (m, 2H), 3.27-3.19 (m, 2H), 2.34-2.20 (m, 3H), 2.19-2.09 (m, 5H), 2.08-2.03 (m, 2H), 2.02-1.93 (m, 4H), 1.90-1.80 (m, 4H), 1.79-1.64 (m, 4H), 1.41 (s, 3H). One exchangeable proton not observed. | System 3 Method F | m/z 442 (M − H)⁺ (ES⁺), at 4.27 min, 202 nm |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen*, 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader. $pEC_{50}$ and $E_{max}$ figures were calculated from the resulting data for each receptor subtype and the results are set out in Table 4 below.

For the vast majority of examples at least two diastereomers exist and these have been separated, unless otherwise stated, using the techniques of reversed phase HPLC, chiral HPLC or chiral SFC. Isomer assignment (Isomer 1, Isomer 2, etc.) is based on the retention time of the compound using the separation technique that was performed in the final purification step. By implication, this could be reversed phase HPLC, chiral HPLC or chiral SFC retention time, and this will vary from compound to compound.

Analytical data for active isomers is reported in Table 3. Data for several weakly active compounds are included in Table 4 to highlight the preference for absolute stereochemistry.

TABLE 4

| | Muscarinic Activity | | | |
|---|---|---|---|---|
| Ex. No. | $pEC_{50}$ M1 (% Emax cf. ACh) | $pEC_{50}$ M2 (% Emax cf. ACh) | $pEC_{50}$ M3 (% Emax cf. ACh) | $pEC_{50}$ M4 (% Emax cf. ACh) |
| ACh | 8.33 (102) | 7.82 (105) | 8.12 (115) | 8.09 (110) |
| 1-1 | 4.99 (48) | NT | NT | 6.29 (77) |
| 2-1 Isomer 2 | <4.70 (56) | <4.70 (2) | <4.70 (3) | 6.52 (41) |
| 2-2 Isomer 2 | 6.13 (40) | <4.70 (2) | <4.70 (3) | 6.93 (51) |
| 2-3 Isomer 2 | <4.70 (9) | NT | NT | 6.29 (32) |
| 3-1 Isomer 2 | 5.08 (58) | NT | NT | 5.91 (68) |
| 4-1 | 4.70 (50) | NT | NT | 6.00 (85) |
| 5-1 Isomer 1 | <4.70 (9) | NT | NT | 5.90 (55) |
| 6-1 Isomer 1 | <4.70 (23) | <4.70 (2) | <4.70 (2) | 6.53 (51) |
| 6-2 Isomer 1 | 6.80 (34) | NT | NT | <4.70 (9) |
| 6-2 Isomer 2 | 7.20 (81) | NT | NT | 6.77 (39) |
| 6-3 Isomer 2 | 7.49 (33) | <4.70 (3) | <4.70 (1) | <4.70 (7) |
| 6-4 Isomer 1 | 6.62 (49) | NT | NT | <4.70 (15) |
| 6-4 Isomer 2 | 6.59 (87) | <4.70 (5) | <4.70 (32) | 6.28 (39) |
| 6-5 Isomer 2 | 6.83 (100) | <4.70 (31) | <4.70 (11) | 6.71 (79) |
| 7-1 Isomer 1 | <4.70 (18) | <4.70 (11) | <4.70 (7) | 6.82 (85) |
| 7-1 Isomer 2 | 5.64 (33) | <4.70 (15) | <4.70 (6) | 7.07 (99) |
| 8-1 Isomer 2 | <4.70 (24) | NT | NT | 5.90 (38) |
| 8-2 Isomer 1 | 6.67 (30) | NT | NT | <4.70 (9) |
| 8-3 Isomer 1 | 6.53 (39) | <4.70 (4) | <4.70 (1) | <4.70 (67) |
| 8-4 Isomer 1 | 6.24 (98) | NT | NT | 6.19 (76) |
| 9-1 Isomer 1 | <4.70 (15) | <4.70 (21) | <4.70 (1) | 6.98 (77) |
| 9-2 Isomer 2 | 6.66 (109) | <4.70 (27) | 5.20 (42) | 6.13 (74) |
| 10-1 Isomer 1 | 5.87 (32) | NT | NT | 6.89 (73) |
| 10-1 Isomer 2 | 5.18 (43) | NT | NT | 6.28 (72) |
| 10-2 Isomer 1 | 7.03 (66) | <4.70 (3) | <4.70 (5) | <4.70 (10) |
| 10-2 Isomer 2 | 6.31 (53) | NT | NT | <4.70 (15) |
| 10-3 Racemic mixture | 6.43 (97) | NT | NT | <4.70 (10) |
| 10-4 Isomer 1 | 6.17 (123) | NT | NT | 7.00 (85) |
| 10-4 Isomer 2 | 7.26 (58) | NT | NT | 7.63 (64) |
| 10-4 Isomer 3 | 5.03 (81) | NT | NT | 5.66 (71) |
| 10-4 Isomer 4 | <4.70 (18) | NT | NT | 6.06 (36) |
| 10-5 Isomer 1 | <4.70 (21) | NT | NT | 6.66 (33) |
| 10-6 Isomer 1 | 6.18 (76) | <4.70 (60) | <4.70 (4) | 7.11 (77) |
| 10-7 Isomer 1 | 5.43 (44) | <4.70 (15) | <4.70 (2) | 6.98 (89) |
| 10-7 Isomer 2 | 5.37 (70) | NT | NT | 6.40 (76) |
| 10-8 Isomer 1 | 6.17 (37) | NT | NT | 7.03 (91) |
| 10-8 Isomer 2 | 5.81 (35) | NT | NT | 6.53 (73) |
| 10-9 Isomer 2 | 5.88 (53) | NT | NT | 6.32 (56) |
| 10-10 Isomer 1b | <4.70 (6) | NT | NT | 6.29 (56) |
| 10-10 Isomer 2a | <4.70 (3) | NT | NT | 5.84 (52) |
| 10-10 Isomer 2b | <4.70 (14) | NT | NT | 6.50 (72) |
| 10-11 Racemic mixture | 5.40 (56) | NT | NT | 6.66 (101) |
| 10-12 Isomer 1 | <4.70 (22) | NT | NT | 6.51 (100) |
| 10-12 Isomer 2 | <4.70 (24) | NT | NT | 7.26 (119) |
| 11-1 Isomer 2 | 5.50 (48) | NT | NT | 5.98 (69) |
| 11-2 Isomer 2 | 8.02 (67) | <4.70 (8) | <4.70 (5) | <4.70 (15) |
| 11-3 Isomer 2 | 7.15 (65) | <4.70 (21) | <4.70 (22) | <4.70 (11) |
| 12-1 Isomer 1 | 6.22 (58) | NT | NT | <4.70 (5) |

TABLE 4-continued

| Ex. No. | pEC$_{50}$ M1 (% Emax cf. ACh) | pEC$_{50}$ M2 (% Emax cf. ACh) | pEC$_{50}$ M3 (% Emax cf. ACh) | pEC$_{50}$ M4 (% Emax cf. ACh) |
|---|---|---|---|---|
| 12-1 Isomer 2 | 7.49 (106) | <4.70 (6) | <4.70 (2) | 6.93 (30) |
| 12-2 Isomer 2 | 6.40 (80) | <4.70 (14) | <4.70 (1) | <4.70 (18) |
| 12-3 Isomer 1 | 7.50 (67) | <4.70 (19) | <4.70 (31) | <4.70 (14) |
| 12-3 Isomer 2 | 8.30 (103) | <4.70 (14) | <4.70 (70) | 6.70 (23) |
| 12-7 Isomer 2 | 6.27 (109) | NT | NT | 5.70 (109) |
| 12-8 Isomer 2 | 6.87 (104) | 5.61 (33) | <4.70 (3) | 6.03 (109) |
| 12-11 Isomer 2 | 6.18 (103) | NT | NT | 5.57 (83) |
| 12-12 Isomer 2 | 8.43 (80) | NT | NT | 6.68 (107) |
| 12-13 Isomer 2 | 6.48 (102) | NT | NT | 6.09 (69) |
| 12-14 Isomer 1 | 6.04 (47) | NT | NT | <4.70 (6) |
| 12-14 Isomer 2 | 7.73 (115) | <4.70 (25) | <4.70 (9) | 6.48 (40) |
| 12-15 Isomer 2 | 6.60 (113) | <4.70 (18) | <4.70 (6) | 5.33 (75) |
| 12-16 Isomer 1 | 7.49 (108) | 6.36 (62) | <4.70 (13) | 7.41 (104) |
| 12-16 Isomer 2 | 7.28 (118) | <4.70 (10) | <4.70 (4) | 6.25 (62) |
| 12-18 Isomer 1 | 7.00 (87) | 5.23 (27) | <4.70 (15) | 6.68 (62) |
| 12-18 Isomer 2 | 8.63 (92) | 6.59 (90) | 5.72 (48) | 7.83 (92) |
| 12-22 Isomer 2 | 8.06 (102) | 5.68 (81) | 4.90 (52) | 6.23 (108) |
| 12-23 Isomer 2 | 7.59 (132) | <4.70 (13) | <4.70 (25) | 6.92 (30) |
| 12-24 Isomer 1 | 6.08 (74) | NT | NT | <4.70 (16) |
| 12-24 Isomer 2 | 7.58 (102) | 5.33 (60) | <4.70 (25) | 6.02 (83) |
| 12-25 Isomer 1 | 6.70 (102) | <4.70 (31) | <4.70 (50) | <4.70 (22) |
| 12-25 Isomer 2 | 8.55 (91) | 6.15 (84) | 5.29 (57) | 6.82 (119) |
| 12-27 Isomer 2 | 6.92 (76) | <4.70 (14) | <4.70 (15) | <4.70 (21) |

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of formula (1):

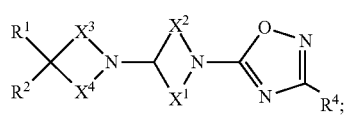

or a salt thereof, wherein:

the ring system formed by $X^1$ and $X^2$ is selected from:

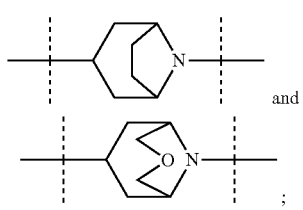

the ring system formed by $X^3$ and $X^4$ is selected from:

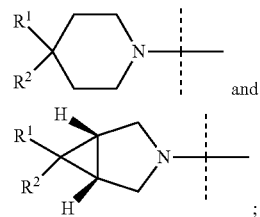

$R^1$ is CONR$^5$R$^6$;

$R^2$ is selected from hydrogen, fluorine, cyano and a C$_{1-3}$ hydrocarbon group which is optionally substituted with one to six fluorine atoms;

$R^4$ is H or C$_{1-6}$ alkyl optionally substituted with one or more fluorine atoms;

$R^5$ is hydrogen or a non-aromatic C$_{1-10}$ hydrocarbon group optionally substituted with one or more fluorine atoms;

$R^6$ is hydrogen or a non-aromatic C$_{1-10}$ hydrocarbon group optionally substituted with one or more fluorine atoms.

2. The compound according to claim 1 which is a compound of formula (2):

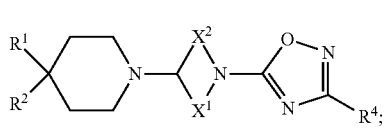

or a salt thereof.

3. The compound according to claim 1 which is a compound of formula (3):

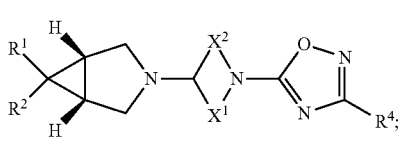

(3)

or a salt thereof.

4. The compound according to claim 1, or a salt thereof, wherein the ring system formed by $X^1$ and $X^2$ is:

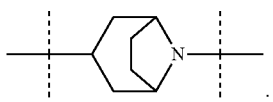

5. The compound according to claim 1, or a salt thereof, wherein $R^5$ is methyl, ethyl or methylcyclobutyl.

6. The compound according to claim 1, or a salt thereof, wherein $R^5$ is methylcyclobutyl.

7. The compound according to claim 1, or a salt thereof, wherein $R^6$ is H, methyl, ethyl or methylcyclobutyl.

8. The compound according to claim 1, or a salt thereof, wherein $R^6$ is H.

9. The compound according to claim 1, or a salt thereof, wherein $R^1$ is selected from:

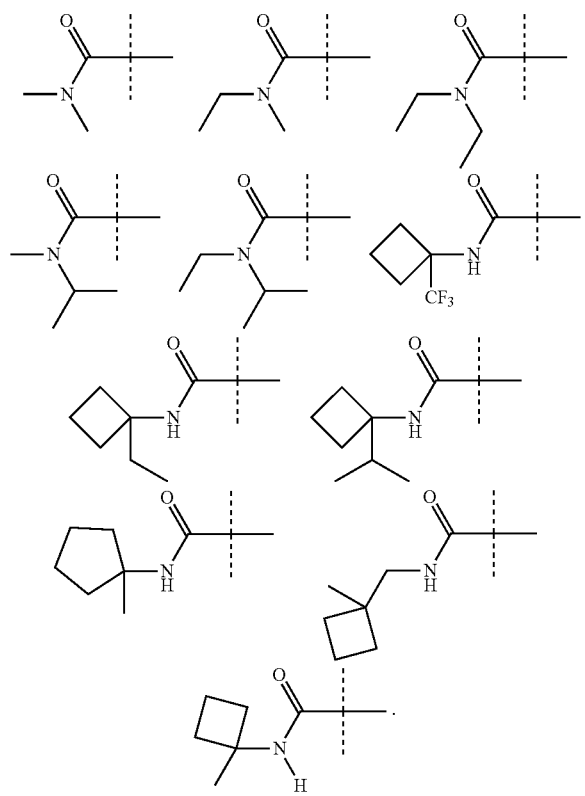

10. The compound according to claim 1, or a salt thereof, wherein $R^1$ is:

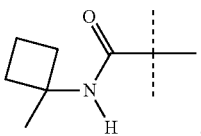

11. The compound according to claim 1, or a salt thereof, wherein $R^2$ is selected from H, methyl, cyano and F.

12. The compound according to claim 1, or a salt thereof, wherein $R^2$ is H.

13. The compound according to claim 1, or a salt thereof, wherein $R^4$ is methyl, trifluoromethyl, ethyl or isopropyl.

14. The compound according to claim 1, which is selected from:

N-(1-Methylcyclobutyl)-1-[8-(3-methyl-1,2,4-oxadiazol-5-yl)-8-azabicyclo[3.2.1]oct-3-yl]piperidine-4-carboxamide;

(1R,5S,6r)-N,N-Diethyl-3-[9-(3-methyl-1,2,4-oxadiazol-5-yl)-3-oxa-9-azabicyclo[3.3.1]non-7-yl]-3-azabicyclo[3.1.0] hexane-6-carboxamide;

1-(8-(3-Methyl-1,2,4-oxadiazol-5-yl)-8-azabicyclo[3.2.1]octan-3-yl)-N-(1-(trifluoromethyl)cyclobutyl)piperidine-4-carboxamide;

N-(1-Ethylcyclobutyl)-1-(8-(3-methyl-1,2,4-oxadiazol-5-yl)-8-azabicyclo[3.2.1]octan-3-yl)piperidine-4-carboxamide;

N-(1-isopropylcyclobutyl)-1-(8-(3-methyl-1,2,4-oxadiazol-5-yl)-8-azabicyclo[3.2.1]octan-3-yl)piperidine-4-carboxamide;

1-(8-(3-Methyl-1,2,4-oxadiazol-5-yl)-8-azabicyclo[3.2.1]octan-3-yl)-N-(1-methylcyclopentyl)piperidine-4-carboxamide;

1-(8-(3-Methyl-1,2,4-oxadiazol-5-yl)-8-azabicyclo[3.2.1]octan-3-yl)-N-((1-methylcyclobutyl)methyl)piperidine-4-carboxamide;

(1R,5S,6r)-3-(8-(3-methyl-1,2,4-oxadiazol-5-yl)-8-azabicyclo[3.2.1]octan-3-yl)-N-(1-methylcyclobutyl)-3-azabicyclo[3.1.0]hexane-6-carboxamide;

N-(1-Methylcyclobutyl)-1-(8-(3-(trifluoromethyl)-1,2,4-oxadiazol-5-yl)-8-azabicyclo[3.2.1]octan-3-yl)piperidine-4-carboxamide;

(1R,5S,6r)-N-isopropyl-N-methyl-3-(9-(3-methyl-1,2,4-oxadiazol-5-yl)-3-oxa-9-azabicyclo[3.3.1]nonan-7-yl)-3-azabicyclo[3.1.0]hexane-6-carboxamide;

(1R,5S,6r)-N,N-diethyl-3-(9-(3-(trifluoromethyl)-1,2,4-oxadiazol-5-yl)-3-oxa-9-azabicyclo[3.3.1]nonan-7-yl)-3-azabicyclo[3.1.0]hexane-6-carboxamide;

(1R,5S,6r)-N-ethyl-N-methyl-3-(8-(3-methyl-1,2,4-oxadiazol-5-yl)-8-azabicyclo[3.2.1]octan-3-yl)-3-azabicyclo[3.1.0]hexane-6-carboxamide;

(1R,5S,6r)-N,N-diethyl-3-(8-(3-methyl-1,2,4-oxadiazol-5-yl)-8-azabicyclo[3.2.1]octan-3-yl)-3-azabicyclo[3.1.0]hexane-6-carboxamide;

(1R,5S,6r)-N,N-dimethyl-3-(9-(3-(trifluoromethyl)-1,2,4-oxadiazol-5-yl)-3-oxa-9-azabicyclo[3.3.1]nonan-7-yl)-3-azabicyclo[3.1.0]hexane-6-carboxamide;

(1R,5S,6r)-N-isopropyl-N-methyl-3-(8-(3-methyl-1,2,4-oxadiazol-5-yl)-8-azabicyclo[3.2.1]octan-3-yl)-3-azabicyclo[3.1.0]hexane-6-carboxamide;

(1R,5S,6r)-3-(8-(3-methyl-1,2,4-oxadiazol-5-yl)-8-azabicyclo[3.2.1]octan-3-yl)-N-(1-(trifluoromethyl)cyclobutyl)-3-azabicyclo[3.1.0]hexane-6-carboxamide;

or a salt thereof.

15. The compound according to claim 1, which is N-(1-Methylcyclobutyl)-1-(8-(3-(trifluoromethyl)-1,2,4-oxadiazol-5-yl)-8-azabicyclo[3.2.1]octan-3-yl)piperidine-4-carboxamide or a salt thereof.

16. The compound according to claim 1, which is (1R,5S,6r)-N,N-diethyl-3-(9-(3-(trifluoromethyl)-1,2,4-oxadiazol-5-yl)-3-oxa-9-azabicyclo[3.3.1]nonan-7-yl)-3-azabicyclo[3.1.0]hexane-6-carboxamide or a salt thereof.

17. A pharmaceutical composition comprising a compound according to claim 1, or a salt thereof, and a pharmaceutically acceptable excipient.

18. A method of treating a cognitive disorder selected from Schizophrenia, Alzheimer's disease and dementia with Lewy bodies, or for the treatment or lessening the severity of acute, chronic, neuropathic, or inflammatory pain comprising administering an effective amount of a compound according to claim 1, or a salt thereof, to a subject in need thereof.

19. The method according to claim 18 wherein the cognitive disorder is Alzheimer's disease.

20. The method according to claim 18 wherein the cognitive disorder is dementia with Lewy bodies.

* * * * *